US009603522B2

(12) United States Patent
Lee et al.

(10) Patent No.: US 9,603,522 B2
(45) Date of Patent: Mar. 28, 2017

(54) DETECTING NEUROCHEMICAL OR ELECTRICAL SIGNALS WITHIN BRAIN TISSUE

(75) Inventors: Kendall H. Lee, Rochester, MN (US); Kevin E. Bennet, Rochester, MN (US); Charles D. Blaha, Germantown, TN (US)

(73) Assignees: Mayo Foundation for Medical Education and Research, Rochester, MN (US); The University of Memphis Research Foundation, Memphis, TN (US)

( * ) Notice: Subject to any disclaimer, the term of this patent is extended or adjusted under 35 U.S.C. 154(b) by 1166 days.

(21) Appl. No.: 13/392,387

(22) PCT Filed: Aug. 26, 2010

(86) PCT No.: PCT/US2010/046807
§ 371 (c)(1),
(2), (4) Date: Feb. 24, 2012

(87) PCT Pub. No.: WO2011/028608
PCT Pub. Date: Mar. 10, 2011

(65) Prior Publication Data
US 2012/0165634 A1    Jun. 28, 2012

Related U.S. Application Data

(60) Provisional application No. 61/275,168, filed on Aug. 26, 2009.

(51) Int. Cl.
A61B 5/00    (2006.01)
A61N 1/05    (2006.01)
A61N 1/08    (2006.01)

(52) U.S. Cl.
CPC .............. *A61B 5/00* (2013.01); *A61B 5/4064* (2013.01); *A61B 5/6814* (2013.01);
(Continued)

(58) Field of Classification Search
CPC . A61B 2562/02; A61B 2562/043; A61B 5/00; A61B 5/6814; A61N 1/05; A61N 1/0531; A61N 1/0534; A61N 1/08
See application file for complete search history.

(56) References Cited

U.S. PATENT DOCUMENTS 5,650,061 A   7/1997   Kuhr et al.
5,806,517 A   9/1998   Gerhardt et al.
(Continued)

FOREIGN PATENT DOCUMENTS

WO   WO 2010/083208   7/2010
WO   WO 2011/028608   3/2011
(Continued)

OTHER PUBLICATIONS

Anastassiou et al. "Subsecond voltammetric separation between dopamine and serotonin in the presence of ascorbate," Anal Chem., 78(19):6990-6998, Oct. 1, 2006.
(Continued)

*Primary Examiner* — Navim Natnithithadha
(74) *Attorney, Agent, or Firm* — Fish & Richardson P.C.

(57) ABSTRACT

This document relates to methods and materials involved in detecting neurochemical signals, electrophysiological signals, ions, or combinations thereof with brain tissue. For example, methods and materials for using probes to detect neurochemical signals (e.g., neurotransmitter concentrations), electrical signals, or combinations thereof during deep brain stimulation are provided.

20 Claims, 35 Drawing Sheets

(52) U.S. Cl.
CPC ......... *A61N 1/0531* (2013.01); *A61N 1/0534* (2013.01); *A61B 5/4082* (2013.01); *A61B 2562/02* (2013.01); *A61B 2562/043* (2013.01); *A61N 1/05* (2013.01); *A61N 1/08* (2013.01)

(56) References Cited

U.S. PATENT DOCUMENTS

| | | | |
|---|---|---|---|
| 6,164,284 A | 12/2000 | Schulman | |
| 7,209,788 B2 | 4/2007 | Nicolelis | |
| 7,440,806 B1 | 10/2008 | Whitehurst et al. | |
| 7,747,318 B2* | 6/2010 | John | A61N 1/0529 607/2 |
| 7,899,545 B2* | 3/2011 | John | A61B 5/4809 600/522 |
| 7,901,368 B2 | 3/2011 | Flaherty et al. | |
| 8,140,152 B2* | 3/2012 | John | A61N 1/0529 607/2 |
| 8,315,703 B2* | 11/2012 | Lozano | A61N 1/36082 607/45 |
| 8,359,100 B2* | 1/2013 | Cameron | A61N 1/36082 607/42 |
| 8,433,415 B2* | 4/2013 | Leiter | A61B 5/4094 600/544 |
| 8,473,060 B2* | 6/2013 | Leiter | A61B 5/4094 607/45 |
| 2002/0013612 A1* | 1/2002 | Whitehurst | A61N 1/36096 607/45 |
| 2004/0108223 A1 | 6/2004 | Jansson | |
| 2006/0009814 A1 | 1/2006 | Schulman | |
| 2006/0173509 A1 | 8/2006 | Lee et al. | |
| 2006/0195157 A1* | 8/2006 | Lee | A61B 5/4094 607/46 |
| 2006/0241717 A1* | 10/2006 | Whitehurst | A61N 1/36082 607/45 |
| 2007/0026440 A1 | 2/2007 | Broderick et al. | |
| 2008/0179197 A1 | 7/2008 | Wu | |
| 2008/0258116 A1 | 10/2008 | Viticoli et al. | |
| 2008/0288023 A1 | 11/2008 | John | |
| 2010/0032316 A1 | 2/2010 | Wu | |
| 2010/0312305 A1* | 12/2010 | Leiter | A61B 5/4094 607/45 |
| 2012/0088983 A1 | 4/2012 | Jung et al. | |
| 2012/0165634 A1* | 6/2012 | Lee | A61B 5/00 600/345 |
| 2013/0023745 A1 | 1/2013 | Lee et al. | |
| 2015/0360032 A1 | 12/2015 | Bennet | |
| 2016/0192872 A1 | 7/2016 | Lee | |

FOREIGN PATENT DOCUMENTS

| | | |
|---|---|---|
| WO | WO2015021470 A1 | 2/2015 |
| WO | WO2014110263 A2 | 7/2015 |

OTHER PUBLICATIONS

Jang et al. "Paired pulse voltammetry for differentiating complex analytes," Analyst. 137(6):1428-1435, Epub Feb. 2, 2012.
International Search Report and Written Opinion for PCT/US2014/10882, mailed Apr. 4, 2014, 12 pages.
International Search Report and Written Opinion for PCT/US2014/50550 mailed Nov. 20, 2014, 10 pages.
Office Action in U.S. Appl. No. 13/555,965, mailed Feb. 12, 2015, 8 pages.
U.S. Appl. No. 61/358,512, filed Jun. 25, 2010, 51 pages.
International Search Report and Written Opinion in International Application No. PCT/US2010/046807, mailed May 31, 2011, 9 pages.
International Preliminary Report on Patentability in International Application No. PCT/US2010/046807, mailed Mar. 8, 2012, 6 pages.

Abosch et al., "Stimulation of the subthalamic nucleus in Parkinson's disease does not produce striatal dopamine release," *Neurosurgery*, 2003, 53:1095-1102; discussion 1102-1095.
Adams, "In vivo electrochemical measurements in the CNS," *Prog Neurobiol*, 1990, 35(4):297-311.
Agnesi et al., "Wireless Instantaneous Neurotransmitter Concentration System-based amperometric detection of dopamine, adenosine, and glutamate for intraoperative neurochemical monitoring," *J Neurosurg.*, 2009, 111:701-711.
Aillon et al., "Near real-time measurement of glutamate concentration changes using biosensors in place of traditional methodologies," in Phillips PEM, Sandberg SG, Ahn S, Phillips AG (ed): proceeding of the 12th international conference on in vivo methods 2008. University of British Columbia, Vancouver, Canada. 2008, pp. 108-110.
Albin et al., "The functional anatomy of basal ganglia disorders," *Trends Neurosci.*, 1989, 12:366-375.
Anami et al., "Stepping stone sampling for retrieving artifactfree electroencephalogram during functional magnetic resonance imaging," *Neuroimage*, 2003, 19:281-295.
Anderson et al., "Mechanisms of deep brain stimulation: an intracellular study in rat thalamus," *J Physiol.*, 2004 559:301-313.
Bakker and Qin, "Electrochemical sensors," *Anal Chem.*, 2006, 78:3965-3984.
Bar-Gad et al., "Complex locking rather than complete cessation of neuronal activity in the globus pallidus of a 1-methyl-4-phenyl-1,2,3,6-tetrahydropyridine-treated primate in response to pallidal microstimulation," *J Neurosci.*, 2004, 24:7410-7419.
Bath et al., "Subsecond Adsorption and Desorption of Dopamine at Carbon-Fiber Microelectrodes," *Anal. Chem.*, 2000, 72:5994-6002.
Baur et al., "Fast-scan voltammetry of biogenic amines," *Anal Chem.*, 1988, 60:1268-1272.
Bekar et al., "Adenosine is crucial for deep brain stimulation-mediated attenuation of tremor," *Nat Med.*, 2008, 14:75-80.
Benabid et al., "Combined (thalamotomy and stimulation) stereotactic surgery of the VIM thalamic nucleus for bilateral Parkinson disease," *Appl Neurophysiol.*, 1987, 50:344-346.
Benabid, "Deep brain stimulation for Parkinson's disease," *Curr Opin Neurobiol.*, 2003, 13:696-706.
Benveniste, "Brain microdialysis," *J Neurochem.*, 1989, 52:1667-1679.
Bergman et al., "Pathophysiology of Parkinson's disease: from clinical neurology to basic neuroscience and back," *Mov. Disord.*, 2002, 17:S28-S40.
Bergman et al., "Reversal of experimental parkinsonism by lesions of the subthalamic nucleus," *Science*, 1990, 249:1436-1438.
Bergstrom and Garris, "Utility of a tripolar stimulating electrode for eliciting dopamine release in the rat striatum," *J Neurosci. Methods*, 1999, 87:201-208.
Beurrier et al., "High-frequency stimulation produces a transient blockade of voltage-gated currents in subthalamic neurons," *J Neurophysiol.*, 2001, 85:1351-1356.
Blagoev et al., "Modelling the magnetic signature of neuronal tissue," *NeuroImage*, 2007, 37:137-148.
Blaha and Phillips, "A critical assessment of electrochemical procedures applied to the measurement of dopamine and its metabolites during drug-induced and species-typical behaviours," *Behav Pharmacol.*, 1996, 7:675-708.
Blaha and Winn, "Modulation of dopamine efflux in the striatum following cholinergic stimulation of the substantia nigra in intact and pedunculopontine tegmental nucleus-lesioned rats," *J. Neurosci.*, 1993, 13(3):1035-1044.
Blaha et al., "Modulation of Dopamine Efflux in the Nucleus Accumbens after Cholinergic Stimulation of the Ventral Tegmental Area in Intact, Pedunculopontine Tegmental Nucleus-Lesioned, and Laterodorsal Tegmental Nucleus-Lesioned Rats," *J. Neurosci.*, 1996, 16:714-722.
Blaha et al., "Striatal dopamine release evoked by subthalamic stimulation in intact and 6-0HDA-lesioned rats: Relevance to deep brain stimulation in Parkinson's Disease," In: P. E. M. Phillips, S. G. Sandberg, S. Ahn, A. G. Phillips (Eds.), Monitoring Molecules in Neuroscience. University of British Columbia, Vancouver, BC, 2008, pp. 395-397.

(56) References Cited

OTHER PUBLICATIONS

Bledsoe et al., "Development of the Wireless Instantaneous Neurotransmitter Concentration System for intraoperative neurochemical monitoring using fast-scan cyclic voltammetry," *J Neurosurg.*, 2009, 111(4):712-723.

Bledsoe et al., "MRI compatible stereotaxic head-frame and navigation software for research in pigs," *Neuroscience*, 2008, Program#/Poster#: 695.8/UU92, 2 pages.

Bonmassar et al., "Visual evoked potential (VEP) measured by simultaneous 64-channel EEG and 3T fMRI," *Neuroreport*, 1999, 10:1893-1897.

Borland and Michael, "An introduction to electrochemical methods in neuroscience," in Michael AC, Borland LM (ed): Electrochemical Methods for Neuroscience. Boca Raton: CRC Press, 2007, 10 pages.

Borland et al., "Voltammetric study of extracellular dopamine near microdialysis probes acutely implanted in the striatum of the anesthetized rat," *J Neurosci Methods*, 2005, 146:149-158.

Breit et al., "Deep brain stimulation," *Cell Tissue Res*, 2004, 318:275-288.

Brown and Pilitsis, "Motor cortex stimulation for central and neuropathic facial pain: a prospective study of 10 patients and observations of enhanced sensory and motor function during stimulation," *Neurosurg.*, 2005, 56:290-297; discussion 290-297.

Bruet et al., "High frequency stimulation of the subthalamic nucleus increases the extracellular contents of striatal dopamine in normal and partially dopaminergic denervated rats," *J Neuropathol Exp Neurol.*, 2001, 60:15-24.

Bruet et al., "Neurochemical mechanisms induced by high frequency stimulation of the subthalamic nucleus: increase of extracellular striatal glutamate and GABA in normal and hemiparkinsonian rats," *J Neuropathol Exp Neurol.*, 2003, 62:1228-1240.

Burmeister et al., "Advances in the in vivo detection of GABA using enzyme coated microelectrode arrays," in Phillips PEM, Sandberg SG, Ahn S, Phillips AG (ed): proceeding of the 12th international conference on in Vivo methods 2008. University of British Columbia, Vancouver, Canada. 2008, p. 111-113.

Burmeister et al., "Improved ceramic-based multisite microelectrode for rapid measurements of L-glutamate in the CNS," *J Neurosci Methods*, 2002, 119:163-171.

Busenbark et al., "Accuracy of reported family histories of essential tremor," *Neurology*, 1996, 47:264-265.

Cahill et al., "Microelectrodes for the measurement of catecholamines in biological systems," *Anal Chem.*, 1996. 68(18):3180-3186.

Carmichael et al., "Functional MRI with active, fully implanted, deep brain stimulation systems: Safety and experimental confounds," *NeuroImage*, 2007, 37:508-517.

Cavus et al., "Decreased hippocampal vololume on MRI is associated with increased extracellular glutamate in epilepsy patients," *Epilepsia*, 2008, 49:1358-1366.

Cechova and Venton, "Transient adenosine efflux in the rat caudate-putamen," *J. Neurochem.*, 2008, 105:1253-1263.

Chang et al., "Studies of the neural mechanisms of deep brain stimulation in rodent models of Parkinson's disease," *Neurosci Biobehav Rev.*, 2008, 32:352-366.

Chow et al., "Delay in vesicle fusion revealed by electrochemical monitoring of single secretory events in adrenal chromaffin cells," *Nature*, 1992, 356(6364):60-63.

Clapp-Lilly et al., "An ultrastructural analysis of tissue surrounding a microdialysis probe," *J Neurosci Methods*, 1999, 90:129-142.

Covey et al., "Monitoring subthalamic nucleus-evoked dopamine release in the striatum using fast-scan cyclic voltammetry in vivo," in P.E.M. Phillips (Eds), Monitoring Molecules in Neuroscience. University of British Columbia, Vancouver, BC, 2008, 398-400.

Crespi et al., "In vivo voltammetry: from wire to wireless measurements," *J Neurosci Methods*, 2004. 140(1-2):153-61.

Cumming et al., "Kinetics of the uptake and distribution of the dopamine D(2,3) agonist (R)-N-[1-($^{11}$C)n-propylnorapomorphine in brain of healthy and MPTP-treated Gottingen miniature pigs," *Nucl Med Biol.*, 2003, 30:547-553.

Dale et al., "Listening to the brain: microelectrode biosensors for neurochemicals," *Trends Biotechnol.*, 2005, 23:420-428.

Dale et al., "Rapid adenosine release in the nucleus tractus solitarii during defense response in rats: real-time measurement in vivo," *J Physiol.*, 2002, 544(Pt 1):149-160.

Dall et al., "Quantitative [18F]fluorodopa/PET and histology of fetal mesencephalic dopaminergic grafts to the striatum of MPTP-poisoned minipigs," *Cell Transplant.*, 2002, 11:733-746.

Danielsen et al., "The DaNeX study of embryonic mesencephalic, dopaminergic tissue grafted to a minipig model of Parkinson's disease: preliminary findings of effect of MPTP poisoning on striatal dopaminergic markers," *Cell Transplant.*, 2000, 9:247-259.

Dobbing, "The influence of early nutrition on the development and myelination of the brain," *Proc Royal Soc Lond B Biol Sci.*, 1964 159:503-509.

Dommett et al., "How visual stimuli activate dopaminergic neurons at short latency," *Science*, 2005, 307:1476-1479.

Dostrovsky et al., "Microstimulation-induced inhibition of neuronal firing in human globus pallidus," *J Neurophysiol.*, 2000, 84:570-574.

Dugast et al., "Continuous in vivo monitoring of evoked dopamine release in the rat nucleus accumbens by amperometry," *Neuroscience*, 1994, 62:647-654.

Dunn et al., "Functional Brian Mapping at 9.4T Using a New MRI-Compatible Electrode Chronically Implanted in Rats," *Magnetic Resonance Med.*, 2009, 61:222-228.

Fedele et al., "Microdialysis in Parkinsonian patient basal ganglia: acute apomorphine-induced clinical and electrophysiological effects not paralleled by changes in the release of neuroactive amino acids," *Exp Neurol.*, 2001, 167:356-365.

Felix et al., "Stereotaxic atlas of the pig brain," *Brain Res Bull.*, 1999, 49:1-137.

Forster and Blaha, "Pedunculopontine tegmental stimulation evokes striatal dopamine efflux by activation of acetylocholine and glutamate receptors in the midbrain and pons of the rat," *Eur. J. Neurosci.*, 2003, 17:751-762.

Frank et al., "Hold your horses: impulsivity, deep brain stimulation, and medication in parkinsonism," *Science*, 2007, 318:1309-1312.

Garcia et al., "Dual effect of high-frequency stimulation on subthalamic neuron activity," *J Neurosci.*, 2003, 23:8743-8751.

Garcia et al., "High-frequency stimulation in Parkinson's disease: more or less?" *Trends Neurosci.*, 2005, 28:209-216

Garguilo and Michael, "Amperometric microsensors for monitoring choline in the extracellular fluid of brain," *J Neurosci Methods*, 1996, 70:73-82.

Garris et al., "Dissociation of dopamine release in the nucleus accumbens from intracranial self-stimulation," *Nature*, 1999, 398(6722):67-9.

Garris et al., "Dopamine release and uptake both decrease in the partially denervated striatum in proportion to the loss of dopamine terminals," *Brain Res.*, 1997, 753(2):225-34.

Garris et al., "In vivo voltammetry with telemetry," in Michael AC, Borland LM (ed): Electrochemical Methods for Neuroscience. Boca Rhaton: CRC Press, 2007, pp. 233-259.

Garris et al., "Real-time measurement of electrically evoked extracellular dopamine in the striatum of freely moving rats," *J Neurochem.*, 1997, 68:152-161.

Garris et al., "Wireless transmission of fast-scan cyclic voltammetry at a carbon-fiber microelectrode: proof of principle," *J Neurosci Methods*, 2004, 140(1-2):103-115.

Gerhardt, "Rapid chronocoulometric measurements of norepinephrine overflow and clearance in CNS tissues," Neuromethods: voltammetric methods in brain systems, ed. G.B. A Boulton, RN Adams. 1995, Totowa, NJ: Human Press Inc. 117-51.

Gourine et al., "Adenosine release in nucleus tractus solitarii does not appear to mediate hypoxia-induced respiratory depression in rats," *J Physiol.*, 2002, 544:161-70.

Graybiel, "Neurotransmitters and neuromodulators in the basal ganglia," *Trends Neurosci*, 1990, 13:244-254.

Greene, "Deep-brain stimulation for generalized dystonia," *N Engl J Med*, 2005, 352:498-500.

(56) References Cited

OTHER PUBLICATIONS

Groh and Ney, "Anaethesia for magnetic resonance imaging," *Curr Opin Anaethesiol.*, 1997, 10:303-308.
Halassa et al., "Astrocytic Modulation of Sleep Homeostasis and Cognitive Consequences of Sleep Loss," *Neuron*, 2009, 61:213-219.
Hardesty and Sackeim, "Deep brain stimulation in movement and psychiatric disorders," *Biol Psychiatry*, 2007, 61:831-835.
Hardman et al., "Comparison of the Basal Ganglia in Rats, Marmosets, Macaques, Baboons, and Humans: Volume and Neuronal Number for the Output, Internal Relay and Striatal Modulating Nuclei," *J Camp. Neural.*, 2002, 445:238-255.
Hascup et al., "Determining the source of resting and physiologically-evoked L-glutamate levels using enzyme-based microelectrode arrays in awake rats," in Phillips PEM, Sandberg SG, Ahn S, Phillips AG (ed): proceeding of the 12th international conference on in vivo methods 2008. University of British Columbia, Vancouver, Canada. 2008, pp. 164-167.
Hascup et al., "Second-by second measures of L-glutamate and other neurotransmitter using enzyme based microelectrode arrays," in Micheal AC, Borland LM (ed): Electrochemical methods for neuroscience. CRC. 2006, 47 pages.
Henderson and Lad, "Motor cortex stimulation and neuropathic facial pain," *Neurosurg Focus*, 2006, 21:E6, 4 pages.
Herzog et al., "Most effective stimulation site in subthalamic deep brain stimulation for Parkinson's disease," *Mov. Disord.*, 2004, 19:1050-1054.
Hilker et al., "Deep brain stimulation of the subthalamic nucleus does not increase the striatal dopamine concentration in parkinsonian humans," *Mov Disord*, 2003, 18:41-48.
Hinzman et al., "Alterations in glutamate neurotransmission after traumatic brain injury: Study using enzyme-based microelectrode arrays," in Phillips PEM, Sandberg SG, Ahn S, Phillips AG (ed): proceeding of the 12th international conference on in vivo methods 2008. University of British Columbia, Vancouver, Canada. 2008, p. 372-374.
Hubble et al., "Deep brain stimulation for essential tremor," *Neurol.*, 1996, 46:1150-1153.
Huffman and Venton, "Carbon-fiber microelectrodes for in vivo applications," *Analyst.*, 2009, 134:18-24.
Hurley et al., "What has been learnt from study of dopamine receptors in Parkinson's disease?" *Pharmacol. Ther.*, 2002, 111:715-728.
Hyland et al., "Firing modes of midbrain dopamine cells in the freely moving rat," *Neurosci.*, 2002, 114:475-492.
Jackson et al., "Fast-scan cyclic voltammetry of 5-hydroxytryptamine," *Anal Chem.*, 1995, 67:1115-1120.
Jaquins-Gerstl and Michael, "Comparison of the brain penetration injury associated with microdialysis and voltammetry," *J Neurosci Methods*, 2009, 183:127-135.
Justice et al., "Voltammetry in the neuroscience," Clifton, NJ. Humana Press, 1987, 395 pages.
Kagohashi et al., "Wireless voltammetry recording in unanesthetised behaving rats," *Neurosci Res.*, 2008, 60:120-127.
Kawagoe et al., "pH-Dependent processes at Nafion-coated carbon-fiber microelectrodes," *J Electroanal Chem.*, 1993, 359:193-197.
Keeler et al., "Accessory equipment considerations with respect to MRI compatibility," *J Magn Reson Imaging*, 1998, 8:12-18.
Kern and Kumar, "Deep brain stimulation," *Neurologist*, 2007, 13:237-252.
Kimble et al., "Wireless Instantaneous Neurotransmitter Concentration Sensing System (WINCS) for Intraoperative Neurochemical Monitoring," $31^{st}$ *Annual International Conference of the IEEE EMBS*, 2009, 4 pages.
Kita and Kitai, "Efferent Projections of the Subthalamic Nucleus in the Rat: Light and Electron Microscopic Analysis with the PHA-L Method," *J Camp. Neural.*, 1987, 260:435-452.
Konradsson et al., "Second-by-second measurement of stimulated glutamate release and its modulation by α7 and mGlu 2/3 receptors: relevance to schizophrenia," in Phillips PEM, Sandberg SG, Ahn S, Phillips AG (ed): proceeding of the 12th international conference on in vivo methods 2008. University of British Columbia, Vancouver, Canada. 2008, pp. 123-126.
Krakow, "Imaging epileptic activity using functional MRI," *Neurodegener Dis*, 2008, 5:286-295.
Kristensen and Wightman, "Dispersion in flow injection analysis measured with microvoltammetric electrodes," *Anal Chem*, 1986, 58:986-988.
Kulagina et al., "Monitoring glutamate and ascorbate in the extracellular space of brain tissue with electrochemical microsensors," *Anal Chem.*, 1999, 71:5093-5100.
Lee et al, "Evolution of Deep Brain Stimulation: Human Electrometer and Smart Devices Supporting the Next Generation of Therapy," *Neuromodulation: Technology at the Neural Interface*, 2009, 12(2):85-103
Lee et al., "Dopamine efflux in the rat striatum evoked by electrical stimulation of the subthalamic nucleus: potential mechanism of action in Parkinson's disease," *Eur. J. Neurosci.*, 2006, 23-1005-1014.
Lee et al., "High-frequency stimulation of the subthalamic nucleus increases glutamate in the subthalamic nucleus of rats as demonstrated by in vivo enzyme-linked glutamate sensor," *Brain Res.*, 2007, 1162:121-129
Lee et al., "Neurotransmitter release from high-frequency stimulation of the subthalamic nucleus," *J Neurosurg.*, 2004, 101:511-517.
Lee et al., "Effect of High-Frequency Stimulation of the Subthalamic Nucleus on Subthalamic Neurons: An Intracellular Study," *Stereotactic. Funct. Neurasurg.*, 2003, 80:32-36.
Limberger et al., "'Real time' measurement of endogenous dopamine release during short trains of pulses in slices of rat neostriatum and nucleus accumbens: role of autoinhibition," *Naunyn-Schmiedeberg's Arch Pharmacol.*, 1991, 344:623-629.
Limousin et al., "Electrical stimulation of the subthalamic nucleus in advanced Parkinson's disease," *N Engl J Med*, 1998, 339:1105-1111.
Lind et al., "Mapping the amphetamine-evoked dopamine release in the brain of the Göttingen mimpig," *Brain Res Bull.*, 2005, 65:1-9.
Lind et al., "The use of pigs in neuroscience: modeling brain disorders," *Neurosci Biobehav Rev*, 2007, 31(5):728-51.
Littlewood et al., "Mapping the central effects of ketamine in the rat using pharmacological MRI," *Psychopharmacology (Berl)*, 2006, 186:64-81.
Llaudet et al., "A three-enzyme microelectrode sensor for detecting purine release from central nervous system," *Biosens Bioelectron.*, 2003, 18:43-52.
Logothetis et al., "Neurophysiological investigation of the basis of the fMRI signal," *Nature*, 2001, 412:150-157.
Lowry and Fillenz, "Real-time monitoring of brain energy metabolism in vivo using microelectrochemical sensors: the effects of anesthesia," *Bioelectrochem.*, 2001, 54:39-47.
Lowry eta l., "An amperometric glucose-oxidase/poly(o-phenylenediamine) biosensor for monitoring brain extracellular glucose: in vivo characterization in the striatum of freely-moving rats," *J Neurosci Methods*, 1998, 79:65-74.
Lozano et al., "Subcallosal cingulate gyms deep brain stimulation for treatment-resistant depression," *Biol Psychiatry*, 2008, 64:461-467.
Maarrawi et al., "Motor cortex stimulation for pain control induces changes in the endogenous opioid system," *Neurol.*, 2007, 69:827-834.
Macmillan et al., "Accuracy of a miniature intracranial pressure monitor, its function during magnetic resonance scanning, and assessment of image artifact generation," *Neurosurgery*, 1999, 45:188-192.
Mandelkow et al., "Synchronization facilitates removal of MRI artefacts from concurrent EEG recordings and increases usable bandwidth," *Neuroimage*, 2006, 32-1120-1126.
Mayberg et al., "Deep brain stimulation for treatment-resistant depression," *Neuron*, 2005, 45:651-660.
Mazzone et al., "Implantation of human pedunculopontine nucleus: a safe and clinically relevant target in Parkinson's disease," *Neuroreport*, 2005, 16:1877-1881.

(56) References Cited

OTHER PUBLICATIONS

McIntyre et al., "Uncovering the mechanism(s) of action of deep brain stimulation: activation, inhibition, or both," *Clin Neurophysiol.*, 2004, 115:1239-1248.
Meissner et al., "Deep brain stimulation in late stage Parkinson's disease: a retrospective cost analysis in Germany," *J Neurol.* 2005, 252:218-223.
Meissner et al., "Deep brain stimulation of subthalamic neurons increases striatal dopamine metabolism and induces contralateral circling in freely moving 6-hydroxydopamine-lesioned rats," *Neurosci Lett.*, 2002, 328:105-108.
Meissner et al., "Striatal dopaminergic metabolism is increased by deep brain stimulation of the subthalamic nucleus in 6-hydroxydopamine lesioned rats," *Neurosci Lett.*, 2001, 303:165-168.
Meltzer et al., "Modulation of dopamine neuronal activity by glutamate receptor subtypes," *Neurosci. Biobehav. Rev.*, 1997, 21:511-518.
Menon et al., "Combined event-related fMRI and EEG evidence for temporal-parietal cortex activation during target detection," *Neuroreport*, 1997, 8:3029-3037.
Michael et al., "Improving data acquisition for fast-scan cyclic voltammetry," *Anal Chem.*, 1999, 71(18):3941-3947.
Mikkelsen et al., "MPTP-induced Parkinsonism in minipigs: A behavioral, biochemical, and histological study," *Neurotoxicol Teratol*, 1999, 21(2):169-75.
Mitchell, "Acetylcholine and choline amperometric enzyme sensors characterized in vitro and in vivo," *Anal Chem.*, 2004, 76:1098-106.
Molina et al., "Additive Differential pulse voltammetry, instead of double differential pulse voltammetry," *Electrochem. Commun.*, 2001, 3:324-329.
Molinuevo et al., "Levodopa withdrawal after bilateral subthalamic nucleus stimulation in advanced Parkinson disease," *Arch Neurol.*, 2000, 57:983-988.
Moro et al., "Chronic subthalamic nucleus stimulation reduces medication requirements in Parkinson's disease," *Neurol.*, 1999, 53:85-90.
Moro et al., "The Impact on Parkinson's disease of electrical parameter settings in STN stimulation," *Neurology*, 2002, 59:706-713.
Moyer et al., "Effects of dopaminergic modulation on the integrative properties of the ventral striatal medium spiny neuron," *J Neurophysiol.*, 2007, 98:3731-3748.
Nandi et al., "Exploration of the role of the upper brainstem in motor control," *Stereotact Funct Neurosurg*, 2002, 78(3-4):158-167
Naylor et al., "A new technique for the simultaneous recording of electroencephalograph activity and CNS biosensor data," in Phillips PEM, Sandberg SG, Ahn S, Phillips AG (ed): proceeding of the 12th international conference on in vivo methods 2008. University of British Columbia, Vancouver, Canada. 2008, pp. 127-129.
Netchiporouk et al., "Brain extracellular glucose assessed by voltammetry throughout the rat sleep-wake cycle," *Eur J Neurosci.*, 2001, 13:1429-1434.
Niazy et al., "Removal of FMRI environment artifacts from EEG data using optimal basis sets," *Neuroimage*, 2005, 28:720-737.
Nomoto et al., "The metabolic rate and vulnerability of dopaminergic neurons, and adenosine dynamics in the cerebral cortex, nucleus accumbens, caudate nucleus, and putamen of the common marmoset," *J Neural.*, 2000, 247:16-22.
Norris, "Principles of magnetic resonance assessment of brain function," *J Magn Reson Imaging*, 2006, 23:794-807.
Patel et al., "Unilateral subthalamotomy in the treatment of Parkinson's disease," *Brain*, 2003, 126:1136-1145.
Paul et al., "High frequency stimulation of the subthalamic nucleus influences striatal dopaminergic metabolism in the naive rat," *Neuroreport*, 2000, 11:441-444.
Perea and Araque, "Astrocytes potentiate transmitter release at single hippocampal synapses," *Science*, 2007, 317:1083-1086.
Phillips et al., "Parkinson disease: pattern of functional MR imaging activation during deep brain stimulation of subthalamic nucleus—initial experience," *Radiology*, 2006, 239:209-216.
Pohlmeyer et al., "Toward the Restoration of Hand Use to a Paralyzed Monkey: Brain-Controlled Functional Electrical Stimulation of Forearm Muscles," *PLoS One*, 2009, 4(6):1-8.
Pomerleau et al., "Real time in vivo measures of L-glutamate in the rat central nervous system using ceramic-based multisite microelectrode arrays," *Ann N Y Acad Sci.*, 2003, 1003:454-7.
Priori et al., "Do intraoperative microrecordings improve subthalamic nucleus targeting in stereotactic neurosurgery for Parkinson's disease?" *J Neurosurg Sci.*, 2003, 47:56-60.
Purdon et al., "An open-source hardware and software system for acquisition and real-time processing of electrophysiology during high field MRI," *J Neurosci Methods*, 2008, 175:165-186.
Purdon et al., "Simultaneous electroencephalography and functional magnetic resonance imaging of general anesthesia," *Ann N Y Acad Sci.*, 2009, 1157:61-70.
Rehncrona et al., "Long-term efficacy of thalamic deep brain stimulation for tremor: double-blind assessments," *Mov Disord.*, 2003, 18:163-170.
Ren et al., "Dopaminergic response to graded dopamine concentration elicited by four amphetamine doses," *Synapse*, 2009, 63:764-772.
Roberts and Mikulis, "Neuro MR: principles," *J Magn Reson Imaging*, 2007, 26:823-837.
Robinson et al., "Monitoring rapid chemical communication in the brain," *Chem Rev.*, 2008, 108:2554-2584.
Robinson et al., "Detecting Subsecond Dopamine Release with Fast-Scan Cyclic Voltammetry in Vivo," *Clin. Chem.*, 2003, 49:1763-1773.
Roham et al., "Diamond microelectrodes and CMOS microelectronics for wireless transmission of fast-scan cyclic voltammetry," *Conf Proc IEEE Eng Med Biol Soc*, 2007. 2007::6044-7.
Saint-Cyr et al., "Localization of clinically effective stimulating electrodes in the human subthalamic nucleus on magnetic resonance imaging," *J. Neurosurg.*, 2002, 97:1152-1166.
Sandberg and Garris, "Neurochemistry of addiction: monitoring essential neurotransmitters of addiction," in Koob GF, Kuhn C (ed): Novel Approaches to Addiction Boca Raton: CRC Press, 2010, 30 pages.
Saunders et al., "Microdialysis in nonhuman Primates," *Curr Protoc Neurosci*, 2001, Chapter 7:Unit7, 20 pages.
Schwarz et al., "Concurrent pharmacological MRI and in situ microdialysis of cocaine reveal relationship between the central hemodynamic response and local dopamine concentration," *Neuroimage*, 2004, 23:296-304.
Shastry, "Parkinson disease: etiology, pathogenesis and future of gene therapy," *Neurosci. Res.*, 2001, 41:5-12.
Shimo and Wichmann, "Neuronal activity in the subthalamic nucleus modulates the release of dopamine in the monkey striatum," *Eur. J Neurosci.*, 2009, 29:104-113.
Shon et al., "Comonitoring of adenosine and dopamine using the Wireless Instantaneous Neurotransmitter Concentration System: proof of principle: Laboratory investigation," *J Neurosurg.*, 2010, 112(3):539-548.
Stefurak et al., "Deep brain stimulation for Parkinson's disease dissociates mood and motor circuits: a functional MRI case study," *Mov Disord*, 2003, 18:1508-1516.
Suaud-Chagny et al., "Uptake of dopamine released by impulse flow in the rat mesolimbic and striatal systems in vivo," *J Neurochem.*, 1995, 65:2603-2611.
Suaud-Chagny, "In vivo monitoring of dopamine overflow in the central nervous system by amperometric techniques combined with carbon fibre electrodes," *Methods.*, 2004, 33:322-329.
Swamy et al., "Subsecond Detection of Physiological Adenosine Concentrations Using Fast-Scan Cyclic Voltammetry," *Anal. Chem.*, 2007, 79:744-750.
Tawfik et al., "Deep Brain Stimulation Results in Local Glutamate and Adenosine Release" Investigation into the Role of Astrocytes, *Neurosurgery*, 2010, 67:367-75.

(56) References Cited

OTHER PUBLICATIONS

Thobois et al., "Chronic subthalamic nucleus stimulation and striatal D2 dopamine receptors in Parkinson's disease—A [(11)C]-raclopride PET study," *J Neurol.*, 2003, 250:1219-1223.

Tsubokawa et al., "Chronic motor cortex stimulation for the treatment of central pain," *Acta Neurochir Suppl (Wien)*, 1991, 52:137-139

Tsubokawa et al., "Chronic motor cortex stimulation in patients with thalamic pain," *J Neurosurg.*, 1993, 78:393-401.

van der Zeyden et al., "Microdialysis of GABA and glutamate: analysis, interpretation and comparison with microsensors," *Pharmacol Biochem Behav.*, 2008, 90:135-147.

Venton et al., "Real-time decoding of dopamine concentration changes in the caudate-putamen during tonic and phasic firing," *J Neurochem*, 2003, 87:1284-1295.

Voges et al., "Bilateral high-frequency stimulation in the subthalamic nucleus for the treatment of Parkinson disease: correlation of therapeutic effect with anatomical electrode position," *J. Neurosurg.*, 2002, 96:269-279.

Volkmann, "Deep brain stimulation for the treatment of Parkinson's disease," *J Clin Neurophysiol.*, 2004, 21:6-17.

Watson et al., "In vivo measurements of neurotransmitters by microdialysis sampling," *Anal Chem*, 2006, 78:1391-1399.

Welter et al., "Effects of high-frequency stimulation on subthalamic neuronal activity in parkinsonian patients," *Arch Neurol.*, 2004, 61:89-96.

Wiedemann et al., "Strategies for Low Detection Limit Measurements with Cyclic Voltammetry," *Anal. Chem.*, 1991, 63:2965-2970.

Wightman et al., "Temporally resolved catecholamine spikes correspond to single vesicle release from individual chromaffin cells," *Proc Natl Acad Sci USA*, 1991, 88:10754-10758.

Williams and Millar, "Concentration-dependent actions of stimulated dopamine release on neuronal activity in rat striatum," *Neuroscience*, 1990, 39(1):1-16.

Williams and Millar, "Differential Actions of Endogenous and Iontophoretic Dopamine in Rat Striatum," *Eur J Neurosci*, 1990, 2(7):658-661.

Wilson and Gifford, "Biosensors for real-time in vivo measurements," *Biosens Bioelectron.*, 2005, 20:2388-2403.

Windels et al., "Effects of high frequency stimulation of subthalamic glutamate and GABA in substantia nigra and globus pallidus in the normal rat," *Eur J Neurosci.*, 2000, 12:4141-4146.

Wu et al., "Determination of release and uptake parameters from electrically evoked dopamine dynamics measured by real-time voltammetry," *J Neurosci Methods*, 2001, 112:119-133.

Zhao et al., "Long term high frequency stimulation of STN increases dopamine in the corpus striatum of hemiparkinsonian rhesus monkey," *Brain Res.*, 2009, 1286:230-238.

International Preliminary Report on Patentability for PCT/US2014/010882, mailed Jul. 23, 2015, 6 pages.

Office Action in U.S. Appl. No. 13/555,965, mailed Aug. 13, 2015, 9 pages.

Office Action in U.S. Appl. No. 14/760,011, mailed Dec. 4, 2015, 9 pages.

Office Action in U.S. Appl. No. 14/760,011, dated Jun. 16, 2016, 8 pages.

International Preliminary Report on Patentability for PCT/US2014/050550, mailed Feb. 18, 2016, 6 pages.

\* cited by examiner

Figure 5
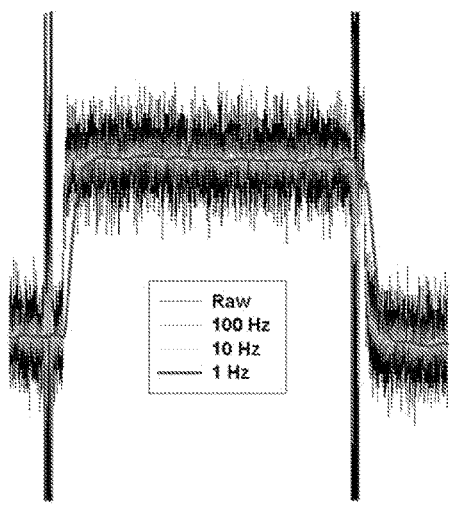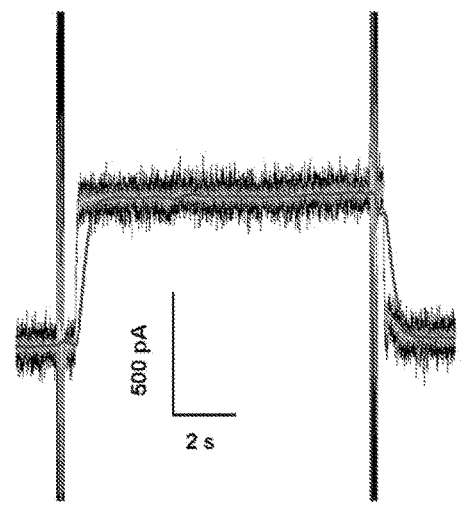

Figure 17
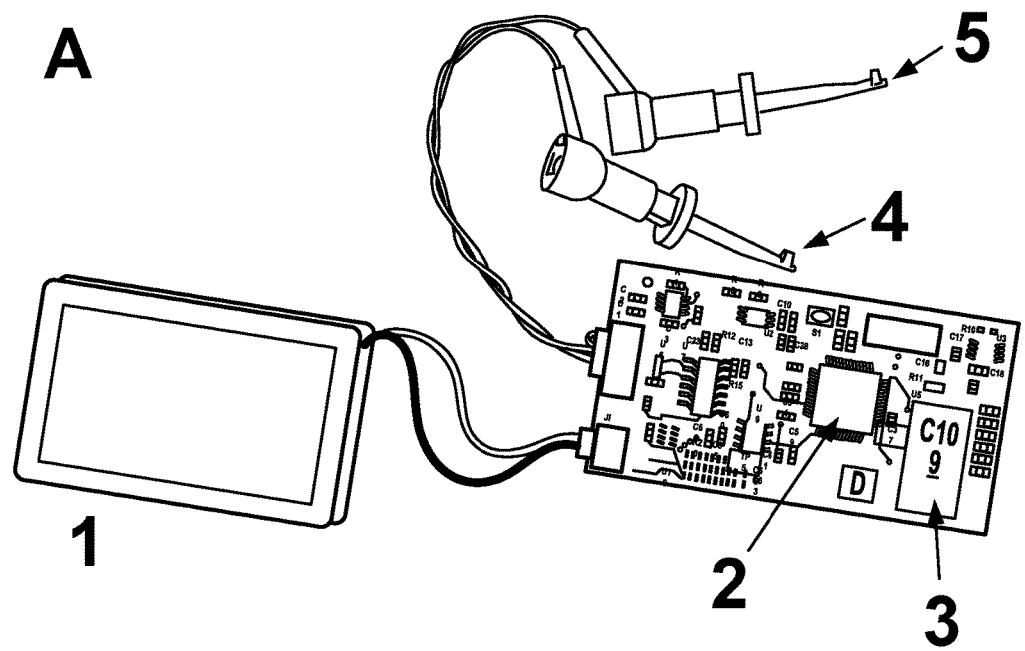
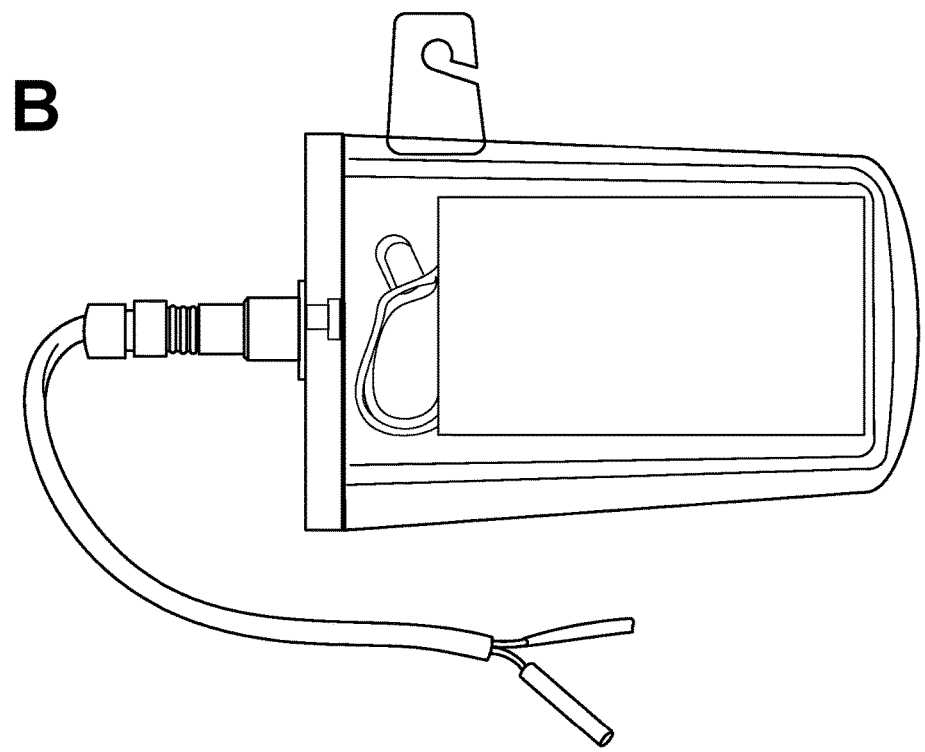

Figure 21
DBS Induced Adenosine Release
Different Intensities of Stimulation
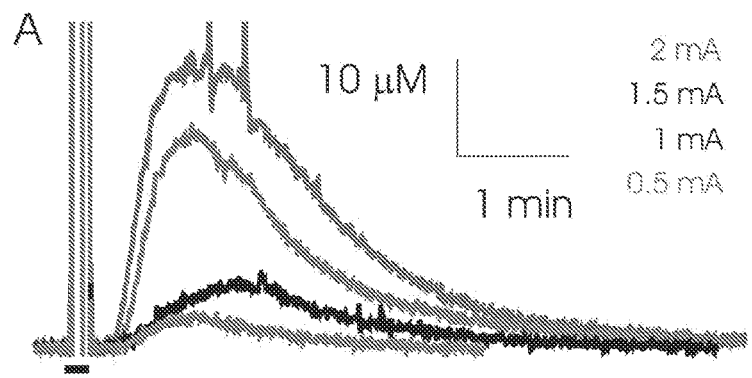
Different Frequencies of Stimulation
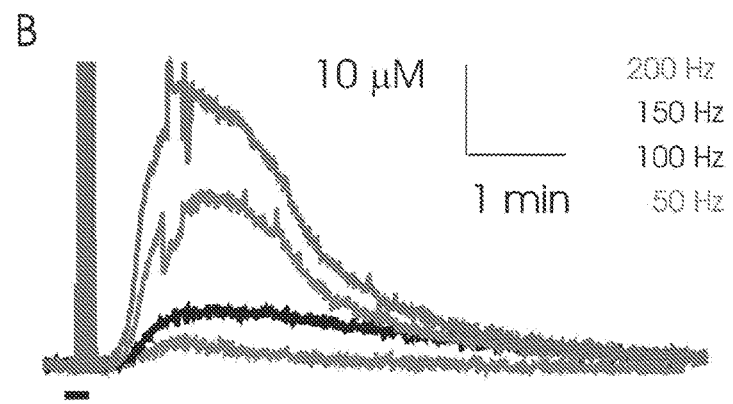

Figure 22
Glutamate release during 1 mA HFS
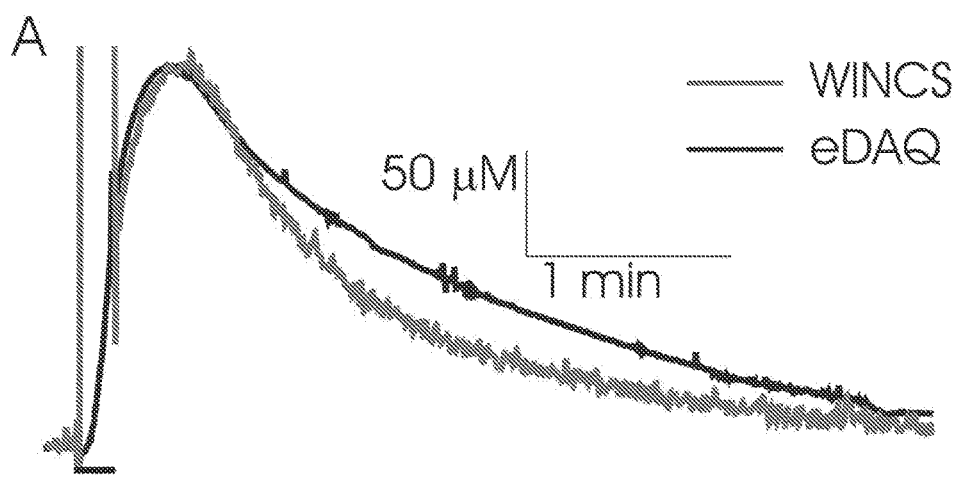
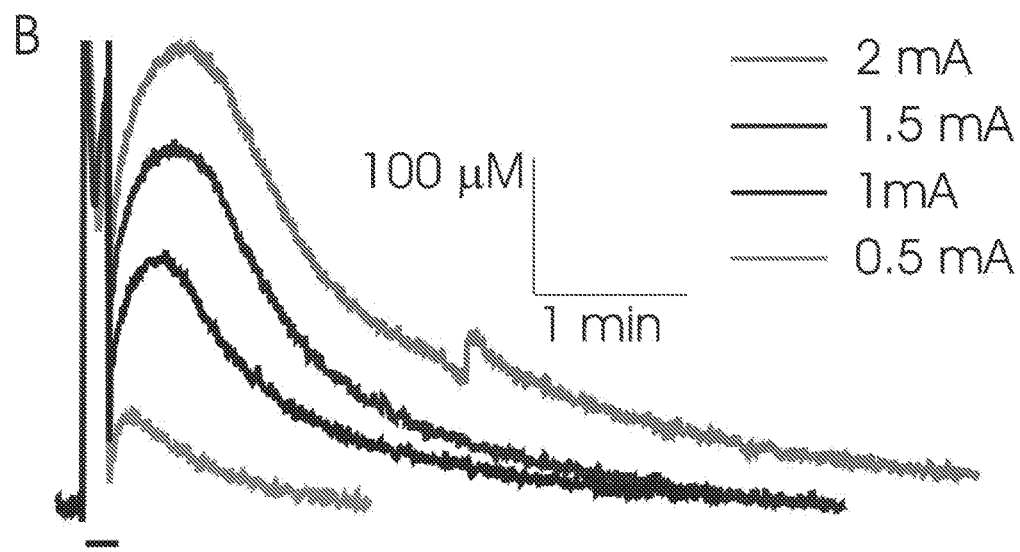

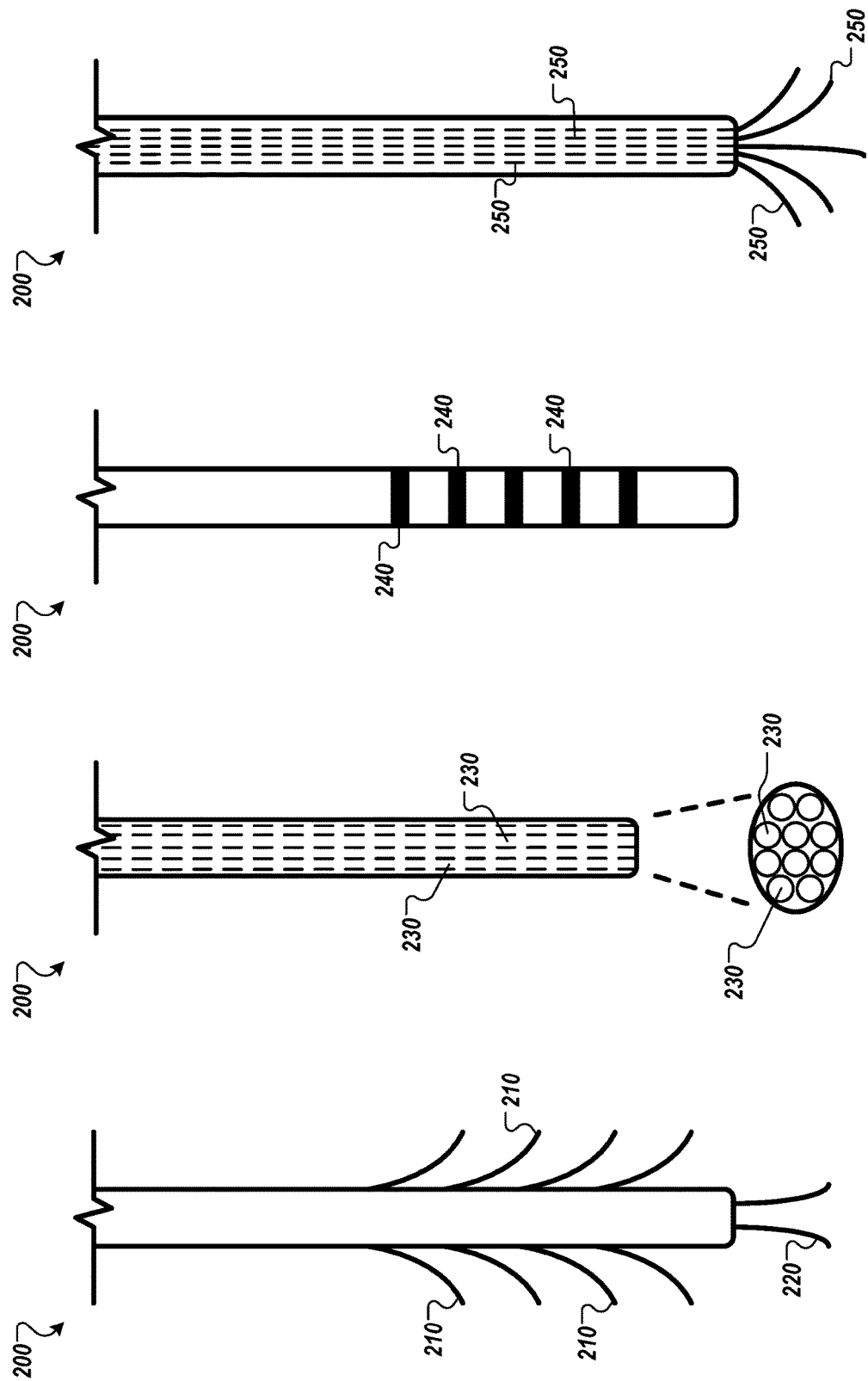

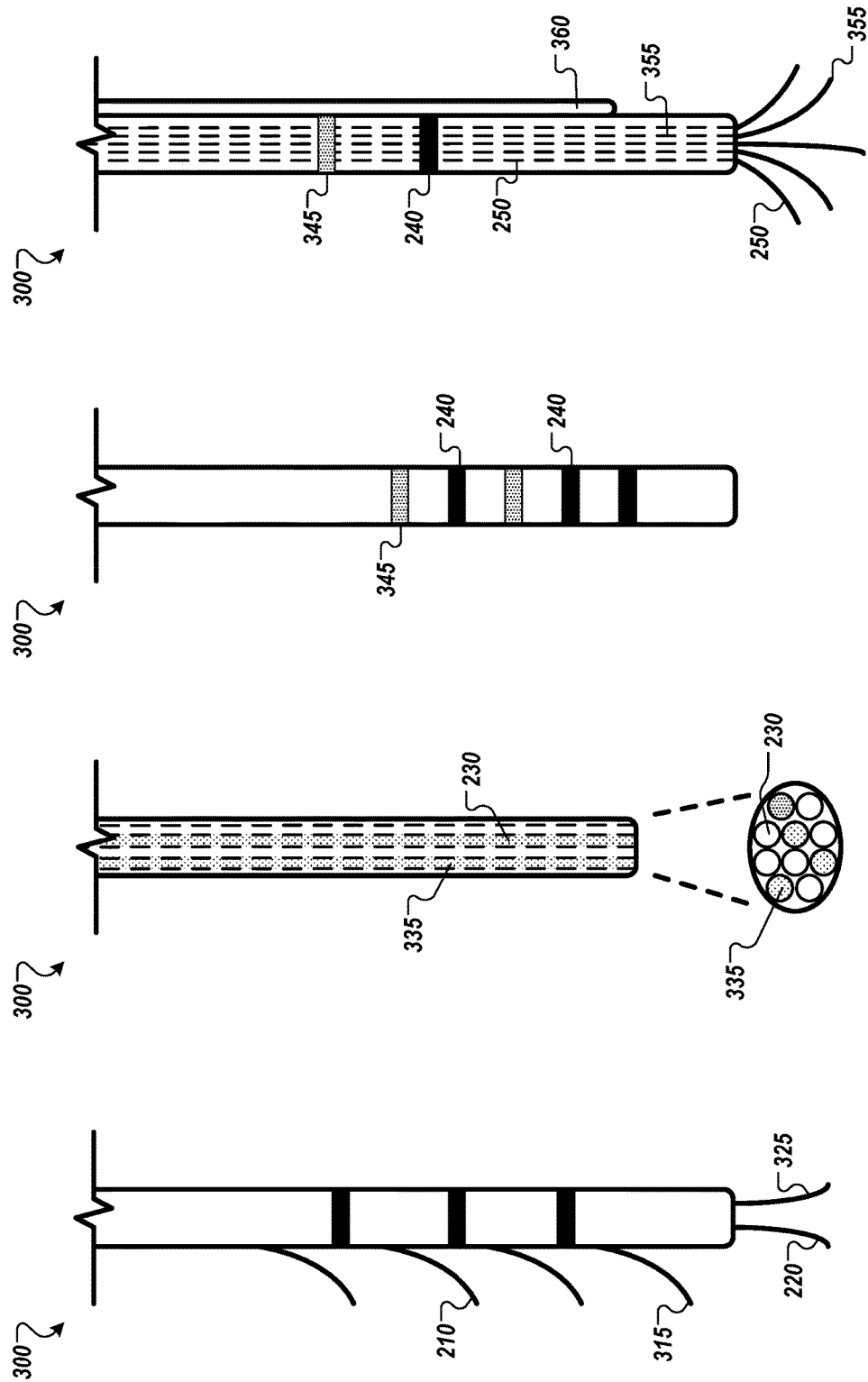

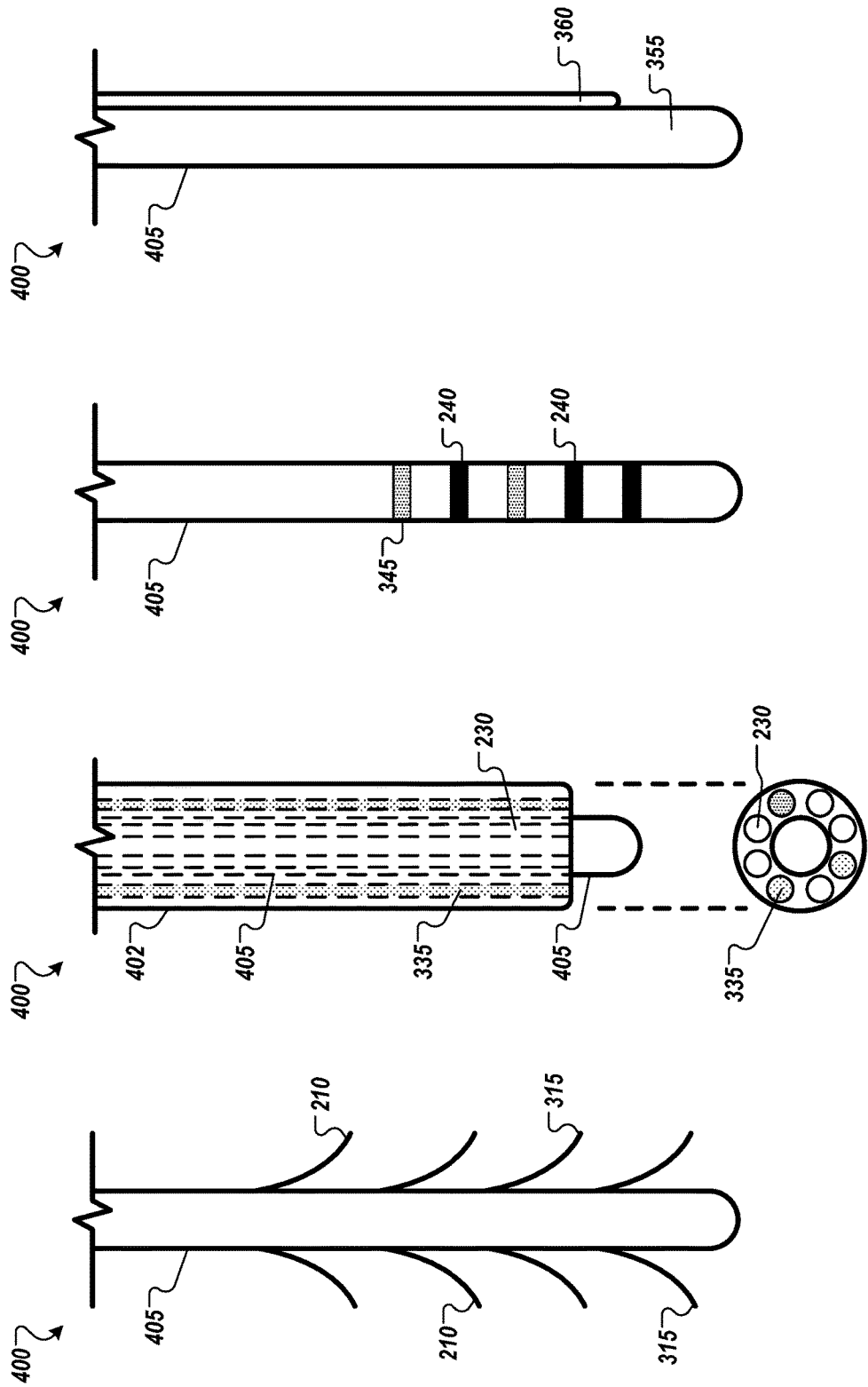

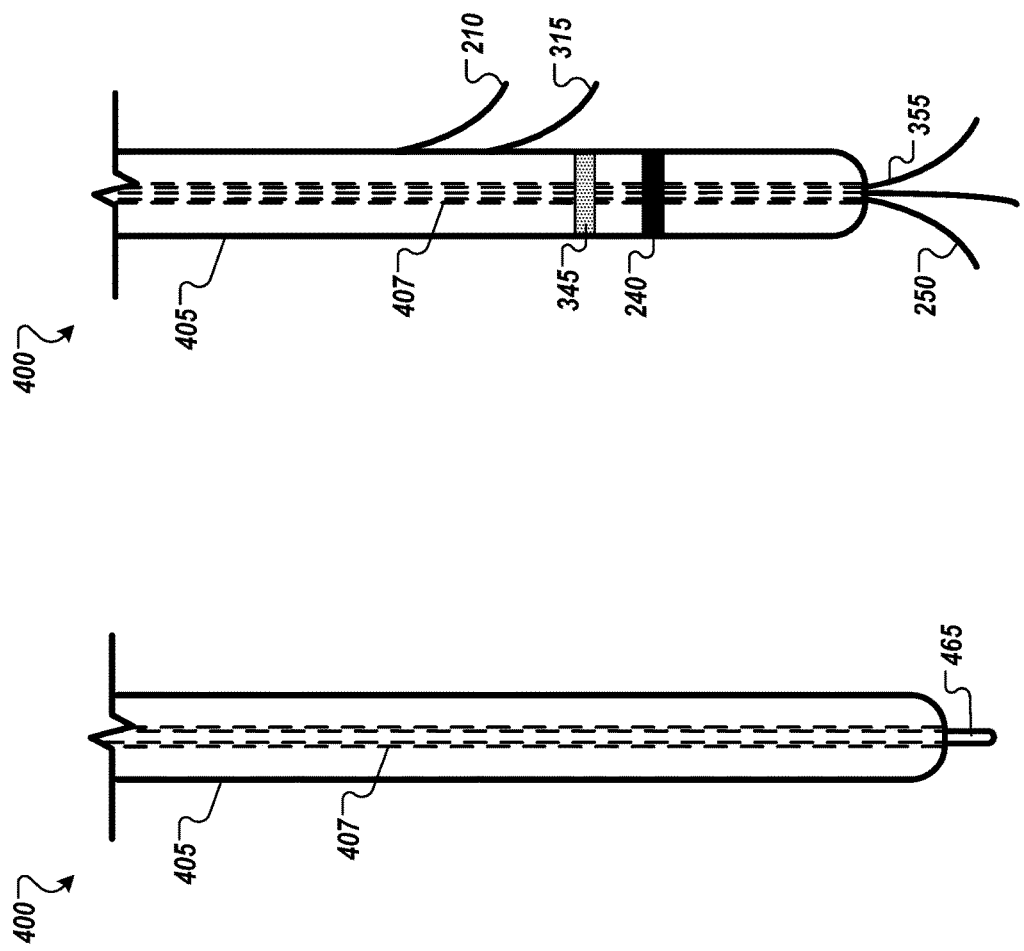

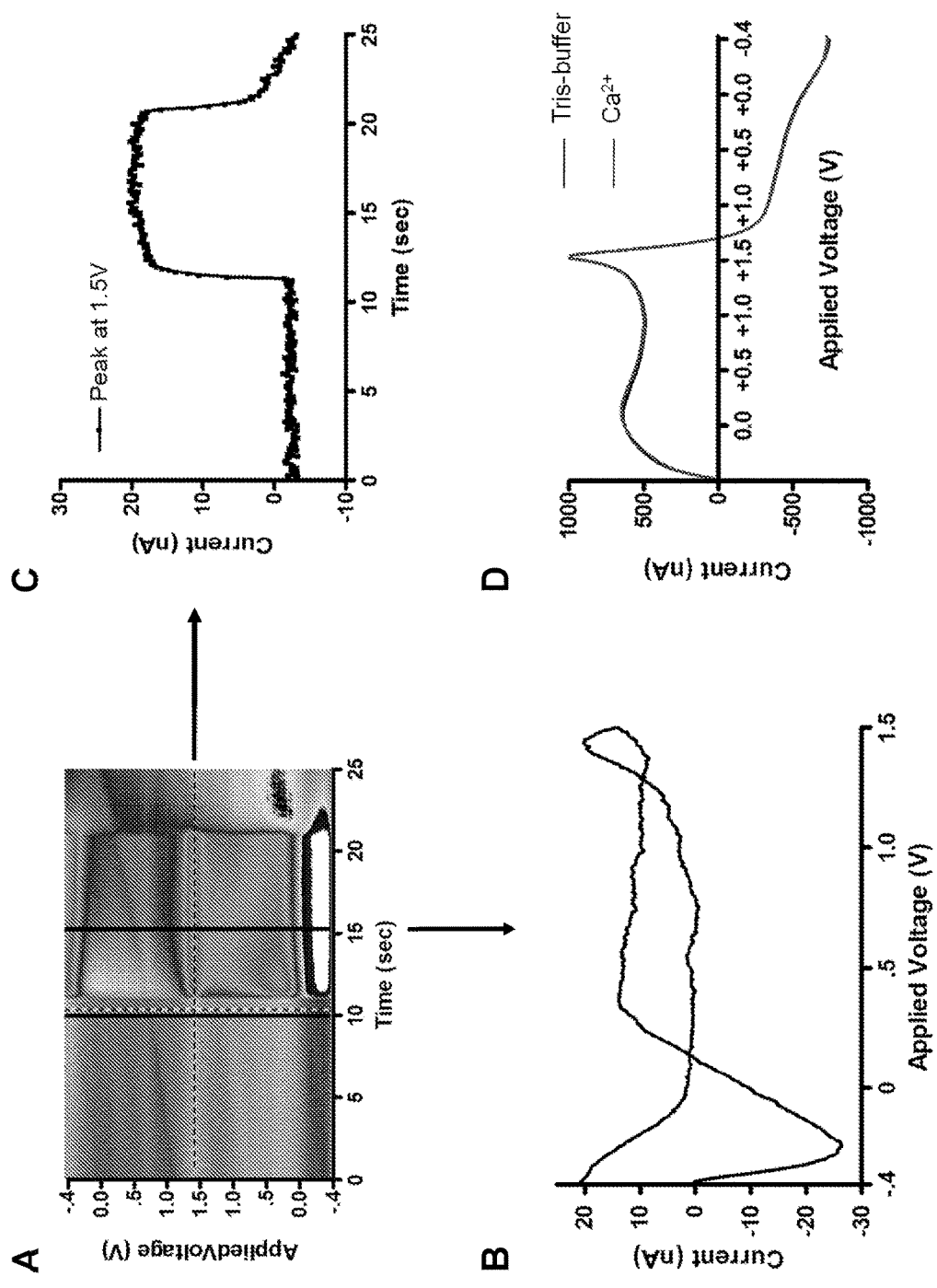
Figure 28 (Ca$^{2+}$ 2mM)

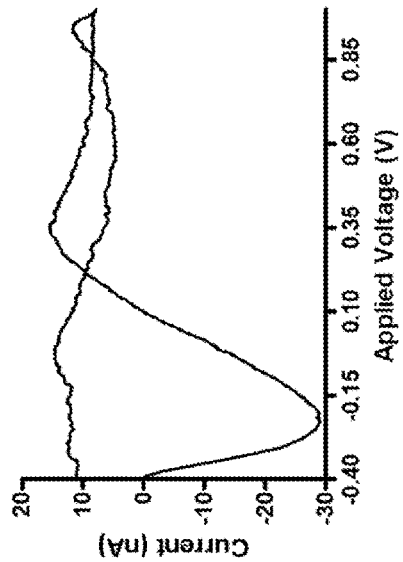
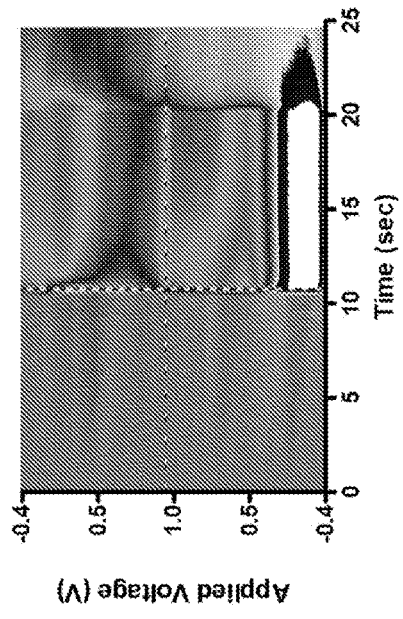
Figure 28 continued (Ca$^{2+}$ 2mM -0.4V to 1.0V)

Figure 29 ($Ca^{2+}$)
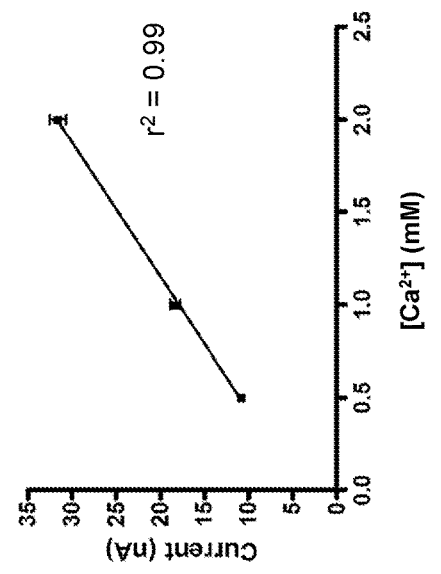
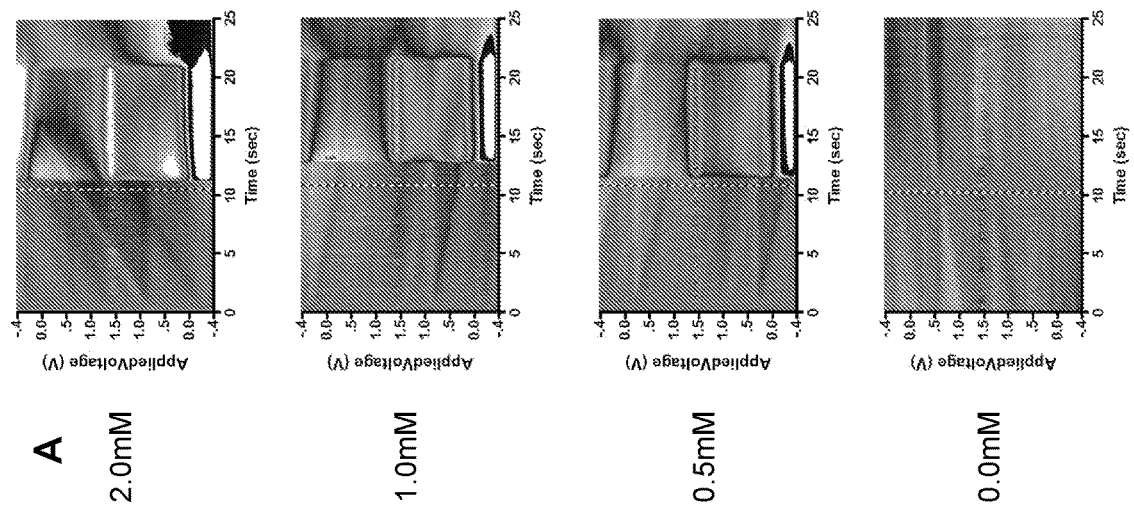

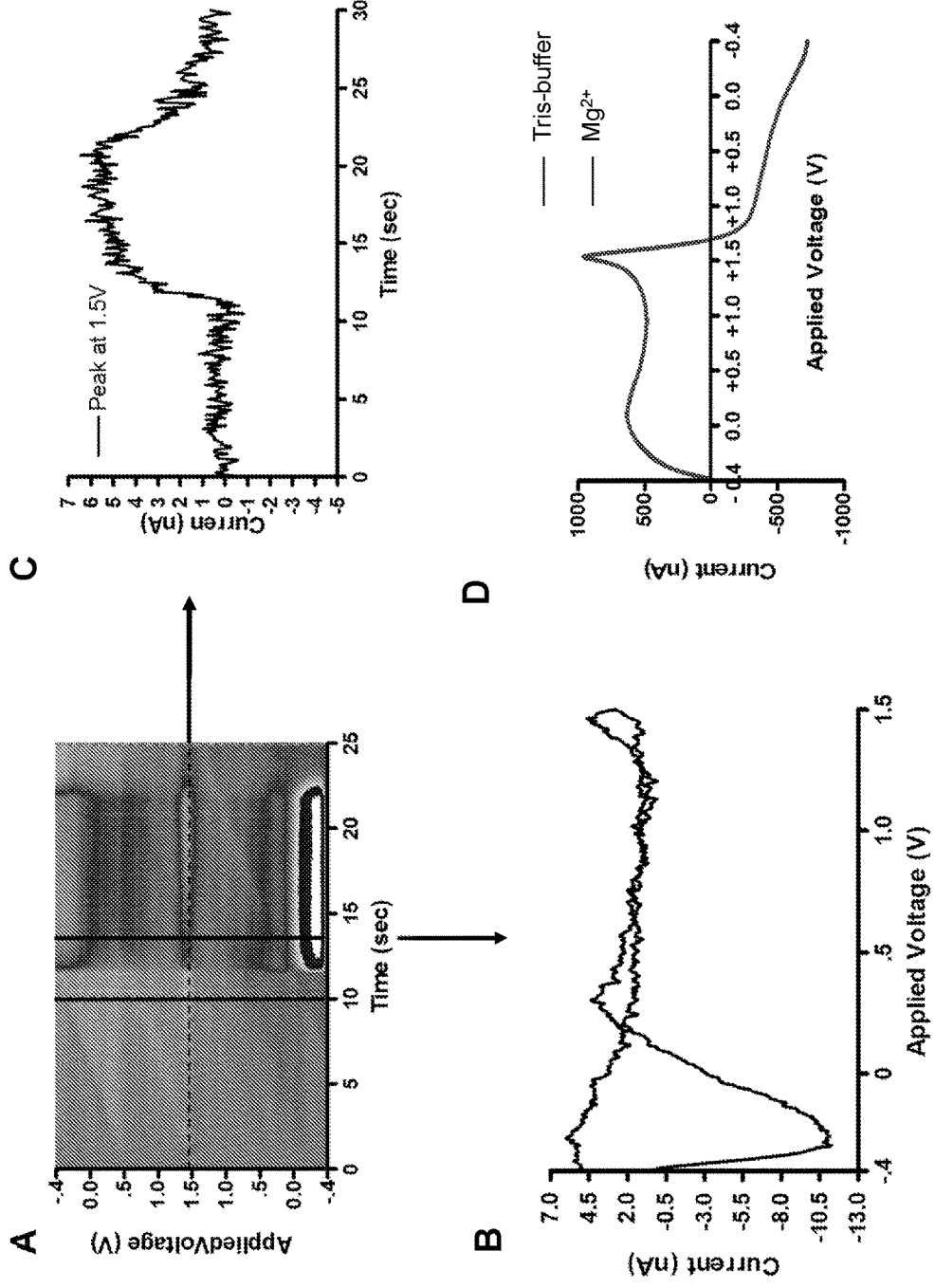
Figure 30 (Mg²⁺ 1mM)

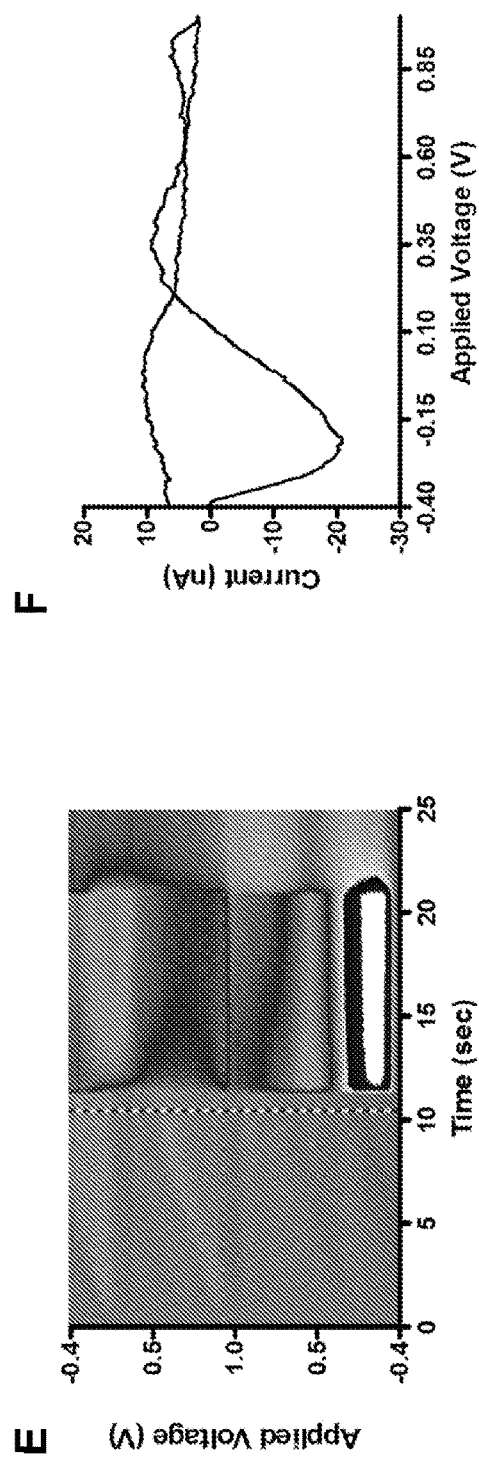
Figure 30 continued (Mg²⁺ 1mM -0.4V to 1.0V)

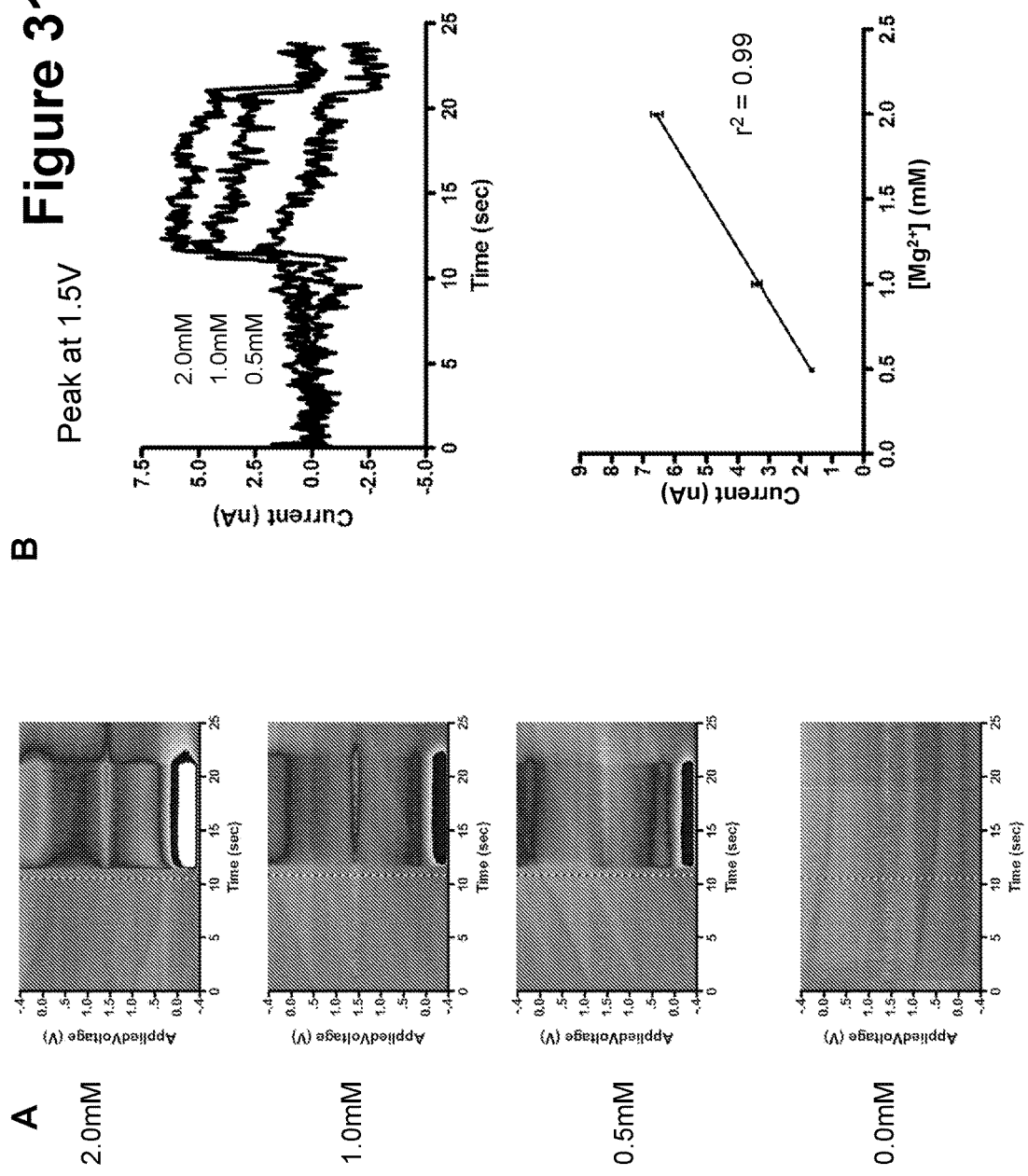
Figure 31 (Mg$^{2+}$)

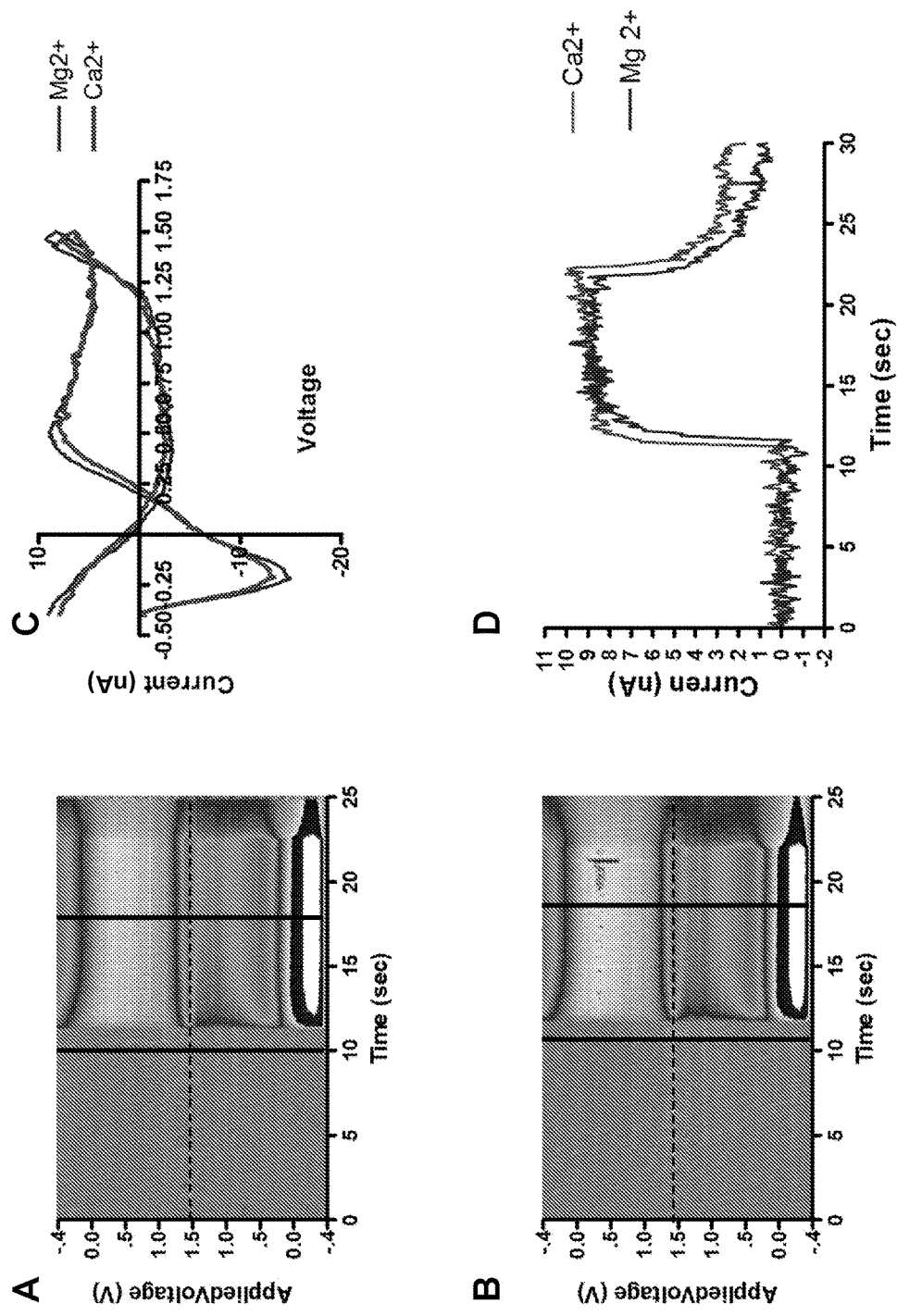

DETECTING NEUROCHEMICAL OR ELECTRICAL SIGNALS WITHIN BRAIN TISSUE

CROSS REFERENCE TO RELATED APPLICATIONS

This application is a National Stage application under 35 U.S.C. 371 and claims benefit under 35 U.S.C. 119(a) of International Application No. PCT/US2010/046807, having an International Filing Date of Aug. 26, 2010, which claims the benefit of U.S. Provisional Application Ser. No. 61/275, 168, filed Aug. 26, 2009. The disclosure of the prior applications are considered part of (and are incorporated by reference in) the disclosure of this application.

STATEMENT AS TO FEDERALLY SPONSORED RESEARCH

This invention was made with government support under grant number NS052232 awarded by National Institutes of Health. The government has certain rights in the invention.

BACKGROUND

1. Technical Field

This document relates to methods and materials involved in detecting neurochemical signals, electrophysiological signals, ions, or combinations thereof within brain tissue. For example, the document relates to methods and materials for using probes to detect neurochemical signals (e.g., neurotransmitter concentrations), electrical signals, ions, or combinations thereof during deep brain stimulation or during physiologic activity.

2. Background Information

Deep brain stimulation (DBS) surgery is a state-of-the-art neurosurgical intervention procedure currently used to treat single or multiple disorders, including Parkinson's disease (PD), tremor, dystonia, depression, and chronic pain. Although this procedure has gained rapid popularity for tremor and related dysfunctions and its remarkable therapeutic efficacy, the precise mechanism of action remains unknown. Several theories have been proposed to account for the therapeutic action of DBS, some of which are based on the stimulation evoked release of neurotransmitters such as dopamine, glutamate, GABA, and adenosine from proximal and distal brain nuclei.

SUMMARY

This document relates to methods and materials involved in detecting neurochemical signals, electrophysiological signals, ions, or combinations thereof within brain tissue. For example, the document relates to methods and materials for using active and passive probes to detect neurochemical signals (e.g., neurotransmitter concentrations), electrical signals, ions (e.g., calcium, magnesium, sodium, potassium, or other divalent metal ions), or combinations thereof during deep brain stimulation.

In general, one aspect of this document features a probe comprising, or consisting essentially of, a first sensor having the ability to detect a first neurochemical and a second sensor having the ability to detect a second neurochemical. The first and second neurochemicals are selected from the group consisting of dopamine, serotonin, adenosine, adenine mono- or tri-phosphate, norepinephrine, GABA, histamine, acetylcholine, glutamate, aspartate, epinephrine, nitric oxide, glycine, tryptamine, phenylethylamine, tyramine, and octopamine. The probe can comprise a sensor having the ability to detect dopamine, a sensor having the ability to detect serotonin, a sensor having the ability to detect adenosine, a sensor having the ability to detect norepinephrine, a sensor having the ability to detect GABA, a sensor having the ability to detect histamine, a sensor having the ability to detect acetylcholine, and a sensor having the ability to detect glutamate. The probe can comprise a sensor having the ability to detect pH. The probe can comprise an electrode capable of applying an electrical stimulus to brain tissue in a mammal. The probe can comprise an electrode capable of applying an electrical stimulus to the medial forebrain bundle of a brain of a mammal, wherein the electrical stimulus comprises a continuous or intermittent electrical stimulation. The probe can comprise a control unit. The probe can comprise a device capable of transmitting information to a processing unit. The probe can comprise a device capable of wirelessly transmitting information to a processing unit. The probe can comprise a device capable of receiving information from a processing unit. The probe can comprise a device capable of wirelessly receiving information from a processing unit.

In another aspect, this document features a deep brain stimulation system comprising, or consisting essentially of: (a) a probe comprising a sensor having capable of detecting a neurochemical and an electrode capable of applying an electrical stimulus to brain tissue, and (b) a processing unit in wireless communication with the probe, wherein the processing unit is capable of receiving information from the probe about the level of the neurochemical and is capable of sending information to the probe about the level or timing of electrical stimulus to deliver to the brain tissue. The neurochemical can be selected from the group consisting of dopamine, serotonin, adenosine, adenine mono- or tri-phosphate, norepinephrine, GABA, histamine, acetylcholine, glutamate, aspartate, epinephrine, nitric oxide, glycine, tryptamine, phenylethylamine, tyramine, and octopamine. The probe can comprise two or more sensors, wherein one of the two or more sensors is capable of detecting a first neurochemical, and another of the two or more sensors is capable of detecting a second neurochemical. The probe can comprise a sensor having the ability to detect dopamine, a sensor having the ability to detect, a sensor having the ability to detect serotonin, a sensor having the ability to detect adenosine, a sensor having the ability to detect norepinephrine, a sensor having the ability to detect GABA, a sensor having the ability to detect histamine, a sensor having the ability to detect acetylcholine, and a sensor having the ability to detect glutamate. The probe can comprise a sensor having the ability to detect pH. The probe can comprise a sensor having the ability to detect electrical brain signals.

In another aspect, this document features a deep brain stimulation system comprising, or consisting essentially of: (a) a probe comprising a sensor having capable of detecting a neurochemical and an electrode capable of applying an electrical stimulus to brain tissue, and (b) a control unit in communication with the probe, wherein the control unit is capable of receiving information from the probe about the level of the neurochemical and is capable of sending information to the probe about the level or timing of electrical stimulus to deliver to the brain tissue. The neurochemical can be selected from the group consisting of dopamine, serotonin, adenosine, adenine mono- or tri-phosphate, norepinephrine, GABA, histamine, acetylcholine, glutamate, aspartate, epinephrine, nitric oxide, glycine, tryptamine, phenylethylamine, tyramine, and octopamine. The probe can comprise two or more sensors, wherein one of the two or more sensors is capable of detecting a first neurochemical, and another of the two or more sensors is capable of detecting a second neurochemical. The probe can comprise a sensor having the ability to detect dopamine, a sensor having the ability to detect, a sensor having the ability to detect serotonin, a sensor having the ability to detect adenosine, a sensor having the ability to detect norepinephrine, a sensor having the ability to detect GABA, a sensor having the ability to detect histamine, a sensor having the ability to detect acetylcholine, and a sensor having the ability to detect glutamate. The probe can comprise a sensor having the ability to detect pH. The probe can comprise a sensor having the ability to detect electrical brain signals. The probe and the control unit can be connected.

In another aspect, this document features a probe comprising, or consisting essentially of, a first sensor having the ability to detect a first ion and a second sensor having the ability to detect a second ion, wherein the first and second ions are selected from the group consisting of calcium, magnesium, sodium, potassium, protons, iron, copper, chromium, lead, mercury, cobalt, gold, lithium, cesium, barium, zinc, chloride, bicarbonate, phosphate, bromide, iodide, sulfide, oxide, sulfide, and fluoride.

In another aspect, this document features a deep brain stimulation system comprising, or consisting essentially of, (a) a probe comprising a sensor capable of detecting a neurochemical or an ion and an electrode capable of applying an electrical stimulus to brain tissue, and (b) a processing unit in wireless communication with the probe, wherein the processing unit is capable of receiving information from the probe about the level of the neurochemical and is capable of sending information to the probe about the level or timing of electrical stimulus to deliver to the brain tissue. The sensor can be capable of detecting the neurochemical, and the neurochemical can be selected from the group consisting of dopamine, serotonin, adenosine, adenine mono- or tri-phosphate, norepinephrine, GABA, histamine, acetylcholine, glutamate, aspartate, epinephrine, nitric oxide, glycine, tryptamine, phenylethylamine, tyramine, and octopamine. The sensor can be capable of detecting the ion, and the ion can be selected from the group consisting of calcium, magnesium, sodium, potassium, protons, iron, copper, chromium, lead, mercury, cobalt, gold, lithium, cesium, barium, zinc, chloride, bicarbonate, phosphate, bromide, iodide, sulfide, oxide, sulfide, and fluoride. The probe can comprise two or more sensors, wherein one of the two or more sensors is capable of detecting a first neurochemical or ion, and another of the two or more sensors is capable of detecting a second neurochemical or ion. The probe can comprise a sensor having the ability to detect dopamine, a sensor having the ability to detect, a sensor having the ability to detect serotonin, a sensor having the ability to detect adenosine, a sensor having the ability to detect norepinephrine, a sensor having the ability to detect GABA, a sensor having the ability to detect histamine, a sensor having the ability to detect acetylcholine, and a sensor having the ability to detect glutamate. The probe can comprise a sensor having the ability to detect pH. The probe can comprise a sensor having the ability to detect electrical brain signals.

In another aspect, this document features a deep brain stimulation system comprising, or consisting essentially of, (a) a probe comprising a sensor capable of detecting a neurochemical or an ion and an electrode capable of applying an electrical stimulus to brain tissue, and (b) a control unit in communication with the probe, wherein the control unit is capable of receiving information from the probe about the level of the neurochemical and is capable of sending information to the probe about the level or timing of electrical stimulus to deliver to the brain tissue. The sensor can be capable of detecting the neurochemical, and wherein the neurochemical can be selected from the group consisting of dopamine, serotonin, adenosine, adenine mono- or tri-phosphate, norepinephrine, GABA, histamine, acetylcholine, glutamate, aspartate, epinephrine, nitric oxide, glycine, tryptamine, phenylethylamine, tyramine, and octopamine. The sensor can be capable of detecting the ion, and the ion can be selected from the group consisting of calcium, magnesium, sodium, potassium, protons, iron, copper, chromium, lead, mercury, cobalt, gold, lithium, cesium, barium, zinc, chloride, bicarbonate, phosphate, bromide, iodide, sulfide, oxide, sulfide, and fluoride. The probe can comprise two or more sensors, wherein one of the two or more sensors is capable of detecting a first neurochemical or ion, and another of the two or more sensors is capable of detecting a second neurochemical or ion. The probe can comprise a sensor having the ability to detect dopamine, a sensor having the ability to detect, a sensor having the ability to detect serotonin, a sensor having the ability to detect adenosine, a sensor having the ability to detect norepinephrine, a sensor having the ability to detect GABA, a sensor having the ability to detect histamine, a sensor having the ability to detect acetylcholine, and a sensor having the ability to detect glutamate. The probe can comprise a sensor having the ability to detect pH. The probe can comprise a sensor having the ability to detect electrical brain signals. The probe and the control unit can be connected.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

DESCRIPTION OF THE DRAWINGS

FIG. 5. Comparison of FPA measurements of WINCS (A) and eDAQ (B) systems with FIA of 10 µM dopamine at the same CFM in a Faraday cage. Variable filtering of data: Raw, 100 Hz, 10 Hz, 1 Hz (from noisiest to the least noisiest response, respectively).

FIG. 17. A: 1: Battery, 2: Microprocessor, 3: Bluetooth®, 4: Working electrode lead, 5: Reference/counter electrode lead. B: WINCS encased in its sterilizable polycarbonate case.

FIG. 21. A: VL thalamic stimulation (100 Hz, 10 sec duration) at different intensities (0.5-2 mA) evoked progressively larger increases in local extracellular concentrations of adenosine. B: Increasing VL thalamic stimulation frequency from 50 Hz to 100 Hz at 1 mA also evoked progressively larger increases in local extracellular concentrations of adenosine. Black bars represent the duration of stimulation and vertical lines above these bars are recording artifacts that occurred during stimulation.

FIG. 22. A: Cortical stimulation (100 Hz at 1 mA for 10 sec) in the pig increased local extracellular concentrations of glutamate measured with WINCS and with a hardwired system (e-DAQ). B: Increasing cortical stimulation intensity from 0.5 to 2 mA at 100 Hz evoked progressively larger increases in local extracellular concentrations of glutamate. Black bars represent the duration of stimulation and vertical lines above these bars are recording artifacts occurring during stimulation.

FIGS. 24A-D depict probe assemblies, including chemical sensors, in accordance with some embodiments.

FIGS. 25A-D depict probe assemblies, including chemical and electrophysiological sensors, in accordance with some embodiments.

FIGS. 26A-F depict probe assemblies, including chemical and electrophysiological sensors and therapeutic tissue stimulators, in accordance with some embodiments.

FIG. 28A is a pseudo-color plot in grayscale of 2 mM $Ca^{2+}$. FIG. 28B is a graph plotting current vs. voltage. FIG. 28C is a graph plotting current vs. time at 1.5 V. FIG. 28D is a graph plotting background current. FIG. 28E is a pseudo-color plot in grayscale of 2 mM $Ca^{2+}$ (−0.4V to 1.0V). FIG. 28F is a voltammogram of FIG. 28D.

FIG. 29A contains pseudo-color plots in grayscale of four increasing concentrations of $Ca^{2+}$. FIG. 29B contains a graph plotting current vs. time and a graph plotting a calibration curve for $Ca^{2+}$.

FIG. 30A is a pseudo-color plot in grayscale of 1 mM $Mg^{2+}$ (−0.4V to 1.5V). FIG. 30B is a graph plotting current vs. voltage. FIG. 30C is a graph plotting current vs. time at 1.5V. FIG. 30D is a graph plotting background current. FIG. 30E is a pseudo-color plot in grayscale of 1 mM $Mg^{2+}$ (−0.4V to 1.0V). FIG. 30F is a voltammogram of FIG. 30D.

FIG. 31A contains pseudo-color plots in grayscale of four increasing concentrations of $Mg^{2+}$. FIG. 31B contains a graph plotting current vs. time and a graph plotting a calibration curve for $Mg^{2+}$.

FIG. 32A is a pseudo-color plot in grayscale of 0.5 mM $Ca^{2+}$. FIG. 32B is a pseudo-color plot in grayscale of 2 mM $Mg^{2+}$. FIG. 32C is a graph plotting current vs. voltage for $Mg^{2+}$ and $Ca^{2+}$. FIG. 32D is a graph plotting current vs. time for $Mg^{2+}$ and $Ca^{2+}$ (note that the response for these two ions were identical).

DETAILED DESCRIPTION

Figure 1:
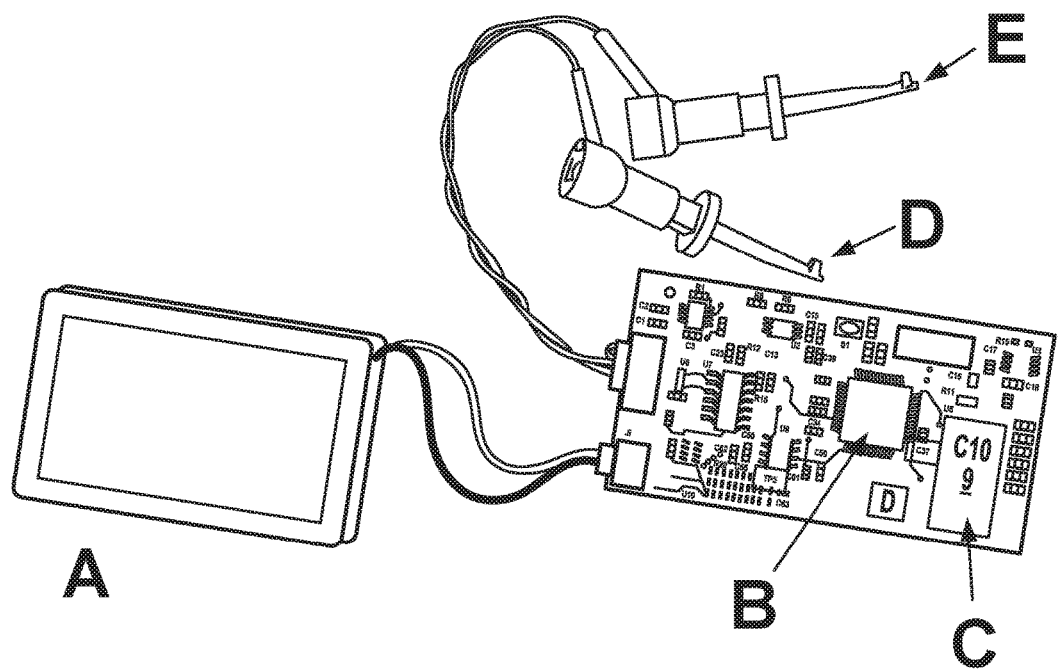
FIG. 1 is a photograph of exemplary WINCS hardware. A. Battery, B. Microprocessor, C. Bluetooth, D. Working electrode lead, E. Reference electrode lead.

This document relates to methods and materials involved in detecting chemical signals (e.g., neurochemical signals), electrophysiological signals, ions, or combinations thereof with brain tissue. For example, the document relates to methods and materials for using probes to detect neurochemical signals (e.g., neurotransmitter/neuromodulator concentrations), electrical signals, ions, or combinations thereof during deep brain stimulation. Examples of ions that can be detected using the methods and materials provided herein include, without limitation, calcium, magnesium, sodium, potassium, protons (pH), iron, copper, chromium, lead, mercury, cobalt, gold, lithium, cesium, barium, zinc, chloride, bicarbonate, phosphate, bromide, iodide, sulfide, oxide, sulfide, and fluoride. Examples of chemicals that can be detected using the methods and materials provided herein include, without limitation, dopamine, serotonin, adenosine, adenine mono- or tri-phosphate, norepinephrine, GABA, histamine, acetylcholine, glutamate, aspartate, epinephrine, nitric oxide, glycine, trace amines (e.g., tryptamine, phenylethylamine, tyramine, and octopamine), and amino acid-based neuropeptides (e.g., endorphins, enkephalins, and vasopressin). For example, a device provided herein can include one or more electrodes or sensors to detect one or more chemicals. In some cases, a single electrode or sensor can be used to detect a single chemical. For example, a device provided herein can include a first electrode designed to detect dopamine and a second electrode designed to detect glutamate. Another design is to use a singular sensing electrode, and by impressing different voltage ramps, different chemicals can be detected using the same electrode at slightly different times.

In some cases, a device provided herein can detect neurochemical signals, electrophysiological signals, ions, or combinations thereof in addition to delivering deep brain electrical stimulation (e.g., stimulation provided by a neurostimulator such as a Medtronic™ Soletra or Kinetra). For example, the methods and materials provided herein can be used to treat Parkinson's disease (PD). In some cases, a probe can be used to detect neurochemical signals and/or electrophysiological signals and to deliver electrical stimulation to the medial forebrain bundle (MFB) and various neuronal structures and nuclei of the brain of a Parkinson's patient to treat tremor and other motor symptoms. For example, the methods and materials provided herein can be used with regard to neurochemical and/or electrophysicological signals and in a manner that is not blind stimulation.

In some cases, a device provided herein can be implanted within a patient. For example, a device provided herein can be implanted within a patient's skull.

In some cases, inputs such as an accelerometer can be used to detect brain activity and/or to indicate seizure activity. For example, an accelerometer can be used to provide feedback for deep brain stimulation for tremor. An accelerometer on an extremity or an area of the body known to be affected can be used to provide direct feedback for the automated tuning of the stimulation of the brain function to reduce the tremor. Rather than depending upon an interview with a health care professional to modify the intensity or stimulation parameters, a self "tuning" algorithm can be used to reduce the tremor to a low level. For example, the device can automatically increase and decrease the stimulation while measuring the tremor level in the patient, resulting in optimum tremor reduction at minimum power levels, thereby extending battery life.

Multiplexed arrays of sensing electrodes or stimulation electrodes can be provided on various scales. In one embodiment, a 10×10 electrode array, offering 100 points in a plane, can be used, thereby covering a substantial volume area. The array can be sized such that a substantial volume can be stimulated by choice, and the activity can be detected in the volume. Time mapping of activity or effect can be provided based upon these arrays. By multiplexing the detection or stimulation, the overhead of data bandwidth can be decreased as well as the support electronics.

In some cases, a device provided herein can include a single electrode for FSCV that contains two independent areas of active electrode such as pyrolytic carbon or carbon fiber, that, by varying the FSCV impressed voltage, signals representing different neurochemicals can be determined. If the areas are too close together, which would cause interference, the signals can be multiplexed such that the signal is detected quasi simultaneously by measuring one chemical directly after the first chemical was detected. The device can be used to determine the effect of stimulation. Stimulation of two different areas can produce release of different neurochemicals (such as histamine, adenosine, glutamate, and dopamine) and the ratio or absolute amount changes can provide a physiologic effect of interest, such as creating long term memory in patients with short term memory loss.

In some cases, one or more chemicals (e.g., dopamine, adenosine, serotonin, and norepinephrine) can be detected using various scan waveforms in fast scan cyclic voltammetry applied to one or more sensors.

Figure 23:
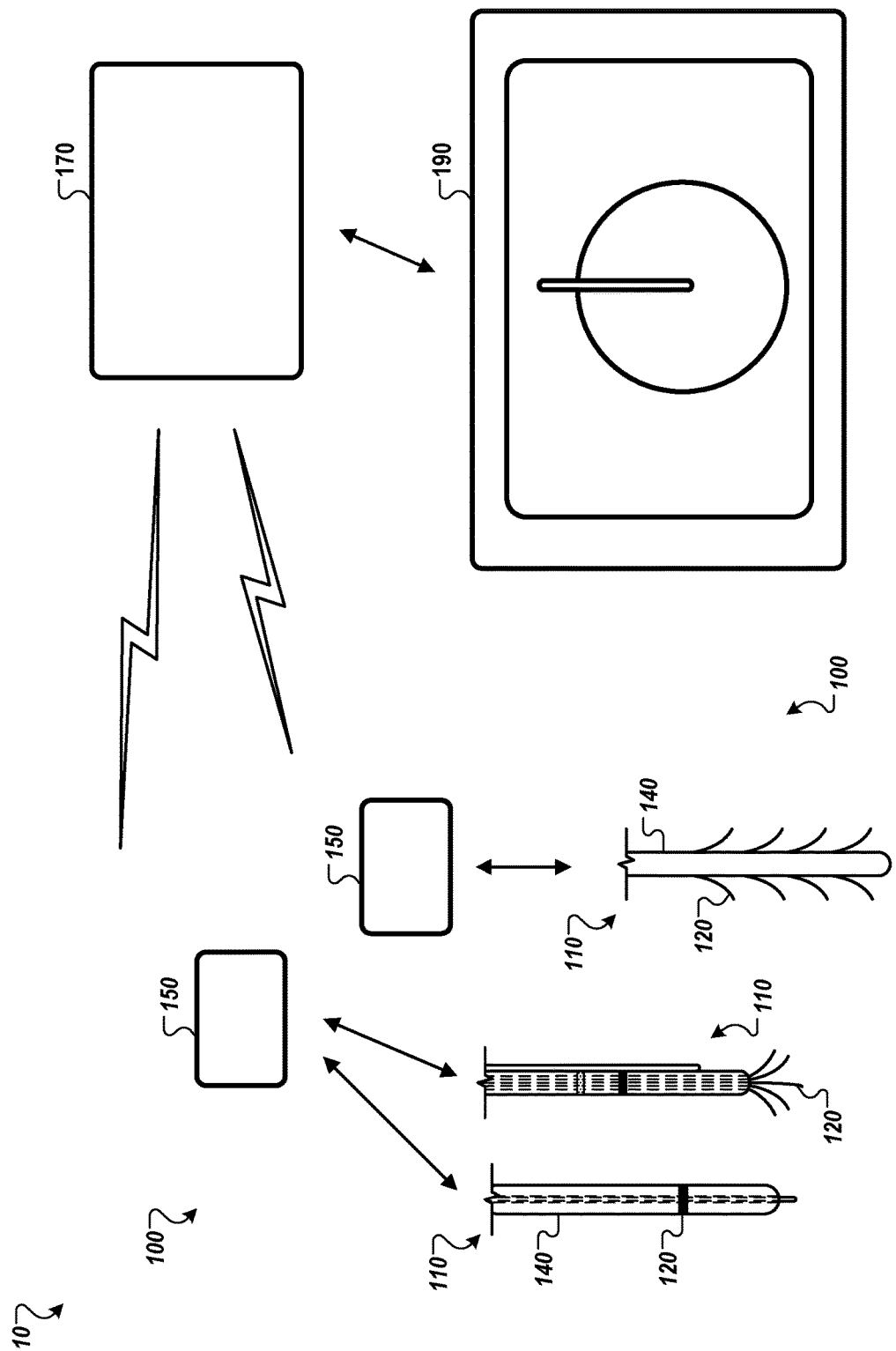
FIG. 23 depicts a deep brain stimulus system, including probe assemblies and physiological sensors, in accordance with some embodiments.

Referring now to FIG. 23, in some embodiments, a deep brain stimulation system 10 can include one or more electrode arrays 100 in wireless communication with a processing device 170. The processing device 170 can include, for example, a hand held communicating device, a personal computing workstation, a server, or the like, and can wirelessly communicate with the electrode array 100. The processing device 170 can communicate with a display 190, which can display information indicative of data received by the processing device 170. The electrode array 100 can include one or more probe assemblies 110 in communication with one or more control units 150 that, for example, can receive information from the individual probe assemblies 110, prepare the data for transmission, and telemeter the prepared data to the processing device 170. The control units 150 can also receive data from the processing device 170. For example, the processing device can instruct one or more of the control units 150 to transmit data from one or more of the probe assemblies 110 to the processing device 170. In another example, the processing device 170 can instruct individual control units 150 to activate electrodes on one or more of the probe assemblies 110 to stimulate surrounding tissue.

In some embodiments, the individual probe assemblies 110 can be positioned such that at least a portion of each of the probe assemblies 110 is located within the brain of a patient. In some embodiments, the one or more probe assemblies 110 (examples of which are described in more detail below in connection with FIGS. 24A-D, FIGS. 25A-D, and FIGS. 26A-F), can include sensors 120 for sensing physiological parameters (e.g., chemical concentrations, neurochemical concentrations, enzymatic activity, electrical activity, and the like) of the patient. The probe assemblies 110 can be electrically connected to the control unit 150 such that information sensed from a patients brain by the probe assemblies 110 (e.g., by the sensors 120) can be communicated to the control unit 150. Furthermore, the control unit 150 can process information received from the sensors 120 and can wirelessly communicate the processed information to the processing device 170. In some embodiments, the control unit 150 can be implanted in the patient (e.g., under the skin, scalp, skull, and the like). In some embodiments, at least a portion of the control unit 150 can be located outside of the patient.

In some embodiments, the probe assemblies 110 can include a stimulation probe 140, for example, used for deep brain stimulation (DBS). The processing device 170 can wirelessly transmit data indicative of a desired stimulation to the control unit 150. The control unit 150 can then activate one or more of the probes 140 to supply electrical stimulation (e.g., to the surrounding brain tissue). Deep brain stimulation (e.g., as performed by the system 10) can be used for the treatment of multiple disorders, such as Parkinson's disease (PD), tremor, dystonia, depression, and chronic pain.

Briefly, in use, the sensor system 10 can be used in a "closed-loop" mode such that the probe assemblies 110 can measure neurochemical and electrophysiological signals from the brain tissue of a patient and, based at least in part on these measured signals, can deliver therapeutic stimulation to the brain of a patient. In this way, the therapeutic stimulation can be adjusted until achieving a desired result, as measured by the probe assemblies 110. In another example, therapeutic stimulation can be delivered by the system 10 (e.g., via the probes 140) and the resulting display of information indicative of physiological parameters measured by one or more of the probe assemblies 110 can be used to optimize the placement of the individual assemblies 110 (and included probes 140). For example, the probe assemblies can be moved within the brain tissue of a patient until stimulation of the probes 140 results in an increased response, as measured by the probe assemblies 110.

Referring now to FIGS. 24A-D, in some embodiments, the system 10 can include one or more probe assemblies 200 where each probe assembly 200 can include one or more electrode sensors configured to measure a single chemical. In this configuration, a single probe assembly 200 can advantageously measure the level of more than a single chemical. Exemplary measurements performed by chemical sensors can include pH level, the concentration of neurochemicals (e.g., dopamine, serotonin, adenosine, norepinephrine, GABA, histamine, acetylcholine, glutamate, and the like), enzymatic activity, electrophsiological activity, and the like. An individual probe assembly 200 can include one or more retractable and advanceable sensors such as side chemical sensors 210 and distal chemical sensors 220 (FIG. 24A). In some embodiments, the probe assembly 200 can include one or more chemical sensors 230 bundled within an interior lumen of the probe assembly 200 (FIG. 24B). The probe assembly 200 can include one or more chemical ring sensors 240 around the circumference of the probe assembly 200 (FIG. 24C). In some embodiments, the probe assembly 200 can include a central lumen through which one or more chemical sensors 250 pass and further extend beyond the distal tip of the probe assembly 200 (FIG. 24D).

Referring now to FIGS. 25A-D, in some embodiments, the system 10 can include one or more probe assemblies 300 where each probe assembly 300 can include one or more electrode sensors (e.g., chemical electrode sensors of the type described in connection with FIGS. 24A-D, and the like) and one or more sensors configured to measure a single electrophysiological signal. Exemplary measurements performed by electrophysiological sensors can include EEG, EMG, EOG, and the like. An individual probe assembly 300 can include one or more retractable and advanceable sensors such as the side chemical sensors 210, one or more side electrophysiological sensors 315, the one or more distal chemical sensors 220, and one or more distal electrophysiological sensors 325 (FIG. 25A). In some embodiments, the probe assembly 300 can include the one or more chemical sensors 230 and one or more electrophysiological sensors 335 bundled within an interior lumen of the probe assembly 300 (FIG. 25B). The probe assembly 300 can include one or more of the chemical ring sensors 240 and one or more electrophysiological ring sensors 345 around the circumference of the probe assembly 300 (FIG. 25C). In some embodiments, the probe assembly 300 can include a central lumen through which one or more of the chemical sensors 250 and one or more electrophysiological sensors 355 pass and further extend beyond the distal tip of the probe assembly 300 (FIG. 25D). The probe assembly 300 can also include one or more sensors (e.g., chemical sensor 360, electrophysiological sensors (not shown), and the like) mounted on the outside wall of and external to the probe assembly 300.

Referring now to FIGS. 26A-F, in some embodiments, the system 10 can include one or more probe assemblies 400 where each probe assembly 400 can include one or more electrode sensors (e.g., electrode sensors of the types described in connection with FIGS. 24A-D, FIGS. 25A-D, and the like) and one or more electrode probes 405 that can provide therapeutic stimulation to surrounding tissues. Exemplary electrode probes 405 can be used to perform therapeutic deep brain stimulation. An individual probe assembly 400 can include the side chemical sensors 210 and the side electrophysiological sensors 315 that extend from a sidewall of the electrode probe 405 (FIG. 26A). In some embodiments, the probe assembly 400 can include one or more of the chemical sensors 330 and the electrophysiological sensors 335 bundled around the exterior of the electrode probe 405 and contained, at least partially, within an outer housing 402 (FIG. 26B). The probe assembly 400 can include one or more chemical ring sensors 240 and one or more electrophysiological ring sensors 345 around the circumference of the electrode probe 405 (FIG. 26C). In some embodiments, the probe assembly 400 can include one or more sensors (e.g., the chemical sensor 360, electrophysiological sensors (not shown), and the like) mounted on the outside wall of and external to the electrode probe 405 (FIG. 26D).

Referring now to FIG. 26E, in some embodiments, the probe assembly 400 can include the electrode probe 405 with a central lumen 407 through which one or more sensors (e.g., electrophysiological sensors 465, chemical sensors (not shown), and the like) can pass. Referring now to FIG. 26F, in some embodiments, the probe assembly 400 can include the electrode probe 405 with a central lumen 407 through which one or more of the chemical sensors 250 and one or more of the electrophysiological sensors 355 pass and further extend beyond the distal tip of the electrode probe 405. The probe assembly can also include one or more of the ring sensors 240 and 345 around the circumference of the electrode probe 405 and one or more of the sensors 210 and 215 that extend from the sidewall.

Figure 27:
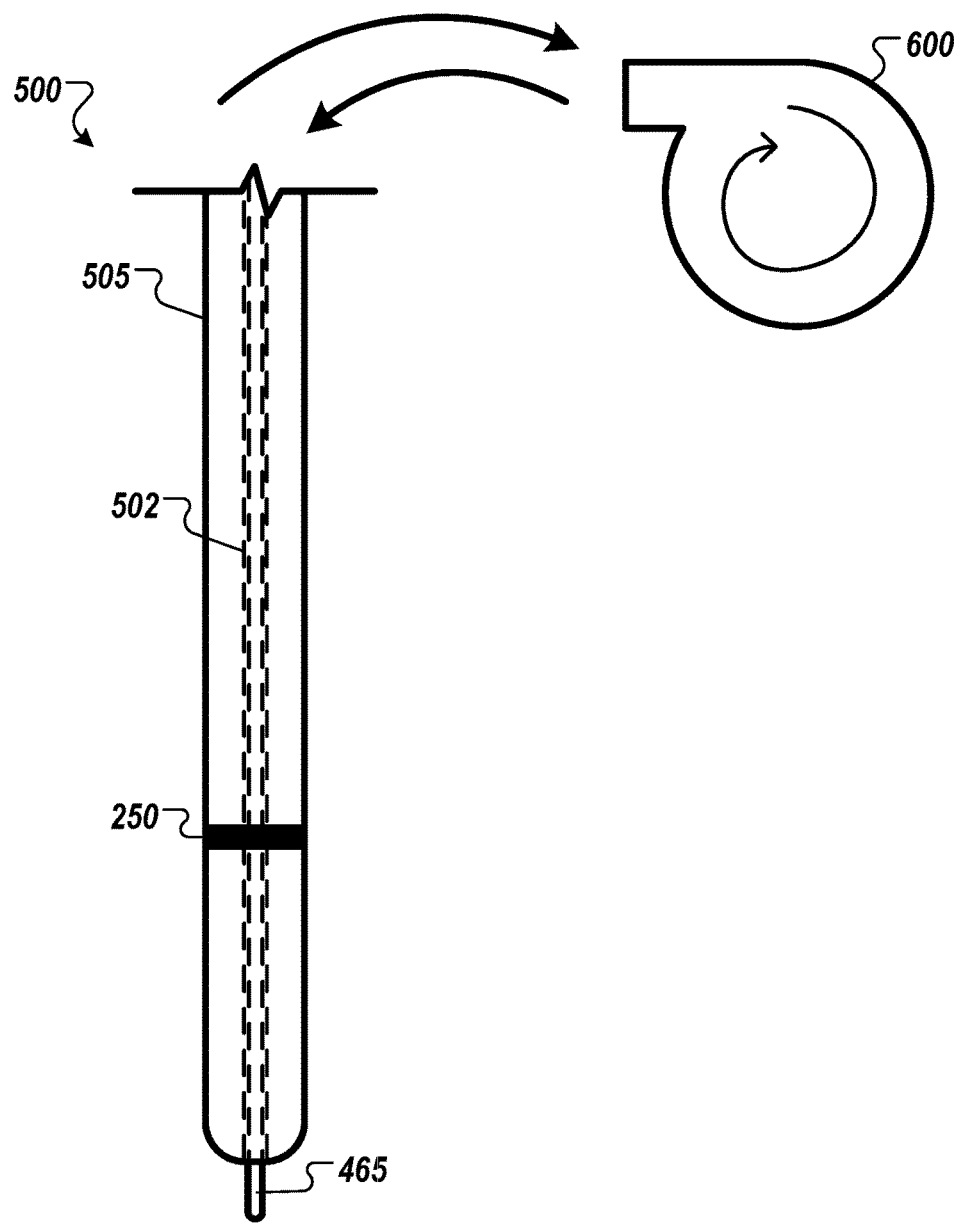
FIG. 27 depicts a probe assembly in communication with an implanted control unit, in accordance with some embodiments.

Referring now to FIG. 27, the deep brain stimulus system 10 can include the probe assembly 500 in communication with an implantable control unit 600. As such, signals can be communicated between the probe assembly 500 located at least partially in a patient and the control unit 600 implanted within the patient. Furthermore, the control unit 600 can be in communication with the remote processor 170 as described in connection with FIG. 23.

To deliver deep brain electrical stimulation, a lead (or electrode) of a neurostimulator can be positioned in the subthalamic nuclei (STN) of the brain. In some cases, a battery powered neurostimulator can be implanted (e.g. in the patient's chest) and have an extension connecting the neurostimulator and a lead in the patient's brain.

A neurostimulator lead can be positioned in a suitable part of the brain for stimulation-evoked dopamine release. For example, the lead can be positioned to stimulate the medial forebrain bundle (MFB) directly rather than the STN. Stimulation of the glutamatergic innovations originating from the subthalamic nucleus and terminating in the substantia nigra can activate nigrostriatal dopaminergic neurons directly (e.g., Meltzer et al., *Neurosci. Biobehav. Rev.*, 21:511-518 (1997)). Stimulation of glutamatergic neurons in the STN that project to the pedunculopontine nucleus in the hindbrain can activate nigrostriatal dopaminergic neurons both by the reciprocal excitatory innervation and subsequent activation of the substantia nigra by STN glutamatergic efferents, and indirectly by activating pedunculopontine cholinergic and glutamatergic inputs to the substantia nigra that act on glutamate ionotropic and metabotropic receptors located on substantia nigra dopaminergic cells (Blaha and Winn, *J. Neurosci.*, 13:1035-1044 (1993); Blaha et al., *J. Neurosci.*, 16:714-722 (1996); Forster and Blaha, *Eur. J. Neurosci.*, 17:751-762 (2003)). In some cases, the stimulating electrode can be placed within white matter dorsal to the STN (Saint-Cyr et al., *J. Neurosurg.*, 97:1152-1166 (2002); Voges et al., *J. Neurosurg.*, 96:269-279 (2002)), including the dorsolateral border of the STN (Herzog et al., *Mov. Disord.*, 19:1050-1054 (2004)), all of which contain the ascending dopaminergic axons. In some cases, a lead can be positioned unilaterally or bilaterally.

An appropriate electrical signal can have a frequency of between 90 Hz and 250 Hz. In some cases, an appropriate electrical signal can have a frequency of 100 Hz. In some cases, the stimulation can be a series of applied electrical current or voltage (e.g. a train). In some cases, stimulation can include a train with intertrain rest periods. For example, stimulation parameters can include rest periods in which no current is applied. The rest period can be from about 4 seconds to about 7 seconds. In some cases, an appropriate parameter for an electrical signal can be a burst-like stimulus. A burst-like stimulus can be a stimulus that mimics the natural pattern of dopamine neuronal activity (e.g., Hyland et al., *Neuroscience* 114:475-492 (2002)). For example, burst-like stimulus can include an alternating cycle of a 0.2 second current or voltage pulse and a 0.2 second inter-stimulus rest. The stimulation cycle can last for about 5-6 seconds, or approximately twenty 0.2 second stimuli. The cumulative rest period from the inter-stimulus rests can be between about 2.5 seconds and 3 seconds. Each burst-like stimulus can be followed by a contiguous rest period of about 4 seconds. In some cases, electrical stimulation, including a period of burst-like stimuli and a subsequent contiguous rest period, can cycle continuously.

The methods and materials provided herein can be used to enhance neurochemical release (e.g., dopamine release). In the case of dopamine, dopamine release in the striatum (caudate-putamen) evoked by electrical stimulation of dopamine axons contained with the MFB can be recorded amperometrically and voltametrically. In some cases, extracellular dopamine levels can be assessed using a probe described herein (e.g., a carbon fiber "dopamine" recording electrode). An electrometer can apply an electrical potential (e.g., +0.8 V) to the recording electrode via the auxiliary electrode, forcing the oxidation of dopamine at the recording electrode surface. For example, two electrons can be transferred to the recording electrode for each molecule of dopamine oxidized at the surface of the recording electrode. An analog current, constituting dopamine oxidation, can be subsequently converted (A/D converter) to a digital signal that can be monitored in real time on a computer screen. A dopamine oxidation current can correspond to a proportional increase in dopamine release in the striatum as a result of MFB stimulation.

In some cases, a remote unit can include an ADC for electrophysiological recordings. It is possible to perform electrophysiological recordings between voltage scans with fast-scan cyclic voltammetry (FSCV), a so-called quasi-simultaneous electrophysiology. This can allow one to correlate cellular activity with neurotransmitter changes. In some cases, the components necessary for stimulation control can be added onto the remote unit. This will not only allow the remote unit to vary the stimulation but it will also allow one to synchronize stimulation with electrochemical recordings thus reducing stimulation artifacts in the electrochemical recordings. In some cases, to perform chronic studies, the size of the remote unit can be reduced. In this regard, an integrated circuit comprising a Wireless Instantaneous Neurotransmitter Concentration System (WINCS) provides functionality that can be used to significantly reduce overall dimensions and weight (Roham et al., *Conf. Proc. IEEE Eng. Med. Biol. Soc.*, 2007:6044-7 (2007)).

The use of the data acquired from a WINCS system during DBS surgery can provide insight into the mechanism of action of DBS. The information also can be used to guide electrode placement during surgery. Such guidance can improve the therapeutic efficacy of the stimulation, reduce the stimulation intensity required for the desired effect (thereby prolonging battery life), and can reduce side effects associated with the stimulation. In some cases, the probes provided herein can be used to develop a "closed-loop" smart DBS system—an advanced technology that can utilize a brain-machine interface to alter stimulation intensity according to the measurements recorded at implanted microelectrodes. Such devices can advance DBS by reducing stimulation-associated side effects and maximizing the therapeutic response.

The effectiveness of the probes provided herein can be confirmed using an animal model such as a pig animal model. The pig is becoming increasingly popular in neuroscience research, an MPTP pig model exists for PD (Mikkelsen et al., *Neurotoxicol. Teratol.*, 21(2):169-75 (1999)), and pigs are significantly easier to acquire and maintain than non-human primates. To facilitate the implantation of electrodes in the pig, an MRI compatible head-frame for this species utilizing the same type of principles as the COMPASS (COMPASS International Inc., Rochester, Minn., USA) or Leksell (Elekta Inc., Norcross, Ga., USA) systems for image-guided surgery can be used. This can be helpful for WINCS testing prior to translation into the human OR.

The invention will be further described in the following examples, which do not limit the scope of the invention described in the claims.

EXAMPLES

Example 1

Development of a Wireless Instantaneous Neurotransmitter Concentration System (WINCS) for Intraoperative Neurochemical Monitoring During Deep Brain Stimulation (DBS) Surgery To help understand the surgical interventional mechanisms of DBS, an instrument capable of performing real-time measurements of central neurotransmitter changes in humans during DBS was developed. Briefly, a wireless instantaneous neurotransmitter concentration system (WINCS) combines advanced electrochemistry techniques such as fast-scan cyclic voltammetry (FSCV) and fixed-potential amperometry (FPA) with digital telemetry to perform microsecond electrochemical measurements at a brain-implanted microelectrode or microsensor. In this example, the WINCS included four modules designed in compliance with FDA-recognized consensus standards for medical electrical device safety: 1) front-end analog circuit for electrochemistry, 2) Bluetooth® transceiver, 3) microprocessor, and 4) battery (FIG. 1). Tests note herein included in vitro and in vivo comparison of signal stability, fidelity, and susceptibility to electromagnetic noise of the WINCS vs. conventional hardwired systems used in animal research.

The WINCS performed high-fidelity wireless measurements of dopamine concentrations at a carbon-fiber microelectrode (CFM) using FSCV and FPA. In vitro signals compared favorably to those collected at the same CFM using conventional hardwired electrochemistry systems. Furthermore, WINCS was capable of recording striatal dopamine release evoked by DBS delivered to the MFB in an anesthetized rat. WINCS recordings exhibited minimal susceptibility to typical electromagnetic noise found in an operating room setting, a substantial improvement over hardwired systems.

These results demonstrate that WINCS is capable of performing real-time wireless neurotransmitter monitoring during DBS surgery. Establishment of neurochemical changes associated with DBS can provide important information concerning the mechanisms of DBS and can improve the procedure through highly precise and guided stimulating-electrode placement. When successfully implemented, the WINCS approach for intra-operative neurochemical monitoring can be used as an implantable closed-loop, "smart" device incorporating a chemical micro-sensor, feedback control, and neuro-modulation to maintain neurotransmitters at optimal levels continuously for improved clinical efficacy.

Materials and Methods

Electrochemistry

FPA was performed by a potentiostat (Picostat®) in conjunction with an analog-to-digital signal converter-recorder (E-Corder®) run by Chart™ software, a commercially available hardwired system (eDAQ Pty Ltd, Colorado Springs, Colo., USA). Evaluation of dopamine concentration measurements using FPA at a CFM was performed with a fixed potential of +600 mV applied to the CFM. A conventional hardwired system, the Universal Electrochemistry Instrument (UEI; Department of Chemistry Electronic Shop, University of North Carolina), was used for FSCV in vitro and in vivo studies and was computer controlled by locally written software in LabVIEW (National Instruments, Austin, Tex., USA) (Michael et al., *Anal. Chem.*, 71(18): 3941-7 (1999)).

The FSCV potential at a CFM was cycled every 100 ms between −400 mV and +1000 mV at a rate of 300 V/s. The time for a scan to travel from a resting potential of −400 mV to +1000 mV and back again was 9.3 ms. The current recorded during one scan at a CFM within a buffer solution produces positive current on the forward scan from −400 mV to +1000 mV and negative current for the reverse back to the resting potential of −400 mV. The current recorded in the absence of any electroactive analyte in the buffer solution corresponds to the background current of the electrode and is produced largely by the equivalent capacitance of the electrode's double layer of charge. Changes in current recorded at the CFM with the addition of an electroactive analyte are seen at the forward scan with oxidation and in the reverse scan with reduction of the analyte.

Figure 2:
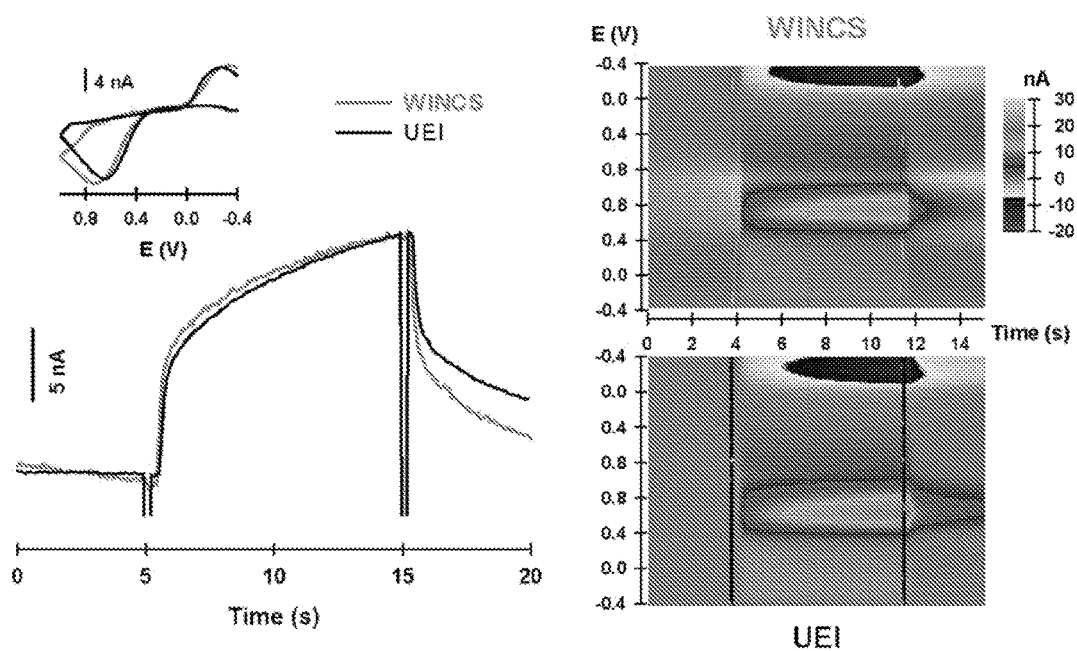
FIG. 2. Comparison of FSCV (Fast-Scan Cyclic Voltammetry) measurements with WINCS (Wireless Instantaneous Neurotransmitter Concentration System) (gray) and UEI (Universal Electrochemistry Instrument) (black) systems to FIA (Flow Injection Analysis) of 10 μM dopamine at the same CFM (Carbon Fiber Microelectrode) in a Faraday Cage.

The voltammogram of FSCV is the current plotted against the voltage applied (Cahill et al., *Anal. Chem.*, 68(18): 3180-6 (1996)). Current changes associated with the oxidation and reduction of an electroactive analyte at the CFM surface can be enhanced and quantified by subtraction of the relatively stable background current recorded in the absence of the analyte. Using the electroactive neurotransmitter dopamine as an example, the background-subtracted voltammogram exhibits a peak oxidation wave of dopamine near +600 mV and peak reduction wave near −200 mV (FIG. 2). During typical studies, several scans are averaged before background subtraction is performed.

The LabVIEW software (National Instruments, Austin, Tex., USA) supplies additional information in the form of a current vs. time graph and a three-dimensional color plot (FIG. 2). A temporal profile of a neurotransmitter can be determined by evaluating the current vs. time graph during FSCV. The three-dimensional color plot provides considerable amount of information about each FSCV study by plotting individual voltammograms serially with time. The x-axis corresponds with real-time, the y-axis corresponds with the potential change along the triangle wave for each scan, and the z-axis is the current change. Cross hairs can be placed on specific points within the color plot which correspond to the equivalent position on the voltammogram (y-axis) and the current-change vs. time graph (x-axis). This is helpful during in vivo experiments requiring differentiation of various electroactive analytes.

A CFM (FIG. 1; length 100 μm, diameter=5 μm), fabricated as described elsewhere (Cahill et al., *Anal. Chem.*, 68(18):3180-6 (1996)), was used with FPA and FSCV in vitro and in vivo dopamine recordings. A chloridized silver wire was employed as the reference/counter electrode (RE, Ag/AgCl) during in vitro and in vivo studies.

In Vitro Studies

A dummy cell was connected between the inputs of the reference and recording electrode leads to mimic the electrical properties of a CFM during electrochemical measurements. The dummy cell consisted of a 1500 pF capacitor and 100 kΩ resistor connected in series.

Figure 3:
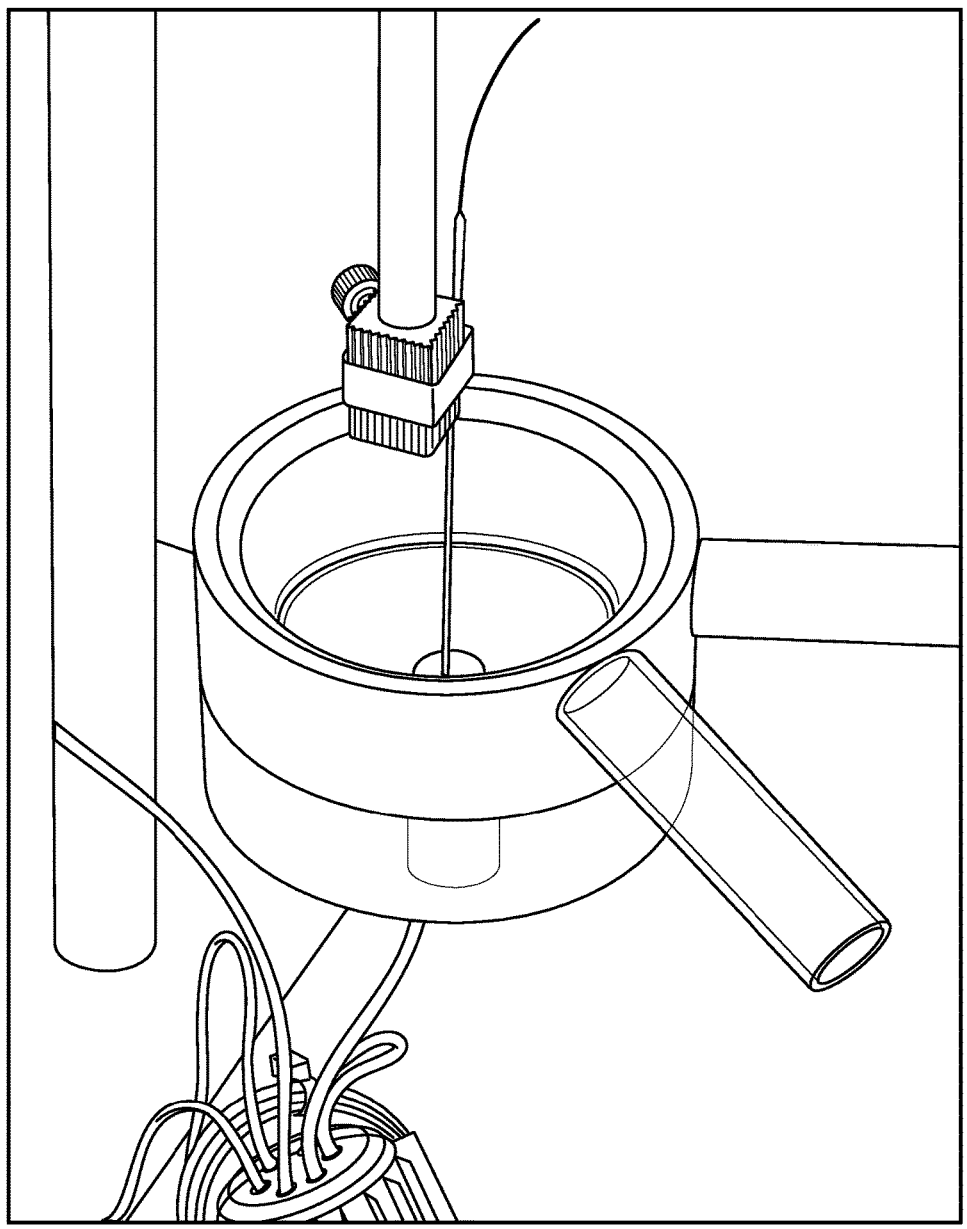
FIG. 3 is a photograph of a flow-cell device used for flow injection analysis (FIA) of the sensitivity of the working (recording) electrode.

Flow injection analysis was used for in vitro measurements of dopamine using FSCV and FPA at a CFM (Kristensen and Wightman, *Anal. Chem.*, 58:986-988 (1986)). In this procedure, well established for device testing and microsensor calibration, a CFM is placed in a flowing stream, and analyte is injected as a bolus. A buffer solution composed of 150 mM sodium chloride and 25 mM Hepes at a pH 7.4 was pumped across the CFM, positioned in the center of a Plexiglas reservoir (FIG. 3), at a rate of 4 mL/min. The RE was positioned on the periphery of the reservoir in the buffer solution. An electronic loop injector introduced dopamine for specific time intervals at defined concentrations to be tested.

In vivo Testing in Anesthetized Rat

Adult male Sprague-Dawley rats, 400-500 gm, were used for in vivo testing. The rats were housed under standard conditions, with ad libitum access to food and water. Care was provided in accordance with NIH and local institutional (IACUC) guidelines.

The animals were anesthetized using an intraperitoneal (i.p.) injection of urethane at a dose of 1.6 g/kg. The animal's skull was fixed in a commercially available stereotactic device (Kopf, Tujunga, Calif., USA) for rat surgery. Multiple craniectomies were performed for the reference, stimulating, and dopamine recording electrodes. The coordinates for the stimulating and recording electrodes were obtained from the Paxinos and Watson atlas (Paxinos, G., Watson, C, *The rat brain in stereotaxic coordinates*. Vol. second ed. 1986, New York: Academic Press) utilizing bregma as the reference point. The stimulating electrode was placed just over the medial forebrain bundle (MFB; AP −4.6; ML +1.2; DV −8.0 in mm) The recording electrode was positioned in the caudate-putamen (AP 1.2; ML 2.0 mm) with variable DV coordinates (4.5 to 6.0 mm) to obtain a robust signal. The Ag/AgCl RE was placed in superficial contact with cortical tissue contralateral to the stimulating and recording electrodes.

Electrical Stimulation

In vivo electrical stimulation was performed through a bipolar stimulating electrode (Plastics One, MS 303/2, Roanoke, Va., USA) with the tips separated by 1 mm. Bipolar stimulus pulses (±300 μAmps) were applied through a constant-current generator and optical isolator (NL 80, Neurolog, Medical Systems, Great Neck, N.Y., USA) at a frequency of 60 Hz.

Results

Hardware Development

The WINCS patient module incorporates front-end analog circuitry for electrochemistry, analog-to-digital converter, microprocessor, and a Bluetooth® radio on a single battery-powered multilayer printed circuit board. An Ultralife® rechargeable 740-mAh lithium-polymer battery (Ultralife Batteries Inc., Newark, N.Y., USA) was selected as the power source for the WINCS patient module. The battery's 3.7-V terminal voltage was converted by onboard dc-to-dc regulators to 3.3 V for the power supplied to the various circuit elements. The low supply voltage, within the range of stimulation applied during DBS surgery (≤10 V), and the isolation from extraneous fault current paths that battery power affords, provided measures of safety for the use of WINCS with patients. The lithium-polymer battery had internal current-limiting to prevent damage in the case of a short circuit. It also incorporated over-voltage and under-voltage protection. When fully charged, battery capacity was adequate for several hours of continuous operation, much longer than the expected 1-hour duration of the initial acute testing during DBS surgery.

The front-end analog circuitry for electrochemistry employed three operational amplifiers and two 12-bit digital-to-analog converters (DACs). An LMV751 low-noise operational amplifier (National Semiconductor Corporation, Santa Clara, Calif., USA) acted as a transimpedance amplifier for current-to-voltage conversion. A downstream INA2132U difference amplifier (Texas Instruments Incorporated, Dallas, Tex., USA) subtracted the potential applied to the CFM (e.g., the triangular ramp waveform applied during FSCV) prior to analog-to-digital conversion.

A C8051F061 microprocessor (Silicon Laboratories, Austin, Tex., USA) was clocked by an external crystal at 22.1184-MHz, a frequency that was readily divided to run the UART (universal asynchronous receiver/transmitter) output to the Bluetooth® module at the desired rates of 460,800 or 921,600 baud. The microprocessor, which had 64 kB of flash memory and 4352 bytes of data RAM (random access memory), was programmed using a JTAG (Joint Test Action Group) interface. One of the C8051F061 DACs produced the potential applied to the CFM: a fixed DC voltage for FPA, or a triangular ramp waveform for FSCV. One of the microprocessor's two analog-to-digital converters (ADCs) digitized the conditioned signal from the CFM.

Two 16-bit ADCs were incorporated in the microprocessor. One of the ADC ports was used to digitize the signal presented by the transimpedance amplifier. A second ADC port can be used in a version of WINCS to digitize extracellular electrical signals recorded by an electrophysiology electrode. The ADC sampling rate can be adjusted according to the desired recording being performed, typically 1 ksps (kilo-samples per second) for FPA, 100 ksps for FSCV, and 10-40 ksps for electrophysiology.

Digital telemetry between the remote unit and the base-station computer employed Bluetooth® radio technology. The LMX9838 Bluetooth® serial port module (National Semiconductor Corporation, Santa Clara, Calif., USA) on the WINCS patient module incorporated its own antenna and 32.768-kHz crystal. An USB-connected Bluetooth® "dongle" on the base-station computer completed the Bluetooth® link. Bluetooth devices operated in the unlicensed Industrial, Scientific and Medical (ISM) band of 2.400 to 2.485 GHz, using a spread-spectrum, frequency-hopping, full-duplex signal.

The WINCS patient module circuit board and battery were packaged in a hermetically sealed polycarbonate case that allows for sterilization using the Sterrad® gas plasma process.

The base-station computer was a Windows-XP laptop running custom software that controls the parameters and operation of the WINCS patient module, such as starting and stopping data acquisition and transmission, modifying the applied potential waveform, and changing the sampling rate. Additional software can be developed to calculate and display cyclic voltammograms and other data representations in near real-time, as the data is received via telemetry. Data was saved to disk as a sequence of unsigned two-byte integers, a format suitable for post-processing by conventional applications such as MATLAB® (The MathWorks, Inc., Natick, Mass., USA) or LabVIEW (National Instruments, Austin, Tex., USA).

In Vitro Comparison to Conventional Systems

Figure 4:
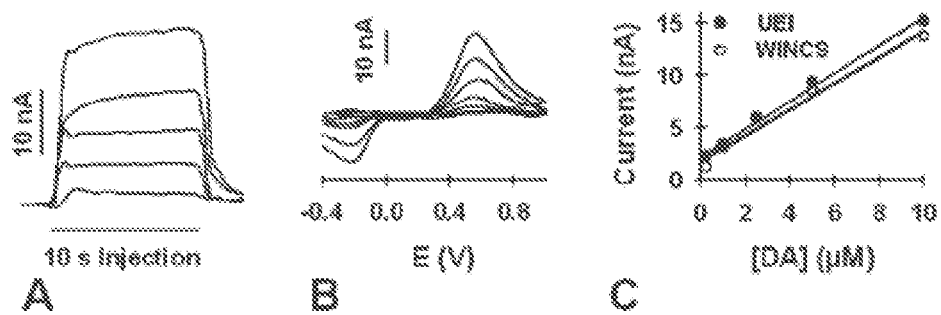
FIG. 4. Comparisons of the WINCS and the UEI for obtaining a dopamine (DA) calibration curve. A: Current measured at the peak oxidative potential for a bolus injection of dopamine and measured by the WINCS. Increasing current corresponds to increasing dopamine concentration (0.25, 1, 2.5, 5, and 10 µM). B: Background-subtracted voltammograms determined by the WINCS. As in panel A, increasing current corresponds to increasing dopamine concentration. C: Dopamine calibration curves collected by the WINCS (open circles) and the UEI (closed circles). The line describes the best linear fit.

All in vitro studies were performed in a Faraday cage to limit low frequency electromagnetic noise interference for the hardwired systems. Although unnecessary, the WINCS remote unit was placed within the Faraday cage as well, while the base-station computer's Bluetooth® transceiver was positioned outside the cage, about 6 feet away. A Faraday cage can reduce all electronic signals, however, using a wire screen, the low frequencies, such as line voltage AC are reduced and high frequency signals such as used by Bluetooth® are not attenuated very much. The in vitro FSCV comparison was performed utilizing FIA at the same CFM. FIG. 2 compares the response of the conventional system (black) with WINCS (red) for 10 μM dopamine. Equivalent scales were used for the two recordings. The overlay of the two signals demonstrated a nearly identical temporal and current response to the injected dopamine on the current-versus-time graph. These results suggest that the two systems performed comparably during FSCV measurements of dopamine. Furthermore, FIG. 4 demonstrates WINCS ability to record dopamine at varying concentrations using FSCV during FIA. The concentration curve displayed the average current measurements for 0.25 μM, 2.5 μM, 5 μM, and 10 μM with a correlation coefficient of 0.9961.

FPA was also tested, by comparing the response of the two systems in a Faraday cage utilizing FIA at the same CFM. As shown in FIG. 5, the amperometric response of the conventional and WINCS systems to 10 μM dopamine was nearly identical. The evident presence of noise in the WINCS signal at 100 Hz low pass filtering may be due in part to interactions with a mains-powered syringe pump, a part of the flow-injection apparatus that required electromagnetic shielding for acceptable performance with battery-powered WINCS, but not with the mains-powered hard-wired instrumentation. Further testing can be performed to address the electromagnetic arcana responsible for signal degradation in this configuration. At 10 Hz low-pass filtering, typically used in hardwired systems for both in vitro and in vivo recording, the WINCS amperometric signal was relatively noise free. In addition, when compared to the WINCS two-electrode electrometer, marginally better noise performance by three-electrode electrometers such as eDAQ can be expected, especially in the presence of high background currents.

In Vivo Comparison to Conventional Systems

Figure 6:
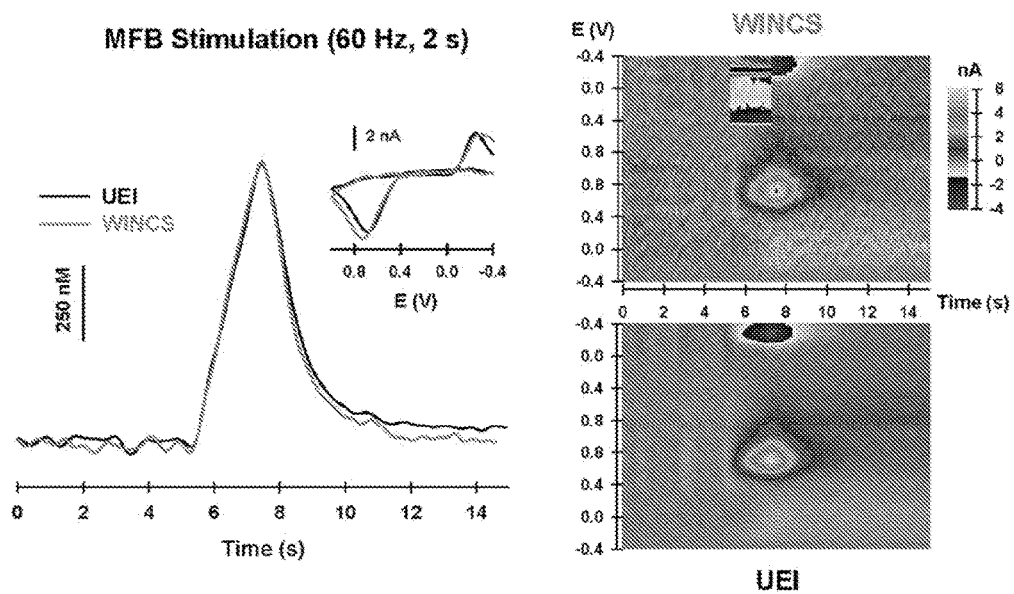
FIG. 6. Comparison of FSCV recordings during stimulation-evoked release of dopamine between the WINCS (gray) and UEI (black) systems. Medial Forebrain Bundle (MFB) stimulation (60 Hz, 300 µA for 2 seconds) at the same CFM positioned in the caudate-putamen.

Stimulation-evoked release of dopamine in an anesthetized rat was used to compare FSCV measurements collected by the wireless and hardwired systems in vivo. The recordings were performed at the same CFM implanted in the striatum during stimulation (60 Hz, 2 s, 300 μA for 2 s) of the MFB in a Faraday cage. FIG. 6 demonstrates the recordings for the WINCS (red) and UEI (black) systems. The temporal changes in current were nearly identical on the current-versus-time chart. The voltammogram and color plot were consistent with a standard dopamine signal (Garris et al., *Brain Res.*, 753(2):225-34 (1997)) and were effectively identical, validating WINCS' ability to record electrically evoked dopamine in the CNS with the same signal fidelity as a conventional wall-mounted AC powered system.

Figure 7:
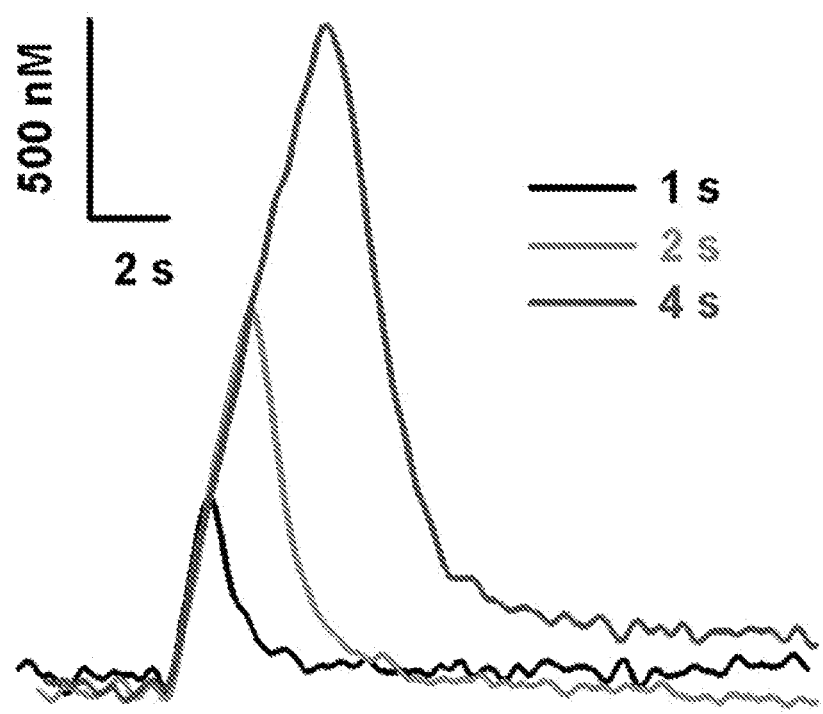
FIG. 7. Electrically evoked dopamine release from caudate-putamen after MFB stimulation (60 Hz, 300 µA) in an anesthetized rat. Recording at increasing stimulation trains, 1 s, 2 s, 4 s (from smallest to largest response, respectively).

To further assess the capacity of the WINCS system to measure stimulation-evoked release of dopamine, the effects of variable trains of stimulation were recorded using the same anesthetized rat and CFM as used in FIG. 6, in a Faraday cage. FIG. 7 shows the FSCV current-versus-time measurements during 1-s (black), 2-s (red) and 4-s (blue) stimulation trains (60 Hz, 300 μA). As would be expected, the increased stimulation trains resulted in proportionally increased dopamine release. Furthermore, the temporal response for the different trains exhibited a proportional ramp in current change on the current-versus-time plot. These results demonstrate WINCS' ability to measure dopamine during variable physiological and stimulation conditions.

Comparison in an Operating Room

Figure 8:
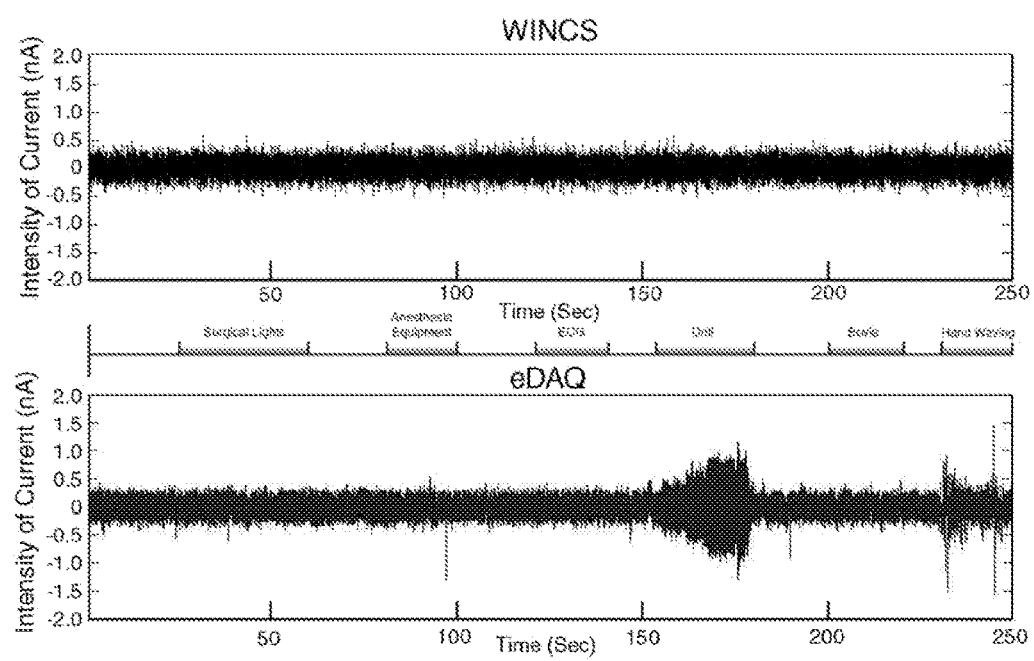
FIG. 8. Comparison of WINCS vs. eDAQ system for susceptibility to noise in the operating room (OR) environment during FPA. RC dummy cells were connected to each system and placed on the OR surgical table within two feet of each other. A 75-Hz low-pass filter was placed on each signal. Electrical devices were turned on and off at variable intervals: surgical lights 25-60 s, anesthesia machine 80-100 s, ECG monitor 120-140 s, power hand drill (5 feet away) 150-165 s, Bovie electrocautery 180-210 s, hand waving (1 foot above dummy cells) 230-250 s.
Figure 9:
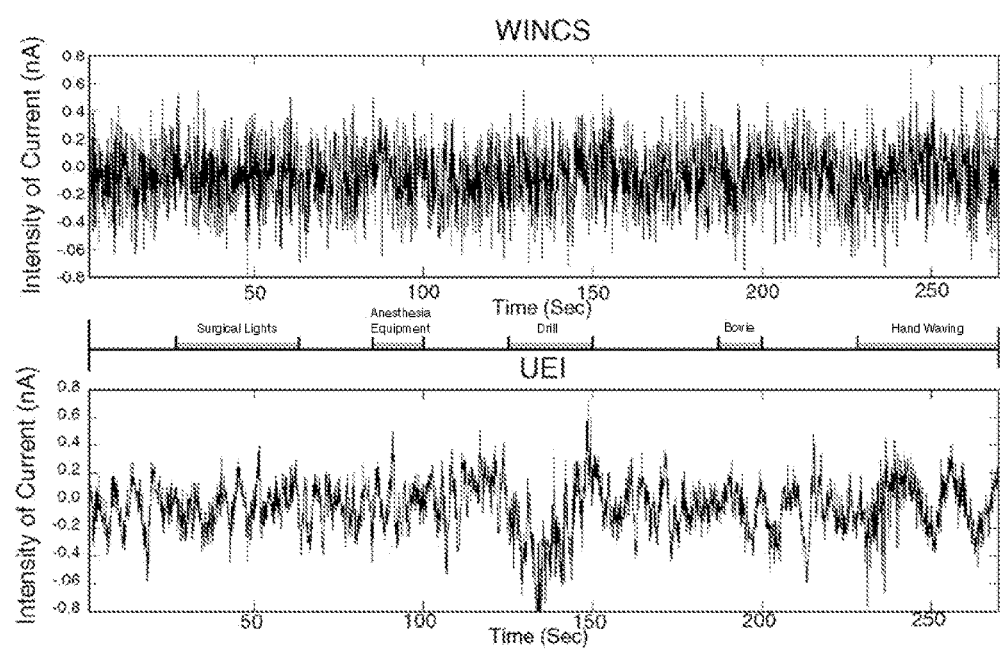
FIG. 9. Comparison of WINCS vs. UEI system for susceptibility to noise in the operating room environment during FSCV. RC dummy cells were connected to each system and placed on the OR surgical table within two feet of each other. Electrical devices were turned on and off at variable intervals: surgical lights 25-60 s, anesthesia machine 80-100 s, power hand drill (5 feet away) 120-150 s, Bovie electrocautery 180-200 s, hand waving (1 foot above dummy cells) 220-250 s.

One of the advantages of the WINCS unit is analog-to-digital conversion at the site of signal collection and digital telemetry of this recorded signal, resulting in reduced susceptibility to ambient noise, especially 60-Hz signals from mains-powered equipment. This feature becomes increasingly important when attempting to record electrochemical measurements in the electromagnetic noise-rich environment found in a typical operating room (OR). To evaluate the susceptibility of the WINCS signal to electromagnetic interference (EMI) in the OR, measurements of the WINCS system were compared to the eDAQ during FPA (+600 mV applied potential) and UEI with FSCV (−0.4 V to 1.0 V) in an OR used for large animal surgeries. RC dummy cells were connected to each system and placed on the OR surgical table within two feet of each other. Various electrical devices normally utilized during DBS surgery were turned on and off sequentially to evaluate noise perturbations. In FIG. 8, a 75-Hz low-pass filter was used to better demonstrate the interference in the recorded signal. This figure reveals no alterations in the WINCS signal during any of the electrical devices activation. The eDAQ signal exhibited the largest response to the electrical drill and hand motion over the dummy-cell. In FIG. 9, the WINCS signal was again unaffected by the maneuvers in the OR, while the UEI was most susceptible to the electrical drill and the hand waving. Though further testing can be performed during DBS surgery, these results demonstrate that the WINCS signal exhibits minimal susceptibility to noise in the OR environment.

Example 2

Figure 10:
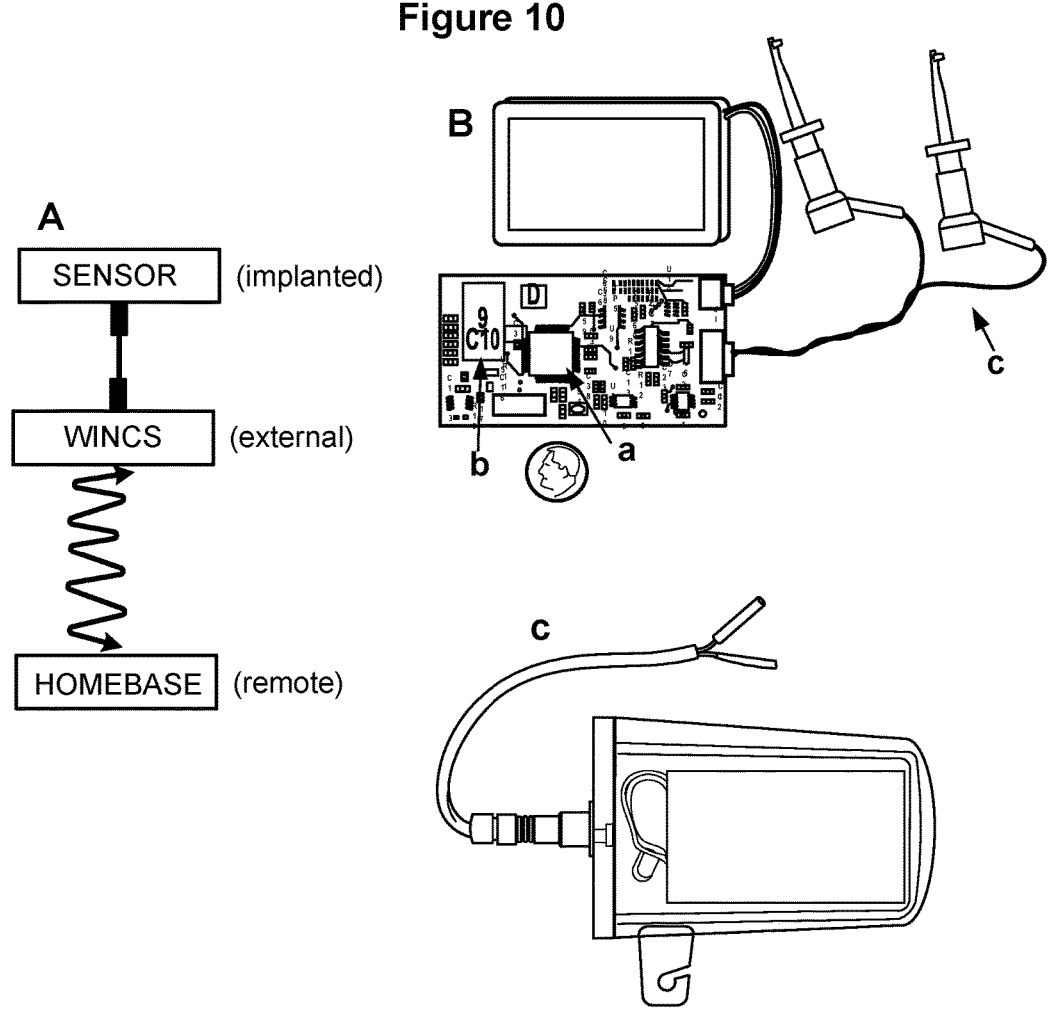
FIG. 10 contains a photograph of an exemplary WINCS instrument. A. Conceptual view of WINCS application. B. Photograph of WINCS circuit board with attached ULTRA-LIFE® battery: a), microprocessor; b), Bluetooth transceiver; c), leads for working electrode and reference electrodes. C. Photograph of encapsulated WINCS with external electrode contacts.

Development of Wireless Instantaneous Neurotransmitter Concentration System (WINCS) for Intraoperative Neurochemical Monitoring Using Fast-Scan Cyclic Voltammetry Materials and Methods
Animals Four adult male Sprague-Dawley rats, weighing 300-400 g, were used for in vivo testing. Rats were housed under standard conditions, with ad libitum access to food and water. Care was provided in accordance with NIH and local institutional (IACUC) guidelines.
FSCV at a CFM For FSCV, the potential at the CFM was linearly ramped every 0.1 s between −0.4 and 1.0 V at a rate of 300 V/s. The microsensor rested at a bias potential of −0.4 V in between scans. WINCS was compared to a conventional hardwired system, the Universal Electrochemistry Instrument (UEI; Department of Chemistry Electronic Shop, University of North Carolina), which was computer controlled by commercially available software (ESA Biosciences, Chelmsford, Mass.). The CFM was constructed by aspirating a single carbon fiber (r=2.5 μm) into a borosilicate glass capillary and pulling to a microscopic tip using a pipette puller (Cahill et al., *Anal. Chem.*, 68:3180-3186 (1996)). The reference electrode, an Ag/AgCl reference electrode, was fabricated by chloridizing a 31 g silver wire (Garris et al., *J. Neurochem.*, 68:152-161 (1997)).
Flow Injection Analysis Flow injection analysis was used for in vitro measurements with FSCV at a CFM (Kristensen et al., *Anal. Chem.*, 58:986-988 (1986)). In this procedure, well established for device testing and microsensor calibration, a CFM was placed in a flowing stream, and analyte was injected as a bolus. A buffer solution composed of 150 mM sodium chloride and 25 mM Hepes at a pH 7.4 was pumped across the CFM, positioned in the center of the inflow tubing to a Plexiglas reservoir, at a rate of 4 mL/min. The Ag/AgCl reference electrode was located in the bottom of the reservoir immersed in buffer solution. An electronic loop injector, locally fabricated, introduced a bolus of analyte for 10 s into the flowing stream at defined test concentrations.
In Vivo Experiments After anesthesia with urethane (1.6 g/kg i.p.), the rat was immobilized in a commercially available stereotaxic device (David Kopf Inst., Tujunga, Calif., USA). Multiple craniectomies were performed for implanting the reference, stimulating, and recording electrodes. Stereotaxic coordinates were obtained from a rat brain atlas based on flat-skull position utilizing bregma and dura as reference points. All coordinates, anteroposterior (AP), mediolateral (ML), and dorsoventral (DV), are given in mm. The stimulating electrode was placed just above the medial forebrain bundle (MFB; AP −4.6; ML +1.2; DV −8.0 to −9.0) of the right hemisphere. The recording electrode (i.e., the CFM) was positioned ipsilaterally in the dorsomedial striatum (AP +1.2; ML +2.0; DV −4.5 to −6.0). The reference electrode was inserted in superficial cortical tissue contralateral to stimulating and recording electrodes. Positions of the stimulating and recording electrodes were initially adjusted to obtain a robust signal for electrically evoked levels of extracellular dopamine measured in the striatum and not changed thereafter for the remainder of the experiment.
Electrical Stimulation Electrical stimulation was computer generated and consisted of biphasic stimulus pulses (300 μA and 2 ms each phase). The twisted bipolar stimulating electrode (Plastics One, MS 303/2, Roanoke, Va., USA) was insulated except for the exposed tips, which were separated by 1 mm. 60 Hz pulse trains were applied through a constant-current generator and optical isolator (NL 80, Neurolog, Medical Systems, Great Neck, N.Y., USA). In the case of the UEI, but not the WINCS, stimulation pulse trains were synchronized with the voltammetry so that a voltage scan and stimulus pulse never overlapped in time.
Results
Instrument Overview As shown in FIGS. 1 and 10 (e.g., FIG. 10A), this WINCS configuration includes an external chemical measurement device supporting a brain-implanted microsensor and wirelessly controlled by a home-base computer. When supporting human intraoperative neurochemical monitoring, the WINCS circuit board and battery (FIG. 10B) can be packaged in a hermetically sealed polycarbonate case (FIG. 10C) that can allow for sterilization using the Sterrad® gas plasma process and attached to the stereotactic frame. The home base can be situated remotely to WINCS, so as not to interfere with the functional neurosurgical procedure, but within wireless transmission distance of around 10 m line of sight.
Hardware Development WINCS incorporates modules with front-end analog circuitry for FSCV, microprocessor, and Bluetooth® radio, on a single battery-powered multilayer printed circuit board. An Ultralife® rechargeable 740-mAh lithium-polymer battery (Ultralife Batteries Inc., Newark, N.Y., USA) was selected as the power source. The battery's 3.7-V terminal voltage is converted by onboard dc-to-dc regulators to 3.3 V for the power supplied to the various circuit elements. The lithium-polymer battery has internal current limiting, and over- and under-voltage protection. When fully charged, battery capacity is adequate for at least three hours of continuous operation.

The front-end analog circuitry for FSCV employed three operational amplifiers and two 12-bit digital-to-analog converters (DACs). An LMV751 low-noise operational amplifier (National Semiconductor Corp., Santa Clara, Calif., USA) acts as a transimpedance amplifier for current-to-voltage conversion. A downstream INA2132U difference amplifier (Texas Instruments Inc., Dallas, Tex., USA) subtracts the potential applied to the CFM (i.e., the triangular ramp waveform applied during FSCV) prior to signal digitization.

A C8051F061 microprocessor (Silicon Laboratories, Austin, Tex., USA) is clocked by an external crystal at 22.1184-MHz, a frequency that can be readily divided to run the UART (Universal Asynchronous Receiver/Transmitter) output to the Bluetooth® module at the desired rates of 460,800 or 921,600 baud. The microprocessor, which has 64 kB of flash memory and 4.352 kB of RAM (random access memory), can be programmed using a JTAG (Joint Test Action Group) interface. One of the C8051F061 DACs produces the potential applied to the CFM for FSCV. Two 16-bit analog-to-digital converters (ADCs) are incorporated in the microprocessor. One of the ADC ports is used to digitize the CFM signal presented by the transimpedance amplifier. The ADC sampling rate can be adjusted according to the desired recording being performed. A rate of 100 kilosamples per second (ksps) was used for FSCV.

Digital telemetry between the remote unit and the base-station computer employs Bluetooth® radio technology. The LMX9838 Bluetooth serial port module (National Semiconductor Corp., Santa Clara, Calif., USA) on WINCS incorporates its own antenna and 5-GHz voltage-controlled oscillator (VCO). A USB-connected Bluetooth® "dongle" on the base-station computer completes the Bluetooth® link. Bluetooth® devices operate in the unlicensed Industrial, Scientific and Medical (ISM) band of 2.400 to 2.500 GHz, using a spread-spectrum, frequency-hopping, full-duplex signal.

The base-station computer is a Windows-XP® laptop computer running custom software that controls the parameters and operation of WINCS, such as starting and stopping data acquisition and transmission, modifying the applied potential waveform, and changing the sampling rate. Data were saved to the computer hard drive as a sequence of unsigned two-byte integers, a format suitable for post-processing by software such MATLAB® (The MathWorks Inc., Natick, Mass., USA) or LabVIEW (National Instruments, Austin, Tex., USA).

FSCV at a CFM

FSCV specializes in rapid and chemically resolved analyte monitoring at a microsensor. Like all voltammetric techniques, FSCV measures electroactive species through applying a voltage to the sensing surface and measuring oxidative and reductive currents. A CFM is the microsensor of choice for FSCV. The size of the sensing region depends upon the length of the exposed carbon fiber beyond the glass insulation and its diameter; a carbon-fiber length of approximately 100 μm and diameter of 5 μm were used for these measurements.

The potential of the CFM is scanned at regular intervals for the technique of FSCV. Only during the actual voltage scan is analyte measured. The scan was applied at 10 Hz (i.e., every 100 ms) in this study, and the potential applied to the CFM during a single scan and plotted versus time is shown in FIG. 11A, top panel. The duration of the scan was 9.3 ms at the scan rate of 300 V/s. The high scan rate produces a large background current due to double layer capacitance at the CFM tip. Background current collected in the absence of analyte and during a single scan is shown in FIG. 11A, middle panel (black line), and plotted with time. Current corresponds to the applied voltage in the triangle scan above in FIG. 11A. The large background current masks additional current due to the presence of dopamine (red line). Background current was stable over short times and can be subtracted to reveal the pure faradic current produced by dopamine electrolysis. In the background subtracted current recording shown in FIG. 11A, bottom panel, the downward facing peak at ~4 ms was due dopamine oxidation to dopamine-ortho-quinone and the upward facing peak at ~8 ms was due to the reduction of the electroformed quinone back to dopamine. Times for dopamine oxidation and reduction, extended vertically in FIG. 11A by the dashed lines, corresponded to the potentials of approximately ~0.6 and −0.2 V, respectively (see triangle scan in top panel). The voltammogram, which serves as a chemical signature to identify the analyte detected, was the plot of these measured currents with respect to the applied voltage, rather than time.

As shown in FIG. 11B, background subtracted cyclic voltammograms was plotted sequentially using a pseudo-color display, with time as the x axis, voltage as the y axis, and current as the z or color axis. This pseudo-color plot shows dopamine measured in the striatum of an anesthetized rat and elicited by electrical stimulation of the MFB. Features in the pseudo-color display occurring around 5 to 10 s corresponded to the electrically evoked release of dopamine measured at the CFM tip. Specifically, green-purple and black-yellow features around +0.6 and −0.2 V, respectively, directly relate to the oxidation of dopamine and the reduction of the electroformed quinone, respectively. The brown color reflects zero current, established by the background subtraction procedure.

Figure 11:
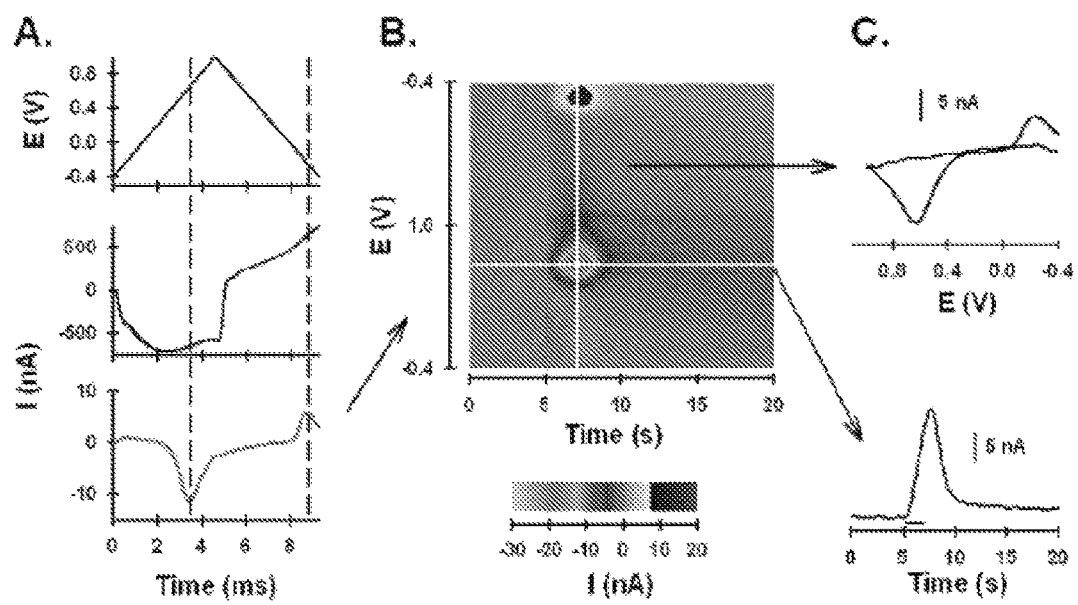
FIG. 11. FSCV. A. Applied triangle waveform (top panel); background current with and without dopamine (middle panel; two lines that generally overlap are shown); background subtracted current (bottom panel). B. Pseudo-color plot. C. Background subtracted cyclic voltammogram (top panel); current measured at the peak oxidative potential for dopamine and plotted with time (bottom panel).

Dynamic changes in dopamine levels produced by the electrical stimulation were obtained by plotting current measured at the peak oxidative potential for dopamine (~+0.6 V; horizontal white line on the pseudo-color plot in FIG. 11B) with time, as shown in FIG. 11C, top panel. Current was converted to concentration by postcalibration of the CFM with flow injection analysis and known dopamine standard solutions. An individual background subtracted voltammogram was also obtained for any time point by plotting current measured at the applied potential (vertical white line on the pseudo-color plot in FIG. 11B), as shown in FIG. 11C, bottom panel. Note that downward- and upward-facing peaks of the individual background subtracted voltammogram directly correspond to the green-purple and black-yellow features of the pseudo-color display, respectively. All measurements shown in FIG. 11 were collected at the same CFM.

In Vitro FSCV at a CFM

Figure 12:
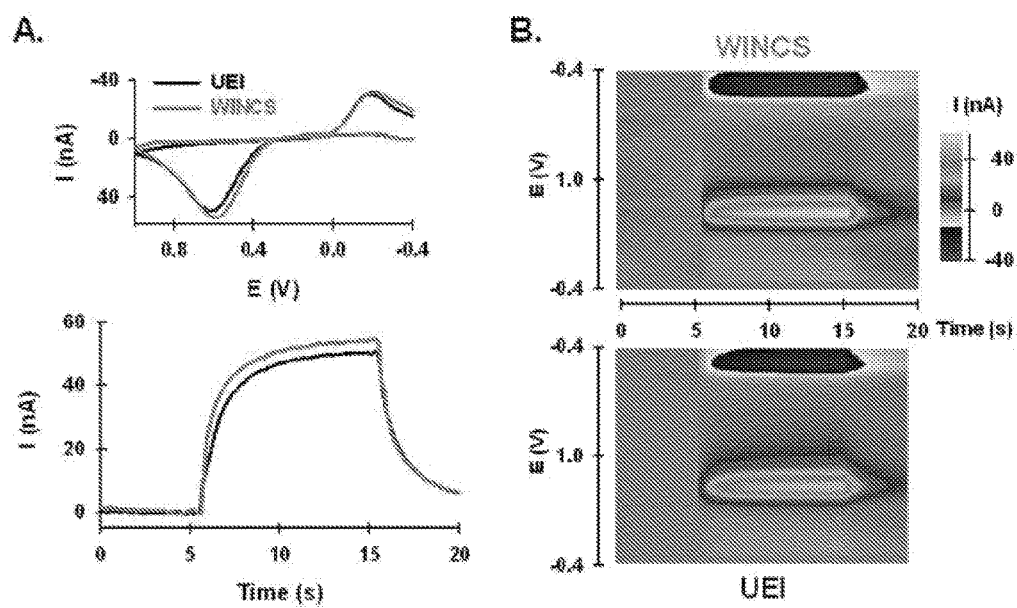
FIG. 12. Comparison of WINCS and UEI using flow injection analysis. A. Background subtracted voltammograms for dopamine recorded by WINCS (gray) and UEI (black; top panel); current measured at the peak oxidative potential for dopamine, plotted with time and measured by WINCS (gray) and UEI (black; bottom panel). B. Pseudo-color plots for dopamine determined by WINCS (top panel) and UEI (bottom panel).

FIG. 12 compares WINCS to a conventional hardwired system (i.e., UEI) for FSCV measurements of dopamine at a CFM using flow injection analysis. In FIG. 12A, bottom panel, current recorded at the oxidative potential for dopamine (~+0.6 V) during a 10 s, 10 μM bolus injection was plotted with time. Notice similar dynamics and amplitude for signals collected by WINCS (red) and UEI (black). The small time delay between the bolus injection at 5 s and the increase in signal was due to the length of tubing between the reservoir containing the CFM and the upstream injection of dopamine. A similar delay occurred when the bolus injection was terminated. The top panel shows comparable dopamine background subtracted cyclic voltammograms generated by the two systems from the plateau signal of the bolus injection. The pseudo-color plots shown in FIG. 12B and obtained during the dopamine bolus injection were also similar for WINCS (top) and UEI (bottom). A slight injection artifact was observed as a vertical line at 5 and 10 s. This artifact was somewhat more pronounced in the hardwired UEI system. All measurements were collected at the same CFM.

Figure 13:
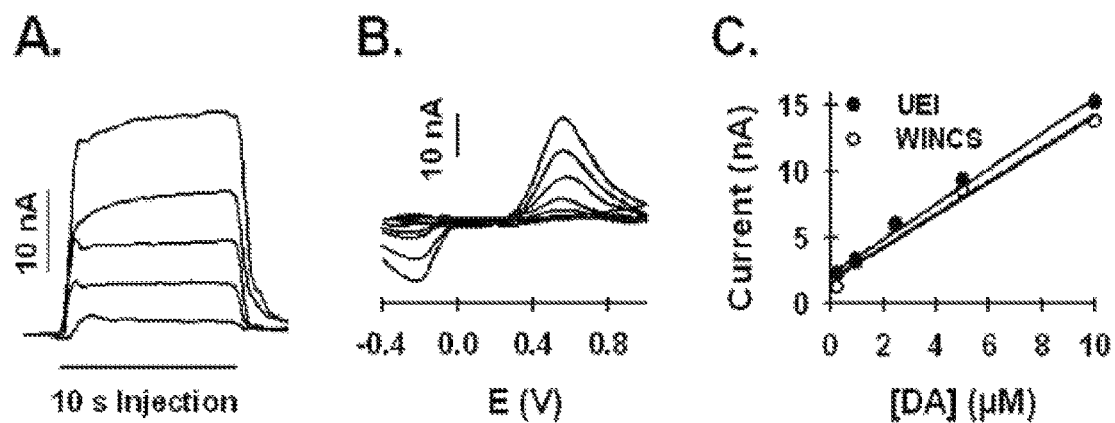
FIG. 13. Comparison of WINCS and UEI for obtaining a dopamine calibration curve. A. Current measured at the peak oxidative potential for a bolus injection of dopamine and measured by WINCS. Increasing current corresponds to increasing dopamine concentration (0.25, 1, 2.5, 5, and 10 µM). B. Background subtracted voltammograms determined by WINCS. As in A., increasing current corresponds to increasing dopamine concentration (0.25, 1, 2.5, 5, and 10 µM). C. Dopamine calibration curves collected by WINCS (open circles) and UEI (closed circles). The line describes the best linear fit.

FIG. 13 shows concentration-dependent responses measured with flow injection analysis. Single responses to varying concentrations of dopamine (0.25, 1, 2.5, 5 and 10 μM) and collected at the same CFM by WINCS are shown in FIG. 13A. The increase in current with each increase in dopamine concentration was noted. Background subtracted cyclic voltammograms collected during the plateau of these responses are shown in FIG. 13B. The increasing size of the oxidative and reductive peaks with increasing dopamine concentration also was noted. FIG. 13C compared concentration-response curves generated by WINCS (solid circles) and UEI (open circles). Current was measured at the plateau response and represented the average of triplicate measurements. Both systems recorded a similar linear dependence of measured oxidative current with dopamine concentration. The correlation coefficient (r2) was 0.994 for WINCS and 0.977 for UEI. All measurements were collected at the same CFM. Similar dopamine concentration-response curves were also recorded at three additional CFMs for both systems.

Figure 14:
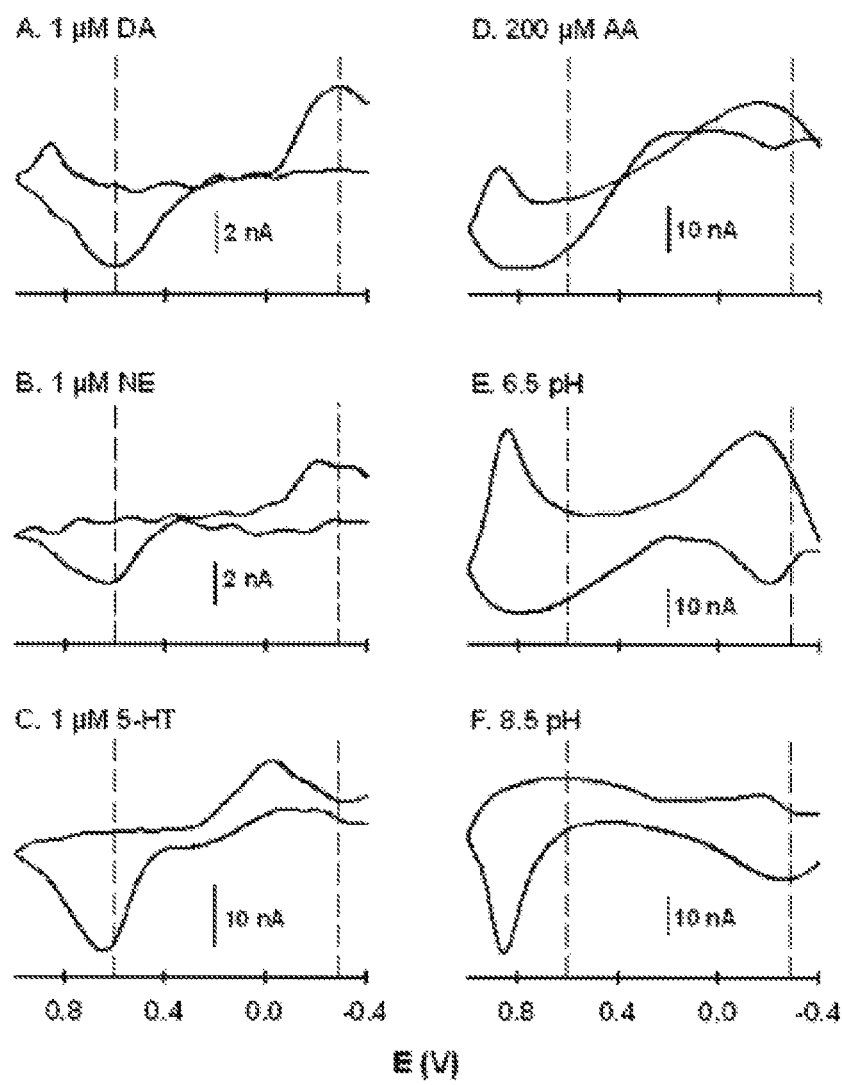
FIG. 14. Comparison of background subtracted cyclic voltammograms for different analytes. A. 1 µM dopamine (DA). B. 1 µM norepinephrine NE). C. 1 µM serotonin (5-HT). D. 200 µM ascorbic acid (AA). E. Acidic pH change (6.5 pH). F. Basic pH change (8.5 pH).

Sample background subtracted cyclic voltammograms for different analytes and collected by WINCS are shown in FIG. 14. These voltammograms, which have been described elsewhere (Baur et al., *Anal. Chem.*, 60:1268-1272 (1988); Jackson et al., *Anal. Chem.*, 67:1115-1120 (1995); and Kawagoe et al., *J. Electroanal. Chem.*, 359:193-197 (1993)), illustrate some of the capabilities of FSCV for resolving chemical signals. These analytes were also considered "interferents" to the voltammetric measurement of dopamine in the brain, because all would contribute to current monitored at the oxidation potential for dopamine if present. FIGS. 14A, B and C show voltammograms for the catecholamines dopamine and norepinephrine, and the indoleamine serotonin, respectively, at 1 µM. Dopamine and norepinephrine, which differ by a single hydroxyl group on the side chain attached to the catechol ring, gave similar voltammograms. In contrast, the voltammogram for the indoleamine, serotonin, was distinguished from these two catecholamines by the sharper oxidative peak and in particular, the less negative reductive peak. Serotonin, because it adsorbs more readily to the CFM surface, also gave more oxidative current than both dopamine and norepinephrine at the same concentration. Similarly, dopamine provided slightly more oxidative current than norepinephrine.

FIGS. 14D, E and F compared voltammograms for 200 µM ascorbic acid (Vitamin C), an acidic pH change, and a basic pH change, respectively. All three, as well as the dopamine metabolites homovanillic acid and 3,4-dihydroxyphenylacetic acid (Baur et al., *Anal. Chem.*, 60:1268-1272 (1988)), can readily be distinguished from dopamine. Ascorbic acid, which is found in high 0.5 mM concentrations in the brain, has been considered the primary interferent to the voltammetric determination of dopamine (Robinson et al., *Chem. Rev.*, 108:2554-2584 (2008)). Brain pH, which changes as a result of altered neuronal activity, is also an interferent for monitoring dopamine with FSCV in vivo.

In Vivo FSCV at a CFM

The electrically evoked release of dopamine in the striatum of the urethane-anesthetized rat was used to compare FSCV measurements collected by WINCS and UEI in vivo. Recordings shown in FIG. 15A were collected at the same CFM and striatal location during MFB stimulation with a high-frequency (60 Hz), 2-s pulse train delivered at 5 s. The increase in dopamine levels during the stimulation reflects exocytotic neurotransmitter release elicited by action potentials, activated when electrical current is applied to ascending dopaminergic fibers in the MFB and arriving at the dopaminergic terminals in the striatum (Wu et al., *J. Neurosci. Methods*, 112:119-133 (2001)). The return of dopamine levels to baseline was due to the action of the dopamine transporter translocating released dopamine back into the dopaminergic terminal in the process of neuronal uptake. The similar kinetics of the evoked response recorded by WINCS (red) and UEI (black) and background subtracted dopamine voltammograms generated by the two systems (FIG. 15B) were noted.

Figure 15:
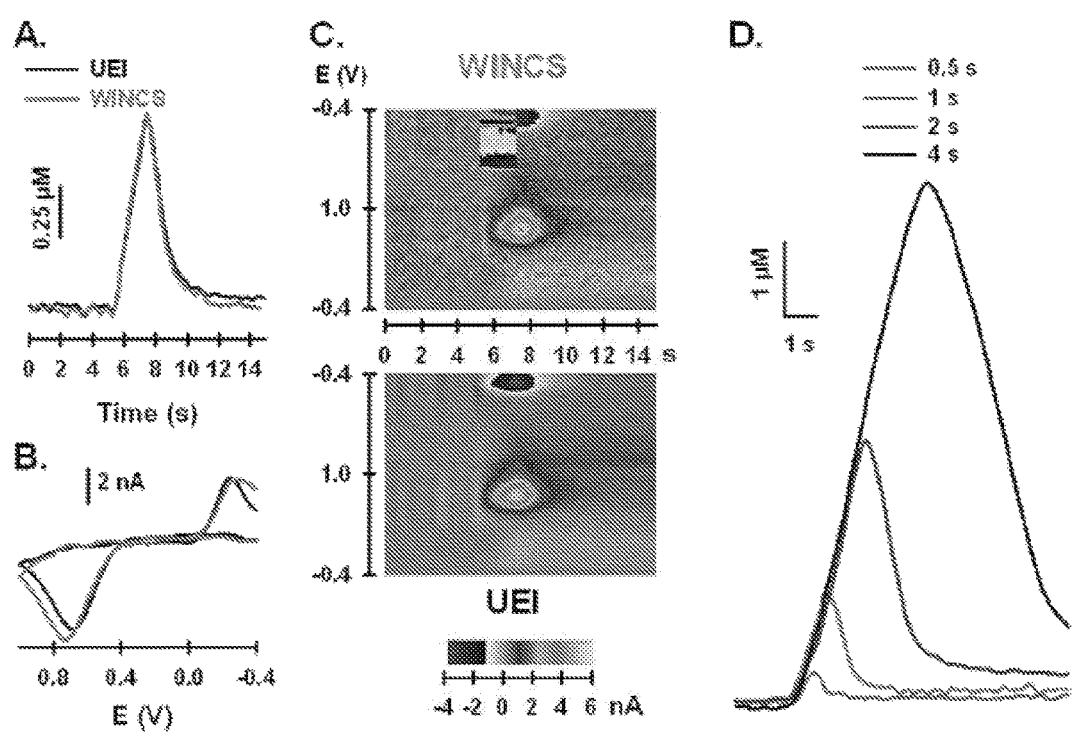
FIG. 15. In vivo comparison of WINCS and UEI. A. Electrically evoked dopamine levels measurement in the striatum by WINCS (gray) and UEI (black). B. Background subtracted cyclic voltammograms measured by WINCS (red) and UEI (black). C. Pseudo-color plots measured by WINCS (top panel) and UEI (bottom panel). D. Electrically evoked dopamine levels measured in the striatum by WINCS and elicited by pulse trains of different duration (0.5, 1, 2, 4 sec represented as the smallest to the largest response, respectively.

Shown in FIG. 15C, pseudo-color displays describing the evoked recordings were also quite similar for the two systems. UEI was noted to have slightly lower noise levels than WINCS, which exhibits a more wavy appearance of the brown background in the pseudo-color plot. There was an additional feature in the WINCS plot (top panel), near the reductive current for dopamine. This feature reflected a stimulus artifact, and it appeared randomly in the pseudo-color display during the stimulation period because pulse trains were not synchronized to the voltage scan in this device. No stimulus artifact was observed in the UEI recording (bottom panel), because this system generated both the voltage scan and the stimulus pulses, and synchronizes the two so that they were not applied at the same time. Nevertheless, the stimulus artifact did not interfere with the evoked recording and voltammogram collected by WINCS and shown in FIGS. 14A and B, respectively. The effect of pulse-train duration (0.5, 1, 2 and 4 s) on evoked dopamine responses recorded by WINCS is shown in FIG. 14D. These recordings, demonstrating an increase in extracellular dopamine levels with train duration, were collected at the same CFM and location in the striatum. None of the responses were distorted by stimulus artifact. Comparable results were obtained in three additional rats.

In Vitro Noise Analysis

Figure 16:
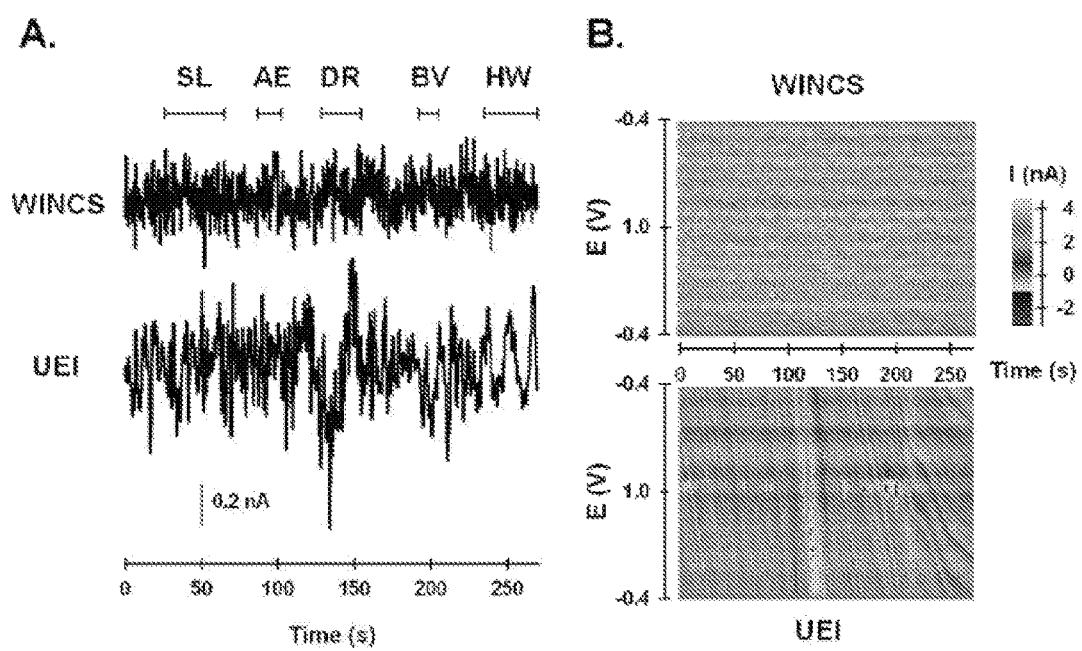
FIG. 16. Noise analysis comparison of WINCS and UEI in large-animal operating room. A. Current measured at a typical oxidative potential (0.6 V) for dopamine, plotted with time and monitored by WINCS (top panel) and UEI (bottom panel). Abbreviations: SL, surgical lights; AE, anesthesia equipment; DR; trephine drill; BV, "Bovie" cauterization unit; HW, hand waving. B. Pseudo-color plots measured by WINCS (top panel) and UEI (bottom panel).

To evaluate susceptibility to electromagnetic interference, "dry" measurements collected by WINCS and UEI were compared in an operating room for large-animal surgeries. A dummy cell, a simple resistor-capacitor circuit mimicking the electrical properties of a CFM, was connected to each system and placed on the surgical table within two feet of each other. Various electrical devices normally utilized during functional neurosurgery were turned on and off sequentially to evaluate noise perturbations. FIG. 16A shows measured current at what would be the typical dopamine oxidative potential (0.6 V) at a CFM with respect to time for WINCS (top panel) and UEI (bottom panel). Pseudo-color plots for these same recording are shown for WINCS (top panel) and UEI (bottom panel) in FIG. 16B. Noise levels of WINCS in the operating room were lower than those of the UEI. Increased noise levels recorded by the UEI were indicated by the larger peak-to-peak amplitude of baseline current (FIG. 16A) and the wavy features in the pseudo-color plot (FIG. 16B). Moreover, powering the trephine drill (DR) and cauterizing unit (BV), and hand waving (HW) over the dummy cell all caused distortion in the current trace and pseudo-color plot for the UEI, while WINCS was largely unaffected. Drill powering caused the greatest distortion. Little distortion was recorded in either system by turning on surgical lights (SL) or powering the anesthesia equipment (AE).

Taken together, these results demonstrate that WINCS is well suited for intraoperative neurochemical monitoring. Neurotransmitter measurements at an implanted chemical sensor can prove useful for advancing functional neurosurgery.

Example 3

Wireless Instantaneous Neurotransmitter Concentration System (WINCS)-Based Amperometric Detection of Dopamine, Adenosine, and Glutamate for Intraoperative Neurosurgical Monitoring Materials and Methods WINCS Hardware Configuration A WINCS device, shown in FIG. 17A, incorporated a transimpedance amplifier and associated analog circuitry for electrochemistry, a microprocessor with a dual analog-to-digital converter (ADC) and digital-to-analog (DAC) ports, and a Bluetooth® transceiver, all on a single rechargeable lithium-polymer battery-powered multilayer printed circuit board. The device can be packaged in a sterilizable polycarbonate case (FIG. 17B).

WINCS in the FPA mode utilized one of the microprocessor's DACs to apply a fixed potential to a CFM or enzyme-linked biosensor. Sensor current was converted to a voltage at 1 KHz by the transimpedance amplifier, converted to a digital data stream by one of the microprocessor's ADCs, and then wirelessly transmitted to the WINCS support station. The support station included a Windows-XP laptop running custom software that remotely (wirelessly) controls the parameters and operation of WINCS, such as starting and stopping data acquisition and transmission, modifying the applied fixed potential, and changing the sampling rate. FPA data were saved to disk as a sequence of unsigned two-byte integers, a format suitable for post-processing by various software applications, such as MATLAB® (The MathWorks, Inc., Natick, Mass., USA) or LabVIEW (National Instruments, Austin, Tex., USA).

Fixed Potential Amperometry

FPA recordings performed in a two-electrode configuration with WINCS were compared to those obtained by a commercially available hardwired electrochemical recording system (eDAQ Pty Ltd, Colorado Springs, Colo., USA) consisting of a potentiostat (EA161 Picostat®) in conjunction with an analog-to-digital signal converter-recorder (E-Corder®) run by Chart® software. FPA performed with a CFM was used to test WINCS reliability by measuring dopamine in vitro or electrically-evoked dopamine release in vivo. During these experiments the applied potential was held at +0.8 V versus an Ag/AgCl reference/counter electrode.

Commercially available biosensors sensitive to adenosine (Sarissa Biomedical, Coventry, United Kingdom) and glutamate (Pinnacle Technology Inc., Lawrence, Kans.) were used to test the capability of WINCS to measure these molecules. These sensors consisted of a platinum wire coated with one or more enzymes and a selective permeable membrane to block potential electroactive interfering compounds. Glutamate is converted by the enzyme glutamate oxidase to α-ketoglutarate generating hydrogen peroxide that is subsequently oxidized at the platinum surface producing an amperometric signal whose magnitude is directly proportional to the concentration of the analyte. Adenosine deaminase converts adenosine to inosine by removal of an amino group. Inosine is subsequently converted to hypoxanthine by the enzyme nucleoside phosphorylase with the removal of the ribose ring. Xanthine oxidase subsequently oxidizes hypoxanthine to xanthine and further to uric acid with the production of hydrogen peroxide. Hydrogen peroxide at the adenosine sensor is oxidized in a similar manner as the glutamate sensor producing an amperometric signal. For both in vitro and electrically-evoked release in vivo, the applied potential was set to values indicated by the manufacturers of each sensor (+0.5 V and +0.6 V for adenosine and glutamate, respectively).

In Vitro Testing of WINCS-Based FPA
Analysis of Electromagnetic Interference

To evaluate the susceptibility of WINCS-based FPA recordings to electromagnetic interference, measurements were collected by WINCS and compared to those obtained simultaneously with the eDAQ system in a hospital neurosurgical operating room. A dummy cell consisting of a standard 100+1% MΩ resistor was connected to each system and placed on the operating room surgical table within 30 cm of each other. A fixed potential of +0.8 V was applied to the dummy cell and various electrical devices normally utilized during functional neurosurgery were turned on and off sequentially to evaluate noise perturbations. Oxidation current dynamics recorded in vivo by FPA are slow enough to permit 10 Hz low-pass filtering to reduce noise while preserving the signal of interest. Thus, to mimic the filter settings typically used for in vivo testing (described below), the FPA signals recorded from the dummy cell with WINCS and the eDAQ system were also filtered at 10 Hz.

In Vitro Calibration of CFMs and Enzyme-Linked Biosensors

Prior to their use in vivo, flow injection analysis was used with both WINCS and the commercial eDAQ system for in vitro FPA calibration of CFMs for dopamine. In this well-established procedure for device testing and sensor calibration (Kristensen and Wightman, *Anal. Chem.*, 58:986-988 (1986)), a CFM was positioned in the center of a Plexiglas reservoir (flow cell) in which a flowing stream of physiological buffer at room temperature (0.01M phosphate-buffered saline, PBS, pH=7.6) was pumped at a constant rate of 4 mL/min. An electronic valve allowed a 1 mL volume loop containing 2.5, 5, or 10 μM of dopamine hydrochloride (Sigma-Aldrich, St. Louis, Mo.) to be injected into the flowing stream of buffer for 5 sec. An Ag/AgCl reference/counter electrode positioned on the periphery of the reservoir in contact with the buffer solution completed the two-electrode system.

Using the commercially available enzyme-linked biosensors for glutamate and adenosine, in vitro WINCS-based FPA measurements of various concentrations of these substances were performed at room temperature prior to their use in vivo. Using similar calibration protocols specified by the respective manufacturers of these sensors, 5 mL of a 50 μM adenosine (Sigma-Aldrich, St. Louis, Mo.) solution was added to a beaker containing 20 mL of PBS to provide a single 10 μM steps in adenosine concentration. Glutamate sensitivity was assessed by adding 250 μL of a 5 mM L-glutamate (Sigma-Aldrich, St. Louis, Mo.) solution to a 25 mL volume of PBS stirred with a magnetic stirrer for three 50 μM steps in glutamate concentration.

In Vivo Testing of WINCS-Based FPA
Animals

Five adult male Sprague-Dawley rats (300-400 g) were used to record electrically-stimulated release of dopamine (n=4) and adenosine (n=1). One female pig (25 kg) was used for in vivo glutamate recordings. The animals were housed under standard conditions with access to food and water ad libitum. Care was provided in accordance with NIH and local institutional (IACUC) guidelines.

Dopamine Recordings

Rats were anesthetized with urethane (1.5 g/kg i.p.; Sigma-Aldrich, St. Louis, Mo.) and then mounted onto a commercially available stereotaxic frame (David Kopf Inc., Tujunga, Calif., USA). Multiple burr holes were drilled for implantation of the reference/counter, stimulating, and CFM. Stereotaxic coordinates were obtained from a standard rat atlas using a flat skull orientation and the bone suture landmark bregma as the reference point. A bipolar stimulating electrode (Plastics One, MS 303/2, Roanoke, Va., USA) with the tips separated by 1 mm was placed within the medial forebrain bundle (MFB) containing dopaminergic axons (coord. in mm: anterior-posterior [AP] −4.6; medial-lateral [ML] +1.2; dorso-ventral [DV] −8.0 from dura). The CFM was positioned in the dorsomedial striatum (coord. in mm: AP +1.2; ML +2.0; DV −4.6 to −6.0 from dura and adjusted to obtain a robust stimulation-evoked FPA signal). The reference/counter electrode was inserted into superficial cortical tissue contralateral to the CFM and stimulating electrode. Electrical stimulation of the MFB consisted of a train of 60 Hz monophasic pulses (900 μAmps, 2 ms pulse width) applied for 1, 2 or 4 sec via an optical isolator and programmable pulse generator (Iso-Flex/Master-8; AMPI, Jerusalem, Israel). Stimulation of the MFB was applied three times every 30 sec and the responses averaged.

In some animals, the same surgical procedure and stimulation parameters were used to compare WINCS-based FPA and FSCV recordings of MFB stimulation-evoked dopamine release. This recording procedure differs from FPA in that the potential between the CFM and reference/counter electrode was cycled 10 times a second using a triangle wave between −0.4 V up to +1 V and back to −0.4 V at a speed of 300 V/sec. The current recorded during a potential sweep yielded a combination of capacitive and Faradaic (oxidation/reduction) current. A sufficient number of potential sweeps were averaged before stimulation to yield a baseline template that was then subtracted from every subsequent sweep to obtain Faradaic currents corresponding to the unique electrochemical signal of dopamine oxidation and reduction (see FIG. 20D inset). Thus, the heights of the peaks in background subtracted voltammograms were directly proportional to the concentration of dopamine oxidized and reduced at the CFM surface. The peak heights of dopamine oxidation, in turn, were displayed with respect to time and, together with the peak heights of dopamine reduction, graphed in a pseudo-color plot (see FIG. 20D top and bottom panel, respectively). These measures provided enhanced selectivity of FSCV, compared to FPA, for recording real-time, chemically resolved changes in dopamine at CFMs in freely moving animals.

Adenosine Recordings

A similar procedure described above was used to prepare rats for in vivo testing of WINCS with the adenosine biosensor. Electrical stimulation was delivered through a scaled-down version of a typical DBS electrode composed of four-ring contacts along the electrode shaft (0.28" diameter, four contacts 0.02" in size, with 0.02" spacing between contacts). The tips of the stimulating electrodes and sensor probes were mounted within 0.5 mm of each other on a single stereotaxic electrode carrier with the biosensor's tip midway between contacts 1 and 2 of the stimulating electrode. The stimulating electrode was implanted on the border of the ventrolateral (VL) thalamus (coord. in mm: −2.4 AP, +2.2 mL, −6.0 DV from dura) and the adenosine sensor more medial and thus in the VL. The reference/counter electrode was placed in superficial contact with cortical tissue contralateral to stimulating and recording electrodes. After achieving a stable baseline signal, monophasic 0.1 msec constant current pulses were applied for 10 sec durations across the DBS electrode contacts 0 (negative) and 3 (positive) at various current intensities (0.5-2 mA) and fixed frequency (100 Hz) and at various frequencies (50-200 Hz) and fixed intensity (1 mA). Pre-in vivo calibration of the adenosine biosensor with the protocol described above was used to convert oxidation current recorded in vivo to adenosine concentrations.

Glutamate Recordings

Under the care of a certified veterinarian technician the pig was sedated with a combination of telazole and xylazine (5-6 mg/kg and 2 mg/kg i.p., respectively; Mayo Clinic Pharmacy, Rochester, Mich.) prior to intubation. Continuous anesthesia was maintained with isoflurane (1%; Mayo Clinic Pharmacy, Rochester, Mich.) for the rest of the procedure. The pig was then placed into an in house-built MRI compatible stereotaxic frame followed by a midline scalp incision and craniotomy to expose part of the left motor cortex. A Medtronic 3389 DBS lead mounted onto a stereotaxic electrode holder was used as the stimulating electrode. The glutamate sensor was secured to the same holder within 0.5 mm of the stimulating electrode and with its sensing cavity positioned between contacts 1 and 2. The two were then lowered vertically until all stimulating electrode's contacts were inserted into the cortex. After achieving a stable baseline signal, monophasic 100 μsec constant current pulses were applied for 10 sec at various current intensities (0.5-2 mA, 100 Hz, contact 0 positive and 3 negative). Pre-in vivo calibration of the glutamate biosensor with the protocol described above was used to convert oxidation current recorded in vivo to glutamate concentrations.

Results

In Vitro Testing of WINCS-Based FPA

Analysis of Electromagnetic Interference

Figure 18:
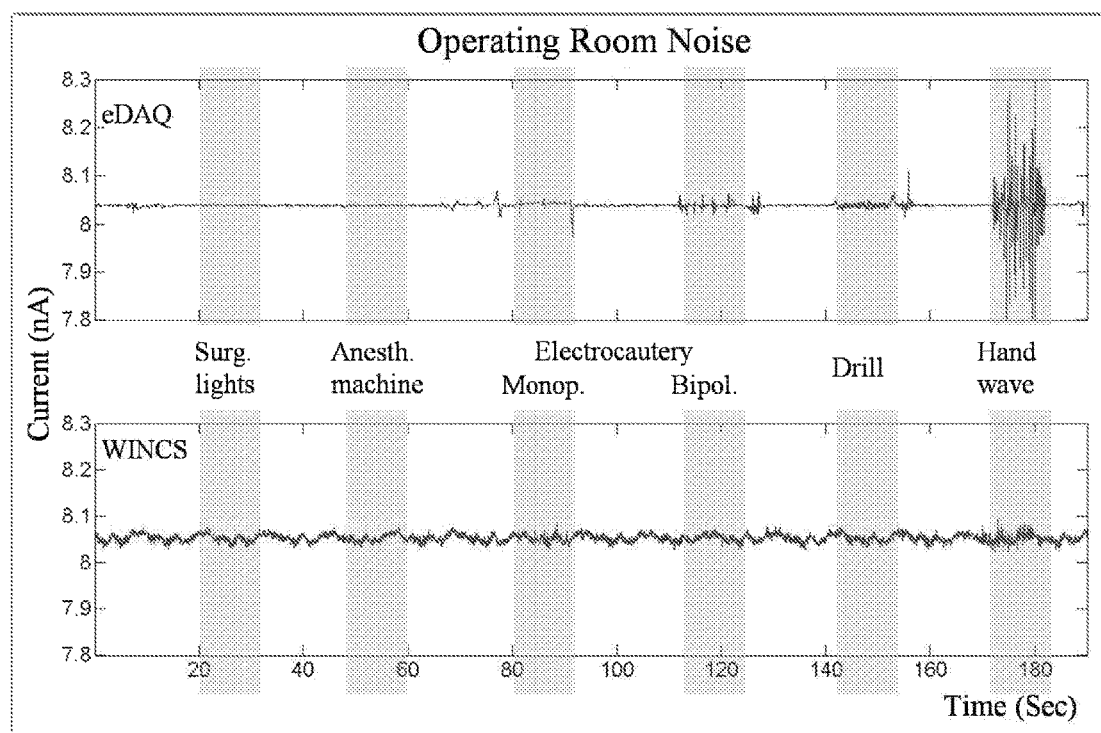
FIG. 18. Comparison of WINCS vs. eDAQ system for susceptibility to noise in the operating room environment during FPA. A 100 MΩ dummy cell was connected to each system and placed on the operating room surgical table within one foot of each other. Hand waving and electrical devices (surgical lights, anesthesia machine, electrocauterizer, and pneumatic hand drill), turned on (light bars) and off at variable intervals, were applied one foot above the dummy cell.

An average current of ~8 nA was recorded with both WINCS and the eDAQ system with an applied fixed potential of +0.8V across a 100 MΩ resistor (FIG. 18). The magnitude of the noise envelope recorded with WINCS appeared more marked then with the eDAQ system with a standard deviation, measured in the first 20 seconds of unperturbed recording, of +8.3 and +2.1 pA, respectively. Electrical interference created by activation of the electrocauterizer (monopolar and biopolar settings) or pneumatic drill evoked detectable disturbances in the baseline signal recorded with the eDAQ system that was difficult to detect in the higher average noise envelope recorded by WINCS. Turning on and off the overhead surgical lights had no significant impact on the baseline FPA signals recorded by either system. However, noise elicited by waving a hand over the dummy cell generated a significantly greater disturbance in the baseline signal recorded by the eDAQ system, compared to WINCS. WINCS has a resolution of 16 bits and a dynamic range larger than 1.2 mA needed to perform FSCV. As a consequence, the smallest current increment theoretically measurable in the absence of noise is ~19 pA. As a function of the standard deviation of the recorded baseline signal in this test, the effective resolution of the WINCS ADC was about 14 bits, allowing current measurements on the order of a few hundred pA. While higher resolution is always a desirable feature, the intrinsic noise levels of WINCS-based FPA recordings were found to be acceptable to measure oxidation currents both in vitro and in vivo (see below).

In Vitro Calibration of CFMs and Enzyme-Linked Biosensors

Figure 19:
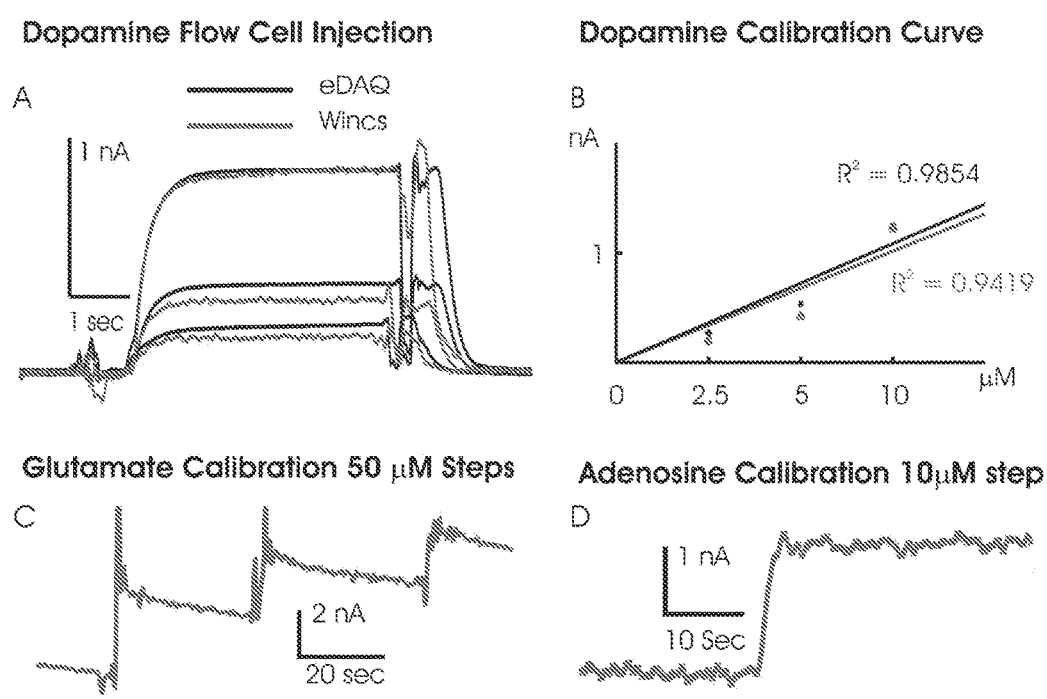
FIG. 19. A: 5 sec long bolus injections of 2.5, 5, and 10 µM dopamine across a single CFM in the flow cell measured with WINCS (gray line) and a hardwired potentiostat system (eDAQ, black line). B: Plot of dopamine oxidation current versus dopamine concentrations and linear regression analysis for both FPA recordings using WINCS (gray line) and the eDAQ system (black line). The perturbations in the amperometric signals occurring at the start and end of the 5 sec bolus injections of dopamine are a result of engaging and disengaging the electronic valve and do not interfere with the calibration assessments. C: WINCS Glutamate sensor calibration, oxidation current for three 50 µM glutamate concentration steps. D: Calibration of adenosine biosensor performed with a single 10 µM concentration step as measured with WINCS.

Both the magnitude and temporal dynamics of the FPA responses to 5 sec bolus applications of 2.5, 5.0, and 10 μM dopamine recorded at a single CFM in the flow injection system by WINCS were comparable to the eDAQ recording system (FIG. 19A). As shown in FIG. 19B, calibration curves generated from these data for dopamine concentration versus dopamine oxidation current were linear for both systems with a correlation coefficient of >0.94. In a similar fashion, linear FPA responses recorded by WINCS were also observed with step-wise increases in beaker concentrations of glutamate and adenosine (FIGS. 19C and 19D, respectively).

In Vivo FPA Testing of WINCS

Dopamine Recordings

Figure 20:
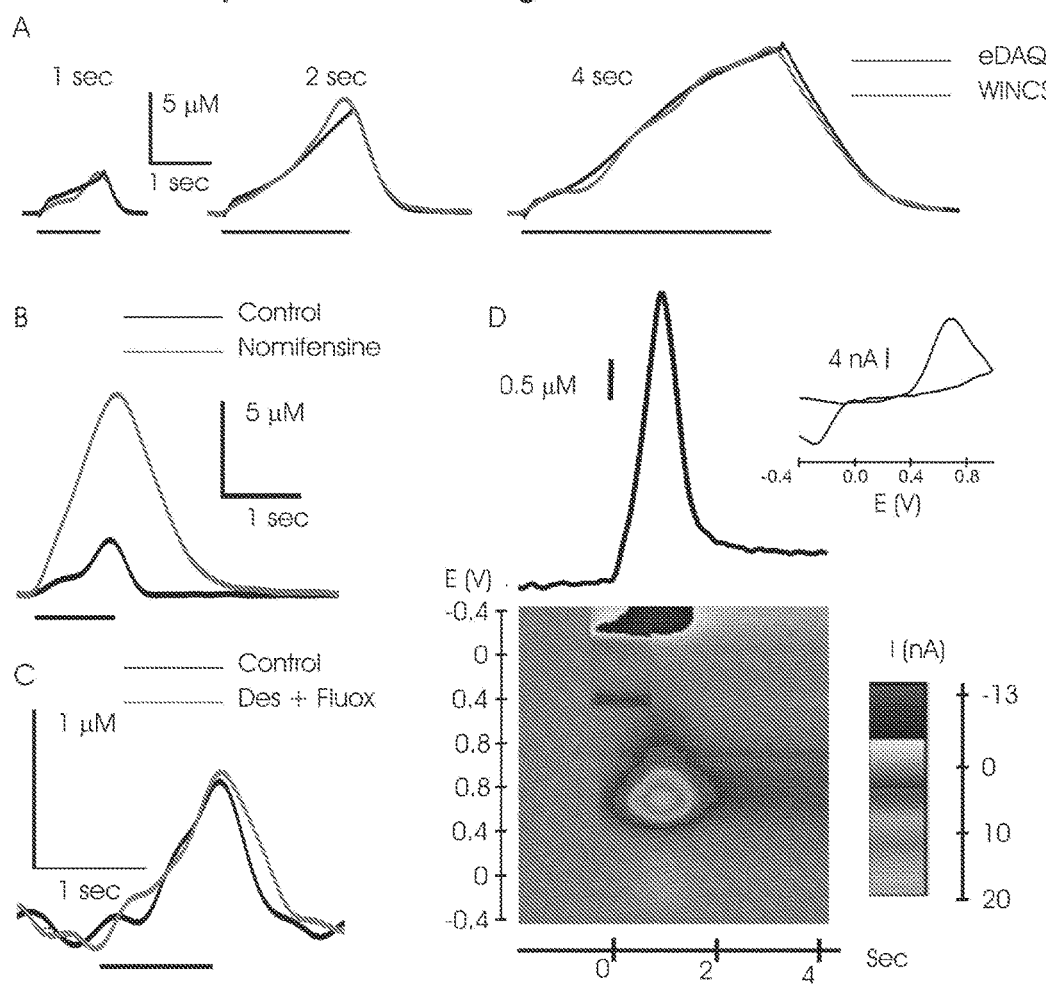
FIG. 20. A: Striatal dopamine release evoked by 1, 2 or 4 sec of 60 Hz MFB stimulation (horizontal black bars) as measured with WINCS (gray lines) and a hardwired system (eDAQ, black lines). B: Systemic administration of the dopamine reuptake inhibitor nomifensine induced an increase and delay in recovery of the evoked signal confirming the dopaminergic origin of the measured current. C: Systemic administration of the norepinephrine and serotonin reuptake inhibitors desipramine and fluoxetine, respectively, failed to increase the amperometric signal indicating a lack of interference from these two neurotransmitters in the striatum. D: Striatal dopamine release as measured with WINCS in FSCV mode during 1 second MFB stimulation. The oxidation and reduction peak potential as shown in the voltammogram (D: inset) and pseudo-color plot further indicates the FSCV signal corresponds to dopamine oxidation (spot in the middle) and reduction (spot toward the top) current.

As shown in a representative animal in FIG. 20A, DBS of MFB (60, 120, or 240 pulses at 60 Hz and 900 μA, n=4 rats) evoked a rapid increase in striatal dopamine oxidation current corresponding to stimulus time-locked increases in dopamine release. Upon cessation of each stimulation, the FPA signal returned rapidly to pre-stimulus levels as a result of terminal dopamine reuptake. Comparable FPA signals were recorded with both the WINCS and eDAQ system.

Systemic administration of the selective dopamine reuptake inhibitor nomifensine (10 mg/kg i.p.; n=2 rats) increased MFB stimulation-evoked dopamine oxidation current and delayed recovery to pre-stimulation baseline levels. A representative WINCS recording is shown in FIG. 20B. In contrast, combined systemic administration of the selective serotonin (fluoxetine) and norepinephrine (desipramine) reuptake inhibitors (10 mg/kg i.p. each; n=2 rats) failed to alter the magnitude or temporal pattern of the FPA signal evoked by MFB stimulation (FIG. 20C).

Further confirmation that WINCS-based FPA selectively recorded striatal dopamine release evoked by MFB stimulation is shown in FIG. 20D. In a separate rat, application of FSCV with WINCS during MFB stimulation (1 sec, 60 Hz, 2 ms pulse width) yielded a background subtracted voltammogram and pseudo-color plot that corresponded to the unique electrochemical signature of dopamine (FIG. 20D inset and bottom panel, respectively). A plot of the temporal profile of MFB-evoked dopamine release recorded at the CFM using FSCV also corresponded closely to the evoked response recorded with FPA (FIG. 20D top panel).

Adenosine Recordings

As recorded using an adenosine biosensor coupled with WINCS-based FPA, VL thalamic DBS resulted in delayed (20-25 seconds after beginning of stimulation) increases in hydrogen peroxide oxidation current corresponding to local increases in adenosine extracellular concentrations peaking ~1 min after cessation of the 10 sec stimulation with a return to baseline within 2.5 to 5 min (FIG. 21). To explore the relationship between current intensity and frequency of electrical stimulation and extracellular adenosine concentration, local changes in adenosine concentration in response to electrical stimulation of the VL thalamus at various current intensities (0.5-2.0 mA) and fixed frequency (100 Hz) and at various frequencies (50-200 Hz) and fixed intensity (1 mA) were tested. As shown in FIGS. 21A and 21B, adenosine extracellular concentrations increased proportionately with increasing levels of current intensity or frequency (n=4 stimulations at varying intensity or frequency in 1 rat). Adenosine concentrations were allowed to return to pre-stimulation baseline between stimulations.

Glutamate Recordings

To mimic human intraoperative neurosurgery an in-house constructed MRI-compatible stereotaxic frame for the pig was utilized to compare WINCS and eDAQ-based FPA recordings of MCS-evoked local glutamate release. Cortical 100 Hz stimulation of the pig motor cortex for 10 sec at 1 mA was delivered to the Medtronic 3389 DBS lead across contact 0 (negative) and 3 (positive). As shown in FIG. 22A, cortical stimulation evoked comparable increases in hydrogen peroxide oxidation currents corresponding to local glutamate release as recorded using a glutamate biosensor coupled with WINCS and the eDAQ system. To explore the relationship between current intensity of electrical stimulation and extracellular glutamate concentration, local changes in glutamate concentration in response to electrical stimulation of the motor cortex at various current intensities (0.5-2.0 mA) and frequency (100 Hz) were tested with WINCS. As shown in FIG. 22B, glutamate extracellular concentrations increased proportionately with increasing levels of current intensity. With respect to the start of stimulation and current intensities of 0.5, 1.0, 1.5, and 2.0 mA, peak oxidation currents were attained within 20, 30, 40, and 45 sec and returned to baseline within 90, 240, 300, and >360 sec, respectively. Glutamate concentrations were allowed to return to pre-stimulation baseline levels between stimulations.

By incorporating FPA, the chemical repertoire of WINCS-measurable neurotransmitters was expanded to include glutamate and other non-electroactive species for which the evolving field of enzyme-linked biosensors exist. As many neurotransmitters are not electrochemically active, FPA in combination with enzyme-linked microelectrodes (Table 1) represents a powerful intraoperative tool for rapid and selective neurochemical sampling in anatomical targets during functional neurosurgery.

TABLE 1

FPA compatible enzyme-linked microelectrodes for selective real-time monitoring of neurochemicals in mammalian brain.

| Analyte | Preclinical Applications | Enzyme (E) Reporter (R) |
|---|---|---|
| Glutamate (Glu) | HFS-evoked Glu release and clearance in vivo (Lee et al., Eur. J. Neurosci., 23: 1005-1014 (2006)). Glu transmission after traumatic brain injury (Hascup et al: Determining the source of resting and physiologically-evoked L-glutamate levels using enzyme-based microelectrode arrays in awake rats, in Phillips PEM, Sandberg SG, Ahn S, Phillips AG (ed): proceeding of the 12th international conference on in vivo methods 2008. University of British Columbia, Vancouver, Canada. 2008). KCl-induced Glu release in vivo and in vitro (Burmeister et al., J. Neurosci. Methods, 119: 163-171 (2002) and Pomerleau et al., Ann. N.Y. Acad. Sci., 1003: 454-7 (2003)). Ketamine-induced Glu release in behaving rats (Aillon et al.: Near real-time measurement of glutamate concentration using biosensors in place of traditional methodologies, in Phillips PEM, Sandberg SG, Ahn S, Phillips AG (ed): proceeding of the 12th international conference on in vivo methods 2008. University of British Columbia, Vancouver, Canada. 2008). Prefrontal glutamate release evoked by PCP local infusions (Konradsson et al.: Second-by-second measurement of stimulated glutamate release and its modulation by α7 and mGlu 2/3 receptors: relevance to schizophrenia, in Phillips PEM, Sandberg SG, Ahn S, | E: Glutamate oxidase R: Hydrogen peroxide |

TABLE 1-continued

FPA compatible enzyme-linked microelectrodes for selective real-time monitoring of neurochemicals in mammalian brain.

| Analyte | Preclinical Applications | Enzyme (E) Reporter (R) |
|---|---|---|
| | Phillips AG (ed): proceeding of the 12th international conference on in vivo methods 2008. University of British Columbia, Vancouver, Canada. 2008). Alterations in Glu neurotransmission after traumatic brain injury (Hinzman et al.: Alterations in glutamate neurotransmission after traumatic brain injury: Study using enzyme-based microelectrode arrays, in Phillips PEM, Sandberg SG, Ahn S, Phillips AG (ed): proceeding of the 12th international conference on in vivo methods 2008. University of British Columbia, Vancouver, Canada. 2008). | |
| GABA | Detection of exogenous GABA in vivo (Burmeister et al.: Advances in the in vivo detection of GABA using enzyme coated microelectrode arrays, in Phillips PEM, Sandberg SG, Ahn S, Phillips AG (ed): proceeding of the 12th international conference on In Vivo methods 2008. University of British Columbia, Vancouver, Canada. 2008). | $E_1$: γ-Aminobutyric glutamate transaminase<br>$E_2$: Succinic semialdehyde dehydrogeanse<br>$E_3$: Glutamate oxidase<br>R: Hydrogen peroxide |
| Adenosine | DBS-elicited release of adenosine in thalamus in vivo (Bekar et al., *Nat. Med.*, 14: 75-80 (2008)). Release from spinal cord during locomotion in vivo (Llaudet et al., *Biosens. Bioelectron.*, 18: 43-52 (2003)). Release from brainstem during cardiorespiratory and defense reflexes in vivo (Dale et al., *J. Physiol.*, 544(Pt 1): 149-160 (2002) and Gourine et al., *J. Physiol.*, 544: 161-70 (2002)). | $E_1$: adenosine deaminase<br>$E_2$: nucleoside phosphorylase<br>$E_3$: xanthine oxidase<br>R: Hydrogen peroxide |
| Acetylcholine/ Choline | Detection of exogenous choline and endogenous cholinesterase activity in vivo (Garguilo and Michael, *J. Neurosci. Methods*, 70: 73-82 (1996) and Mitchell, *Anal. Chem.*, 76: 1098-106 (2004)). | $E_1$: Acetylcholine esterase<br>$E_2$: Choline oxidase<br>R: Hydrogen peroxide |
| Glucose | Glucose levels in striatum in freely moving rats (Lowry et al., *J. Neurosci. Methods*, 79: 65-74 (1998)) and in cortex during sleep/wake cycle (Netchiporouk et al., *Eur. J. Neurosci.*, 13: 1429-1434 (2001)). Effect of anesthesia on glucose levels in vivo (Lowry and Fillenz, *Bioelectrochemistry*, 54: 39-47 (2001)). Correlations of EEG/EMG activity with fluctuations in cortical glucose levels (Naylor et al: A new technique for the simultaneous recording of electroencephalograph activity and CNS biosensor data, in Phillips PEM, Sandberg SG, Ahn S, Phillips AG (ed): proceeding of the 12th international conference on in vivo methods 2008. University of British Columbia, Vancouver, Canada. 2008). | E: Glucose oxidase<br>R: Hydrogen peroxide |

Example 4

FSCV can Detect Concentration Changes of Cations Using a Wireless Instantaneous Neurotransmitter Concentration System (WINCS)

FSCV with WINCS/Electrode Construction

The development of the WINCS hardware that integrates FSCV and digital telemetry for real-time electrochemical measurements was performed as described herein (see, also, Bledsoe et al., *J. Neurosurg.*, 111(4):712-723 (2009)). In general, WINCS included front-end analog circuitry for FSCV, a Bluetooth transceiver, a microprocessor, and a direct-current rechargeable lithium-polymer battery on a single unifying multiplayer printed circuit board, secured in a case made of polycarbonate for sterilization using the Sterrad® gas plasma process.

For its FSCV mode, WINCS used a transimpedance amplifier and a difference amplifier in order to interchange current-to-voltage and to deduct a triangular waveform potential on a CFM before signal digitization. A digital-to-analog converter transferred FSCV waveform to the CFM, and an analog-to-digital converter collected FSCV samples at a rate of 100 kilosamples per second. Bluetooth 2.4 to 2.5 GHz digital telemetry allowed for wireless communication between WINCS and a base-station computer running custom software on Windows-XP. This custom software maneuvered WINCS parameters and applications that are responsible for data acquisition and transmission, data sampling rate, and the applied potential waveform. Data were saved in the form of succession of unsigned two-byte integers to the Windows-XP base-station computer hard drive for later off-line examination by either MATLAB® (The MathWorks Inc., Natick, Mass., USA) or LabVIEW (National Instruments, Austin, Tex., USA).

FSCV incorporated a linear potential ramp transferred to the CFMs every 0.1 seconds, ranging from −0.4V to +1.5V at a scan rate of 400V/s (see, e.g., Swamy et al., *Anal. Chem.*, 79:744-750 (2007)). Under this circumstance, the period of the potential waveform scan during electrochemical measurement was 9.5 ms. The CFM was fixed at a bias potential of −0.4V in between scans. The carbon-fiber microelectrodes were assembled by aspirating a single polyacrylonitrile-based carbon fiber (T300, Amoco Inc., Greenville, S.C.; diam. 5 μM) into a glass capillary. The capillary was pulled to divide it into two electrodes with carbon fibers at their microscopic tips. The exposed carbon fiber was trimmed with a scalpel to a length equal to or less than 50 μM, under the microscope. Ag/AgCl reference electrodes were made by chloridizing a 31 g Teflon-coated silver wire (World Precision Instruments, Sarasota, Fla., USA) as described elsewhere (Garris et al., *J. Neurochem.*, 68:152-161 (1997)).

Flow Injection Analysis

Flow injection analysis was used for in vitro FSCV calibration of the CFMs in solutions of $Ca^{2+}$ and $Mg^{2+}$ as described elsewhere (Kristensen and Wightman, *Anal. Chem.*, 58:986-988 (1986)). The carbon-fiber electrode was positioned in a flowing stream of buffer solution (150 mM sodium chloride and 12 mM Tris-base buffer at a pH 7.4), which was pumped through the flow cell at 120 mL/hour, using a syringe pump (Harvard Apparatus model 11) and 1 mL of analyte ($Ca^{2+}$ and $Mg^{2+}$) was injected as a bolus. The CFMs were cycled in the experimental waveform, ranging from −0.4 to 1.5V at 400V/s with 10 Hz for at least 20 minutes before injecting analyte to stabilize the background current. During the experiment, an Ag/AgCl reference electrode was fixed on the side of a chamber and immersed in buffer solution. An electronic 1 mL loop injector was used to pump the bolus of analyte for 10 seconds into the flowing stream at defined analyte test concentrations.

Chemicals

Adenosine, $CaCl_2$, and $MgCl_2$ were purchased from Sigma-Aldrich (St. Louis, Mo.). $CaCl_2$, and $MgCl_2$ were dissolved with electronic-pure water to make 1 M and 100 mM stock solutions, respectively. Each of these stock solutions was diluted with Tris-buffer solution before it was injected into the flow cell. Solutions of four different concentrations were made with a limit at the known basal physiological extracellular concentrations of $Ca^{2+}$ and $Mg^{2+}$, which are 2 mM and 1 mM. These four different concentrations for $Ca^{2+}$ were 800 μM, 0.5 mM, 1 mM, and 2 mM. These same four concentrations were also used for $Mg^{2+}$, and, though its known basal physiological extracellular concentration is 1 mM, the 2 mM $Mg^{2+}$ solution served as a comparison to the $Ca^{2+}$ solution.

Results $Ca^{2+}$ Cyclic Voltammetry by WINCS In Vitro

The results from the very first fast-scan cyclic voltammetry of $Ca^{2+}$ at a known concentration (2 mM) in sub-second temporal resolution, using WINCS with an applied potential from −0.4V to +1.5V, was recorded (FIG. 28A-C). The bolus of analyte was injected through the flow injection analysis system 15 times. A pseudo-color plot was created by WINCS custom software (FIG. 28A). Time was plotted on the x-axis, and the applied electrode potential was plotted on the y-axis with a color gradient (in grayscale) that describes the current detected at the CFM (FIG. 28A). At approximately −0.4V, a light-brown color illustrating background current changes to dark blue and white for 10 seconds of injection of $Ca^{2+}$ into the flow cell, expressing a reductive current, was observed. At approximately +0.5V, +1.5V, and the returning −0.4V, a light-brown color, which again represents background current, altered to green and purple for 10 seconds of $Ca^{2+}$ injection into the flow cell, showing an oxidative current. FIG. 28B shows the cyclic voltammogram obtained when $Ca^{2+}$ is first detected, where the line that starts with a reduction peak near −0.4V indicates the forward-going potential from −0.4V to +1.5V. FIG. 28C shows one of the oxidative peaks at the switching potential 1.5V for the duration of injection. FIG. 28D shows that the initial cyclic voltammogram in the absence of $Ca^{2+}$ resulted in a large background charging current at the CFM by the rapid scanning of the potential and addition of 2 mM $Ca^{2+}$ increased the background current modestly.

FIG. 28E illustrates WINCS-recorded fast-scan cyclic voltammetry of 2 mM $Ca^{2+}$ with an applied potential from −0.4V to +1.0V. The pseudo-color plot was produced by WINCS custom software, plotting time on the x-axis and the applied electrode potential on the y-axis with the color gradient (in grayscale). At approximately −0.15V, a light-brown color portraying background current changes to dark blue and white for 10 seconds of injection of $Ca^{2+}$ into the flow cell, indicating a reductive current, was observed. At approximately +0.5, +1.0, and the returning 0.10V, a light-brown color turned to green and purple for 10 seconds of the injection, showing an oxidative current. FIG. 28F illustrates the cyclic voltammogram acquired when $Ca^{2+}$ was first detected, where the line that starts with a reduction peak near −0.15V is the forward-going potential from −0.4V to +1.5V.

FIG. 29A depicts WINCS-collected FSCV pseudo-color plots for increasing concentrations (0.0 mM, 0.5 mM, 1.0 mM, and 2 mM) of $Ca^{2+}$. FIG. 29B shows a current versus time plot with oxidative peaks of the three different concentrations of $Ca^{2+}$ at 1.5V and a strong linear relationship among the oxidative currents at the switching potential 1.5V versus $Ca^{2+}$ concentrations examined (0.0 mM to 2 mM; n=4 injections per concentration). Its linear correlation coefficient ($r^2$) was 0.99. The $Ca^{2+}$ calibration curve information was as follows:

Best-fit values
  Slope=13.80±0.5682
  Y-intercept (when X=0.0)=4.117±0.7516
  X-intercept (when Y=0.0)=−0.2984
  1/slope=0.07249
95% Confidence Intervals
  Slope=12.45 to 15.14
  Y-intercept (when X=0.0)=2.339 to 5.894
  X-intercept (when Y=0.0)=−0.4911 to −0.1338
Goodness of Fit
  $r^2$=0.9883
  Sy.x=1.063
Is slope significantly non-zero?
  F=589.5
  DFn, DFd=1.000, 7.000
  P value<0.0001
  Deviation from zero? Significant
Data
  Number of X values=3
  Maximum number of Y replicates=3
  Total number of values=9
  Number of missing values=0

$Mg^{2+}$ Cyclic Voltammetry by WINCS In Vitro

Fast-scan cyclic voltammetry of $Mg^{2+}$ at a known concentration (1 mM) in sub-second temporal resolution was performed using WINCS (FIGS. 30A-F). The small amount of $Mg^{2+}$ dose was injected through the flow injection analysis system 15 times. A pseudo-color plot was created by WINCS custom software with time on the x-axis and the applied potential on the y-axis with the current illustrated by a color gradient (FIG. 30A). The $Mg^{2+}$'s pattern of peaks on the pseudo-color plots was very similar to that of $Ca^{2+}$'s. Again, near −0.4V, it revealed a reductive peak for 10 seconds of injection. Also, just like $Ca^{2+}$, around +0.5V, +1.5V, and the reverse −0.4V oxidative currents were depicted. FIG. 30B demonstrates the cyclic voltammogram when $Mg^{2+}$ was first recorded. Similar to $Ca^{2+}$, the line with a reduction peak around −0.4V was the forward-going potential from −0.4V to +1.5V. FIG. 30C shows an oxidative peak at the switching potential 1.5V, which, again, will later be compared with adenosine's well-understood oxidative peak at 1.5V. FIG. 30D demonstrates that the initial cyclic voltammogram in the absence of $Ca^{2+}$ resulted in a large background charging current at the CFM by the rapid scanning of the potential, and addition of 2 mM $Ca^{2+}$ increased the background current modestly.

FIG. 30E shows WINCS-recorded fast-scan cyclic voltammetry of 2 mM $Mg^{2+}$ with an applied potential from −0.4V to +1.0V. The pseudo-color plot was produced by WINCS custom software, plotting time on the x-axis and the applied electrode potential on the y-axis with the color gradient. At approximately −0.15V, a light brown color portraying background current changes to dark blue and white for 10 seconds of injection of $Mg^{2+}$ into the flow cell, indicating a reductive current, was observed. At approximately +0.5, +1.0, and the returning 0.10V, the light brown color turned to green and purple for 10 seconds of the injection, showing an oxidative current. FIG. 30F illustrates the cyclic voltammogram acquired when $Mg^{2+}$ was first detected, where the line that starts with a reduction peak near −0.15V is the forward-going potential from −0.4V to +1.5V.

FIG. 31A depicts WINCS-collected FSCV pseudo-color plots for increasing concentrations (0.0 mM, 0.5 mM, 1.0 mM, and 2 mM). FIG. 31B shows a current versus time plot with oxidative peaks of the three different concentrations of $Mg^{2+}$ at 1.5V and a strong linear relationship among the oxidative currents at the switching potential 1.5V versus $Mg^{2+}$ concentrations examined (0.0 mM to 2 mM; n=4 injections per concentration). Its linear correlation coefficient ($r^2$) was 0.99. The $Mg^{2+}$ calibration curve information was as follows:

Best-fit values
  Slope=3.271±0.1249
  Y-intercept (when X=0.0)=0.05000±0.1652
  X-intercept (when Y=0.0)=−0.01528
  1/slope=0.3057
95% Confidence Intervals
  Slope=2.976 to 3.567
  Y-intercept (when X=0.0)=−0.3407 to 0.4407
  X-intercept (when Y=0.0)=−0.1705 to 0.1205
Goodness of Fit
  $r^2$=0.9899
  Sy.x=0.2336
Is slope significantly non-zero?
  F=686.1
  DFn, DFd=1.000, 7.000
  P value<0.0001
  Deviation from zero? Significant
Data
  Number of X values=3
  Maximum number of Y replicates=3
  Total number of values=9
  Number of missing values=0
Similarity of $Ca^{2+}$ and $Mg^{2+}$ FIGS. 32A and 32 illustrate two very similar WINCS-recorded FSCV pseudo-color plots of $Ca^{2+}$ (0.5 mM) and $Mg^{2+}$ (2 mM). The $Ca^{2+}$ voltammogram (FIG. 32A) and the $Mg^{2+}$ voltammogram (FIG. 32B) exhibited almost identical and definite patterns. They both demonstrated oxidative peaks at 0.5V, 1.5V, and returning −0.4V and reductive peaks at foregoing −0.4V. Such association was shown through FIG. 32C and FIG. 32D. As shown in FIG. 32C, with the thin line indicating the $Mg^{2+}$ voltammogram and the thick line indicating the $Ca^{2+}$ voltammogram, although both lines are not perfectly synchronized, they demonstrate acute similarity. Such equivalence was again exemplified through FIG. 32D, which revealed not perfectly integrated but almost identical peaks at 1.5V.

Adenosine, $Ca^{2+}$, and $Mg^{2+}$

Adenosine was applied as an example of how the recordings of $Ca^{2+}$ and $Mg^{2+}$ can affect consideration of adenosine from in vivo data with a peak at the switching potential 1.5V. The voltammogram of the basal physiological extracellular concentration of adenosine, which is 10 µM, depicts two oxidative peaks: the first peak at 1.5V and the second at 1.0V (Shon et al., *J. Neurosurg.*, 112(3):539-48 (2010)). Even though adenosine's voltammogram appears different compared to the voltammograms of $Ca^{2+}$ and $Mg^{2+}$, they all have oxidative peaks near 1.5V. This demonstrates that recorded data in vivo with a peak at 1.5V may not be easily determined to be adenosine, for $Ca^{2+}$ and $Mg^{2+}$ also have a possibility of being recorded, showing oxidative peaks at the same voltage. This shows the possible influence or interference of $Ca^{2+}$ and $Mg^{2+}$ cation channel potential change on FSCV of adenosine or other neurotransmitters, which may occur simultaneously.

The results provided herein demonstrate that FSCV can detect the concentration changes of two important physiological cations, $Ca^{2+}$ and $Mg^{2+}$, using WINCS. These results can be taken into consideration in the interpretation of the FSCV recordings of various neurotransmitters during the wireless monitoring of high frequency stimulation evoked changes in the brain.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A deep brain stimulation system, comprising:
  a probe comprising (i) an electrode configured to apply an electrical stimulus to a region of brain tissue using a fast-scan cyclic voltammetry technique and (ii) a first sensor configured to be located in said region of said brain tissue during application of said electrical stimulus and to generate a signal indicative of a detected level of said neurochemical or said ion present in said region of said brain tissue, and
  a control unit in communication with said probe, wherein said control unit is configured to receive information from said probe about said detected level of said neurochemical or said ion and is configured to send information to said probe about a level or a timing of electrical stimulus to apply to said region of said brain tissue,
  wherein said probe comprises two or more sensors including the first sensor, wherein one of said two or more sensors is configured to detect a first neurochemical or ion, wherein another of said two or more sensors is configured to detect a second neurochemical or ion.

2. The deep brain stimulation system of claim 1, wherein said first sensor is configured to detect a neurochemical selected from the group consisting of dopamine, serotonin, adenosine, adenine mono- or tri-phosphate, norepinephrine, GABA, histamine, acetylcholine, glutamate, aspartate, epinephrine, nitric oxide, glycine, tryptamine, phenylethylamine, tyramine, and octopamine.

3. The deep brain stimulation system of claim 1, wherein said first sensor is configured to detect an ion selected from the group consisting of calcium, magnesium, sodium, potassium, protons, iron, copper, chromium, lead, mercury, cobalt, gold, lithium, cesium, barium, zinc, chloride, bicarbonate, phosphate, bromide, iodide, sulfide, oxide, sulfide, and fluoride.

4. The deep brain stimulation system of claim 1, wherein said two or more sensors are respectively configured to detect two or more of dopamine, serotonin, adenosine, norephinephrine, GABA, histamine, acetylcholine, or glutamate.

5. The deep brain stimulation system of claim 1, wherein said probe comprises a second sensor that is configured to detect electrical brain signals.

6. The deep brain stimulation system of claim 1, wherein said probe and said control unit are physically connected.

7. The deep brain stimulation system of claim 1, wherein said electrode comprises a carbon fiber microelectrode (CFM).

8. The deep brain stimulation system of claim 7, wherein a length of said CFM is about 100 micrometers and a diameter of said CFM is about 5 micrometers.

9. The deep brain stimulation system of claim 1, wherein said electrode is configured to apply said electrical stimulus to said region of said brain tissue using a voltage scan.

10. The deep brain stimulation system of claim 9, wherein a frequency of said voltage scan is 10 Hertz.

11. The deep brain stimulation system of claim 1, further comprising an accelerometer that is configured to be fixed to a patient to detect motions of at least a portion of said patient's body,
wherein said control unit is configured to receive information from said accelerometer about said detected motions of said at least a portion of said patient's body,
wherein said information that said control unit is configured to send to said probe about said level or said timing of electrical stimulus to apply to said region of said brain tissue is determined based at least on said information from said accelerometer about said detected motions of said at least a portion of said patient's body.

12. A deep brain stimulation system, comprising:
a probe comprising (i) an electrode configured to apply an electrical stimulus to a region of brain tissue using a fast-scan cyclic voltammetry technique and (ii) a sensor configured to be located in said region of said brain tissue during application of said electrical stimulus and to generate a signal indicative of a detected level of said neurochemical or said ion present in said region of said brain tissue, and
a control unit in communication with said probe, wherein said control unit is configured to receive information from said probe about said detected level of said neurochemical or said ion and is configured to send information to said probe about a level or a timing of electrical stimulus to apply to said region of said brain tissue,
wherein said electrical stimulus comprises a voltage scan, wherein said probe is configured to apply different voltage scans within said region of said brain tissue to detect different neurochemicals or ions.

13. The deep brain stimulation system of claim 12, wherein said control unit is configured (i) to be located externally of a body of a patient and (ii) to communicate via a wireless channel with said probe.

14. The deep brain stimulation system of claim 12, wherein said sensor is configured to detect a neurochemical selected from the group consisting of dopamine, serotonin, adenosine, adenine mono- or tri-phosphate, norepinephrine, GABA, histamine, acetylcholine, glutamate, aspartate, epinephrine, nitric oxide, glycine, tryptamine, phenylethylamine, tyramine, and octopamine.

15. The deep brain stimulation system of claim 12, wherein said electrode comprises a carbon fiber microelectrode (CFM).

16. The deep brain stimulation system of claim 15, wherein a length of said CFM is about 100 micrometers and a diameter of said CFM is about 5 micrometers.

17. A deep brain stimulation system, comprising:
a probe comprising (i) an electrode configured to apply an electrical stimulus to a region of brain tissue using a fast-scan cyclic voltammetry technique and (ii) a sensor configured to be located in said region of said brain tissue during application of said electrical stimulus and to generate a signal indicative of a detected level of said neurochemical or said ion present in said region of said brain tissue, and
a control unit in communication with said probe, wherein said control unit is configured to receive information from said probe about said detected level of said neurochemical or said ion and is configured to send information to said probe about a level or a timing of electrical stimulus to apply to said region of said brain tissue,
wherein said electrode includes multiple independent active areas for detecting different neurochemicals or ions.

18. The deep brain stimulation system of claim 17, wherein said control unit is configured (i) to be located externally of a body of a patient and (ii) to communicate via a wireless channel with said probe.

19. The deep brain stimulation system of claim 17, wherein said sensor is configured to detect a neurochemical selected from the group consisting of dopamine, serotonin, adenosine, adenine mono- or tri-phosphate, norepinephrine, GABA, histamine, acetylcholine, glutamate, aspartate, epinephrine, nitric oxide, glycine, tryptamine, phenylethylamine, tyramine, and octopamine.

20. The deep brain stimulation system of claim 17, further comprising an accelerometer that is configured to be fixed to a patient to detect motions of at least a portion of said patient's body,
wherein said control unit is configured to receive information from said accelerometer about said detected motions of said at least a portion of said patient's body,
wherein said information that said control unit is configured to send to said probe about said level or said timing of electrical stimulus to apply to said region of said brain tissue is determined based at least on said information from said accelerometer about said detected motions of said at least a portion of said patient's body.

* * * * *

UNITED STATES PATENT AND TRADEMARK OFFICE
CERTIFICATE OF CORRECTION

PATENT NO. : 9,603,522 B2
APPLICATION NO. : 13/392387
DATED : March 28, 2017
INVENTOR(S) : Kendall H. Lee, Kevin E. Bennet and Charles D. Blaha It is certified that error appears in the above-identified patent and that said Letters Patent is hereby corrected as shown below:

On the Title Page

Column 2 (Primary Examiner), please delete "Navim" and insert -- Navin --, therefor;

In the Specification

Column 1, Line 9 (approx.), after first instance, "U.S.C." insert -- § --, therefor;

Column 1, Line 9 (approx.), after second instance, "U.S.C." insert -- § --, therefor;

In the Claims

Column 37, Line 11 (approx.), please delete "norephinephrine," and insert -- norepinephrine, --, therefor.

Signed and Sealed this
Eighth Day of August, 2017

Joseph Matal
*Performing the Functions and Duties of the*
*Under Secretary of Commerce for Intellectual Property and*
*Director of the United States Patent and Trademark Office*